United States Patent [19]
Skillicorn et al.

[11] Patent Number: 5,682,412
[45] Date of Patent: Oct. 28, 1997

[54] X-RAY SOURCE

[75] Inventors: Brian Skillicorn, Saratoga; George H. Fellingham, San Jose; Peter E. Loeffler, Los Gatos, all of Calif.

[73] Assignee: Cardiac Mariners, Incorporated, Los Gatos, Calif.

[21] Appl. No.: 717,611

[22] Filed: Sep. 20, 1996

Related U.S. Application Data

[63] Continuation of Ser. No. 386,884, Feb. 10, 1995, abandoned, which is a continuation-in-part of Ser. No. 375,501, Jan. 17, 1995, abandoned, which is a continuation of Ser. No. 42,742, Apr. 5, 1993, abandoned.

[51] Int. Cl.$^6$ .................................................. H01J 35/30
[52] U.S. Cl. ........................ 378/98.6; 378/113; 378/137
[58] Field of Search ..................................... 378/137, 113, 378/98.6

[56] References Cited

U.S. PATENT DOCUMENTS

| | | | |
|---|---|---|---|
| 2,638,554 | 5/1953 | Bartow et al. | 250/99 |
| 2,667,585 | 1/1954 | Gradstein | 250/61.5 |
| 2,730,566 | 1/1956 | Bartow et al. | 378/146 |
| 2,825,817 | 3/1958 | North | 250/105 |
| 2,837,657 | 6/1958 | Craig et al. | 250/65 |
| 3,106,640 | 10/1963 | Oldendorf | 250/52 |
| 3,114,832 | 12/1963 | Alvarez. | |

(List continued on next page.)

OTHER PUBLICATIONS

Thomas S. Curry, III, et al., "Christensen's Physics of Diagnostic Radiology," pp. 1–522, Fourth Ed., Lea & Febiger, 1990.

Albert G. Richards, "Variable Depth Laminagraphy", *ISA–Biomedical Sciences Instrumentation, vol. 6, Imagery in Medicine, 7th Proc.*, May 1969, pp. 194–199.

Barrett et al., "The Theory of Image Formation, Detection, and Processing", vol. 2, *Radiological Imaging*, published at least by Dec., 1981, pp. 368–371.

Sashin et al., "Computer Electronic Radiography For Early Detection of Vascular Disease", vol. 173, SPIE, *Application of Optical Instrumentation in Medicine VII*, Mar., 1979, pp. 88–97.

Maravilla et al., "Digital Tomosynthesis: Technique for Electronic Reconstructive Tomography", vol. 4, *American Journal of Neuroradiology*, Jul./Aug., 1983, pp. 883–888.

Capp et al., "Photoelectronic Radiology Department", vol. 314, SPIE, *Digital Radiography*, Sep., 1981, pp. 2–8.

Gerald D. Pond, "Dynamic Linear Tomography and Routine Linear Tomography: a Clinical Comparison", vol. 233 SPIE *Application of Optical Instrumentation in Medicine VIII*, Apr., 1980, pp. 75–82.

ECRI, "Radiographic/Fluoroscopic Units, Mobile", *Healthcare Products Comparison System*, Sep. 1993, pp. 1–25.

OEC–Diasonics, Salt Lake City, OEC, "Series 9600 Mobile Digital Imaging System", *OEC–Diasonics Marketing Brochure*, published at least by Nov., 1994, pp. 1–3.

(List continued on next page.)

*Primary Examiner*—Craig E. Church
*Attorney, Agent, or Firm*—Lyon & Lyon LLP

[57] ABSTRACT

The x-ray source of the present invention comprises a charged particle beam generator and a vacuum enclosure assembly. The charged particle beam generator includes only a single electrical connection for providing high voltage to the electron gun. The power for the active circuits in the high voltage terminal of the charged particle beam generator is provided by a unique isolation transformer that has minimal losses and generates controlled magnetic flux. The generated charged particle beam is controlled through a series of dynamic and static focus coils and moved across the inner face of the target by a stepping coil assembly comprising x and y deflection coils as well as an x step and preferably a y step coil. Further, to minimize power usage, a control grid pinches off the charged particle beam during the stepping of the beam.

20 Claims, 38 Drawing Sheets

U.S. PATENT DOCUMENTS

| | | | |
|---|---|---|---|
| 3,499,146 | 3/1970 | Richards | 250/61.5 |
| 3,591,806 | 7/1971 | Brill et al. | 250/71.5 |
| 3,593,243 | 7/1971 | Trump et al. | 336/70 |
| 3,605,750 | 9/1971 | Sheridan et al. | 128/658 |
| 3,611,032 | 10/1971 | Skillicorn | 317/14 |
| 3,617,740 | 11/1971 | Skillicorn | 250/49.5 |
| 3,684,991 | 8/1972 | Trump et al. | 336/70 |
| 3,742,236 | 6/1973 | Richards | 250/321 |
| 3,746,872 | 7/1973 | Ashe et al. | 250/313 |
| 3,778,614 | 12/1973 | Hounsfield | 250/362 |
| 3,780,291 | 12/1973 | Stein et al. | 250/363 |
| 3,809,886 | 5/1974 | Cochran et al. | 250/323 |
| 3,818,220 | 6/1974 | Richards | 250/61.5 |
| 3,830,128 | 8/1974 | Cochran et al. | 83/451 |
| 3,855,471 | 12/1974 | Ikegami | 250/320 |
| 3,873,834 | 3/1975 | Dammann et al. | 250/323 |
| 3,890,521 | 6/1975 | Shroff | 313/55 |
| 3,919,556 | 11/1975 | Berninger | 250/366 |
| 3,922,552 | 11/1975 | Ledley | 250/369 |
| 3,924,129 | 12/1975 | LeMay | 250/336 |
| 3,925,660 | 12/1975 | Albert | 250/272 |
| 3,936,639 | 2/1976 | Barrett | 250/369 |
| 3,944,833 | 3/1976 | Hounsfield | 250/367 |
| 3,946,234 | 3/1976 | Hounsfield | 250/363 |
| 3,949,229 | 4/1976 | Albert | 250/401 |
| 3,973,128 | 8/1976 | LeMay | 250/445 |
| 3,979,594 | 9/1976 | Anger | 250/369 |
| 3,983,397 | 9/1976 | Albert | 250/406 |
| 3,992,631 | 11/1976 | Harte | 250/302 |
| 4,002,917 | 1/1977 | Mayo | 250/445 |
| 4,005,311 | 1/1977 | Ledley | 250/445 |
| 4,007,375 | 2/1977 | Albert | 250/404 |
| 4,010,370 | 3/1977 | LeMay | 250/366 |
| 4,017,730 | 4/1977 | Barrett | 250/363 |
| 4,029,948 | 6/1977 | Hounsfield | 235/151.3 |
| 4,031,395 | 6/1977 | LeMay | 250/360 |
| 4,032,787 | 6/1977 | Albert | 250/402 |
| 4,048,496 | 9/1977 | Albert | 250/272 |
| 4,052,619 | 10/1977 | Hounsfield | 250/363 |
| 4,057,745 | 11/1977 | Albert | 313/55 |
| 4,066,902 | 1/1978 | LeMay | 250/363 |
| 4,078,177 | 3/1978 | Tiemens | 250/323 |
| 4,086,492 | 4/1978 | Lodge et al. | 250/416 |
| 4,104,526 | 8/1978 | Albert | 250/403 |
| 4,144,457 | 3/1979 | Albert | 250/445 T |
| 4,149,076 | 4/1979 | Albert | 250/402 |
| 4,167,672 | 9/1979 | Richards | 250/445 |
| 4,188,640 | 2/1980 | Dittrich et al. | 358/111 |
| 4,196,351 | 4/1980 | Albert | 250/416 TV |
| 4,204,226 | 5/1980 | Mistretta et al. | 358/111 |
| 4,216,526 | 8/1980 | Karwowski | 364/414 |
| 4,234,794 | 11/1980 | Voinea et al. | 378/146 |
| 4,259,582 | 3/1981 | Albert | 250/402 |
| 4,259,583 | 3/1981 | Albert | 250/416 TV |
| 4,260,885 | 4/1981 | Albert | 250/277 |
| 4,263,916 | 4/1981 | Brooks et al. | 128/654 |
| 4,288,697 | 9/1981 | Albert | 250/505 |
| 4,321,473 | 3/1982 | Albert | 250/505 |
| 4,322,808 | 3/1982 | Weiss | 364/515 |
| 4,323,779 | 4/1982 | Albert | 250/401 |
| 4,383,327 | 5/1983 | Kruger | 378/146 |
| 4,465,540 | 8/1984 | Albert | 156/252 |
| 4,519,092 | 5/1985 | Albert | 378/45 |
| 4,573,183 | 2/1986 | Relihan | 378/108 |
| 4,577,637 | 3/1986 | Mueller, Jr. | 128/658 |
| 4,598,369 | 7/1986 | Wang et al. | 364/414 |
| 4,630,296 | 12/1986 | Haaker et al. | 378/2 |
| 4,646,338 | 2/1987 | Skillicorn | 378/110 |
| 4,694,480 | 9/1987 | Skillicorn | 378/119 |
| 4,730,350 | 3/1988 | Albert | 378/10 |
| 4,796,637 | 1/1989 | Mascuch et al. | 128/658 |
| 4,853,540 | 8/1989 | Nakajima | 250/327.2 |
| 4,873,708 | 10/1989 | Cusano et al. | 378/62 |
| 4,903,204 | 2/1990 | Dobbins, III | 364/413.24 |
| 4,945,894 | 8/1990 | Kawashima | 128/658 |
| 4,967,121 | 10/1990 | Nero | 315/411 |
| 4,974,929 | 12/1990 | Curry | 128/658 |
| 5,022,066 | 6/1991 | Haaker et al. | 378/2 |
| 5,029,338 | 7/1991 | Aichinger et al. | 378/108 |
| 5,132,539 | 7/1992 | Kwasnick et al. | 250/361 |
| 5,140,162 | 8/1992 | Stettner | 250/370.09 |
| 5,153,438 | 10/1992 | Kingsley et al. | 250/370 |
| 5,171,232 | 12/1992 | Castillo et al. | 128/658 |
| 5,185,773 | 2/1993 | Blossfeld et al. | 378/53 |
| 5,187,369 | 2/1993 | Kingsley et al. | 250/370 |
| 5,198,673 | 3/1993 | Rougeot et al. | 250/370 |
| 5,203,777 | 4/1993 | Lee | 128/658 |
| 5,231,654 | 7/1993 | Kwasnick et al. | 378/147 |
| 5,231,655 | 7/1993 | Wei et al. | 378/154 |
| 5,237,598 | 8/1993 | Albert | 378/146 |
| 5,259,012 | 11/1993 | Baker et al. | 378/21 |
| 5,267,296 | 11/1993 | Albert | 378/113 |
| 5,276,604 | 1/1994 | Messman | 363/65 |
| 5,293,417 | 3/1994 | Wei et al. | 378/147 |
| 5,303,282 | 4/1994 | Kwasnick et al. | 378/147 |
| 5,304,898 | 4/1994 | Kataoka et al. | 315/411 |
| 5,319,749 | 6/1994 | Haaker et al. | 395/166 |

OTHER PUBLICATIONS

Swinth et al., "Biomedical Probe Using a Fiber–optic Coupled Scintillator", Medical Physics, vol. 3, 1976, pp. 109–112.

W.C. Nixon, "High–resolution X–ray Projection Microscopy", vol. 232, *Proceedings of the Royal Society of London*, Nov., 1955, pp. 475–484.

George L. Clark, "The Encyclopedia of X–rays and Gamma Rays", 1963, pp. 608–610, 617.

V.E. Cosslett et al., "X–ray Microscopy", 1960, pp. 216–219, 296–303, 350–355, 368–369.

B. Skillicorn, "Insulators and X–Ray Tube Longevity: Some Theory and a Few Practical Hints", 1983, pp. 2–6.

Howard H. Pattee, Jr., "The Scanning X–ray Microscope", 1953, pp. 61–62.

Lewis Etter, "The Science of Ionizing Radiation", 1965, pp. 546–548.

R.M. Dolby et al., "A Spectrometer System for Long Wavelength X–ray Emission Microanalysis", *X–ray Microscopy and X–ray Microanalysis*, 1960, pp. 351–357.

Russell H. Morgan et al., "Clinical Potentialities of Screen Intensifying Systems", Nov., 1949, pp. 635–644.

Robert J. Moon, "Amplifying and Intensifying the Fluoroscopic image by Means of a Scanning X–Ray Tube", Oct. 6, 1950, pp. 389–395.

Howard H. Pattee, Jr., "Possibilities of the Scanning X–Ray Microscope", 1957, *X–Ray Microscopy and Microradiography*, pp. 367–375.

Center for Devices and Radiological Health, Radiological Health Bulletin, "FDA Draws Attention to Concerns about Radiation Risk from Fluoroscopy", Aug., 1992, pp. 1–3, 5.

Philips Photonics, "xP1700 Multichannel Photomultipliers", 1993, pp. 1–15.

Digiray, "Digiray's Reverse Geometry X–ray System", 1992 (?), pp. 1–2.

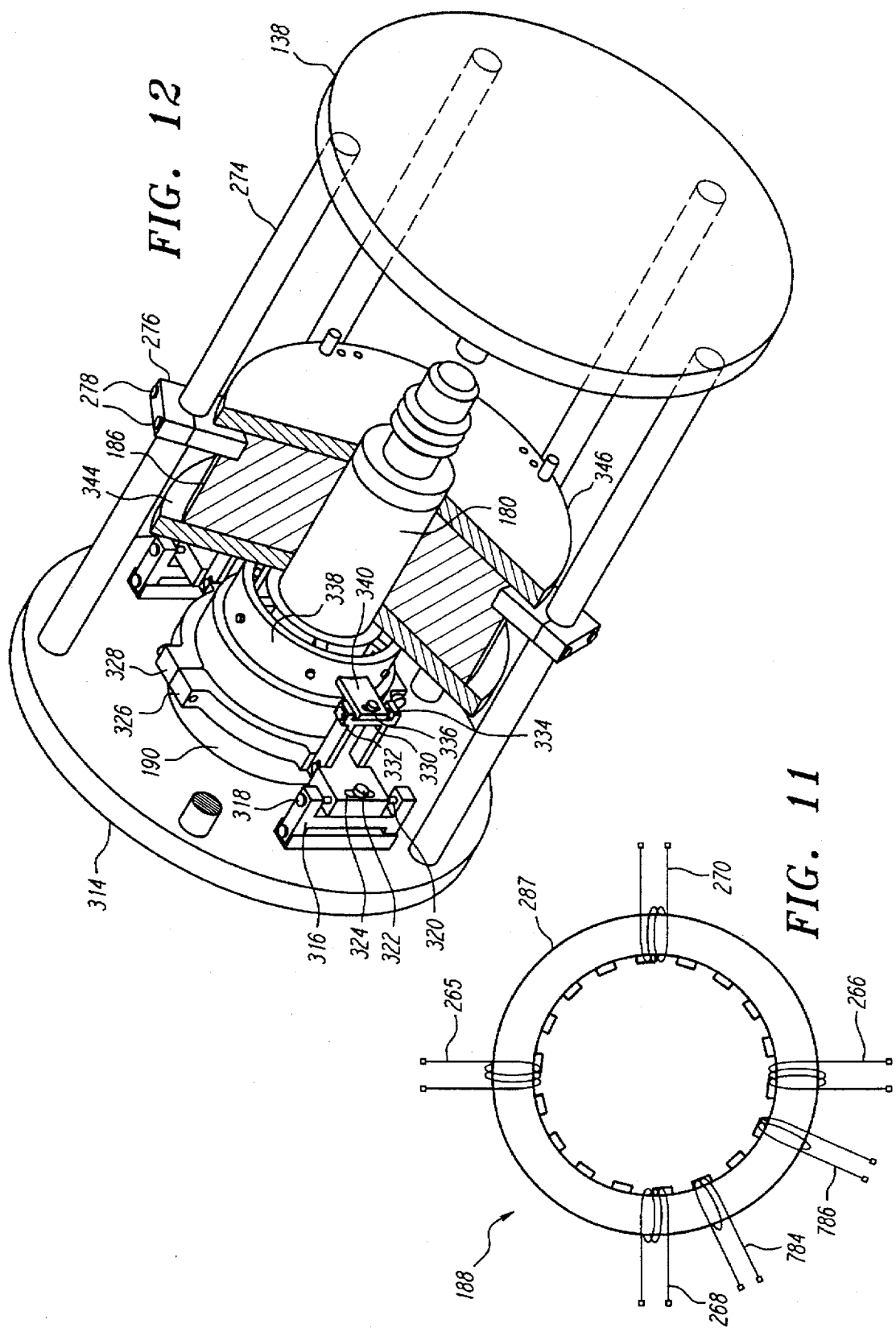

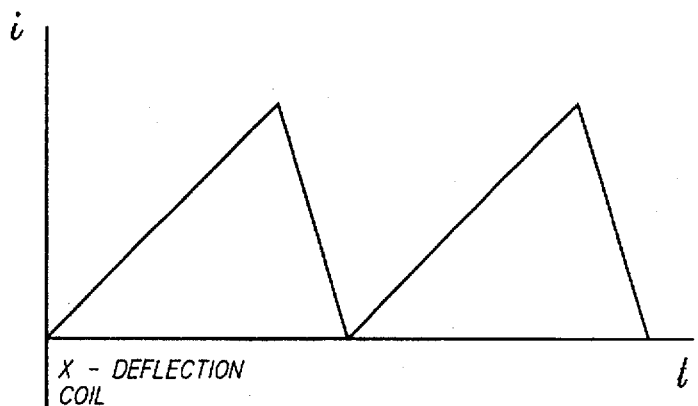
FIG. 14A
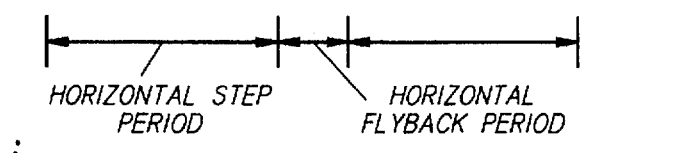
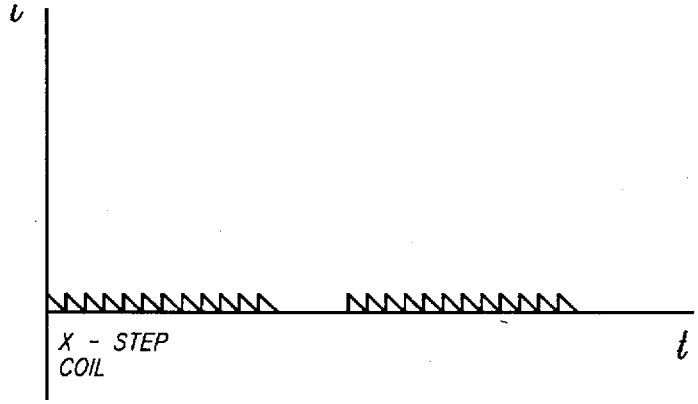
FIG. 14C
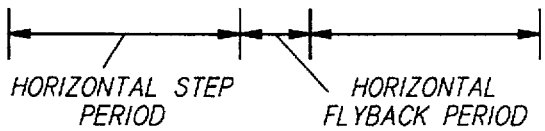
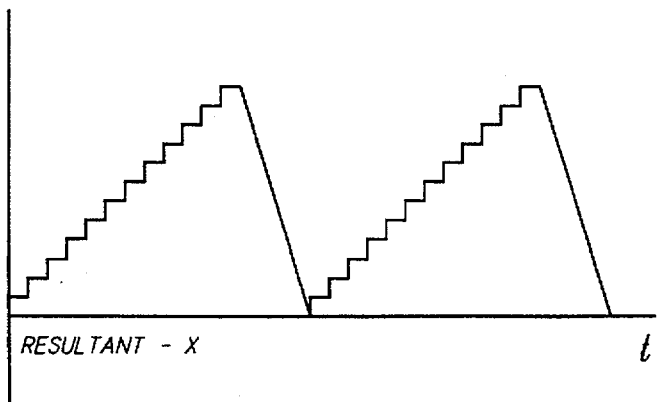
FIG. 14E
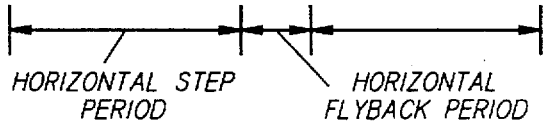

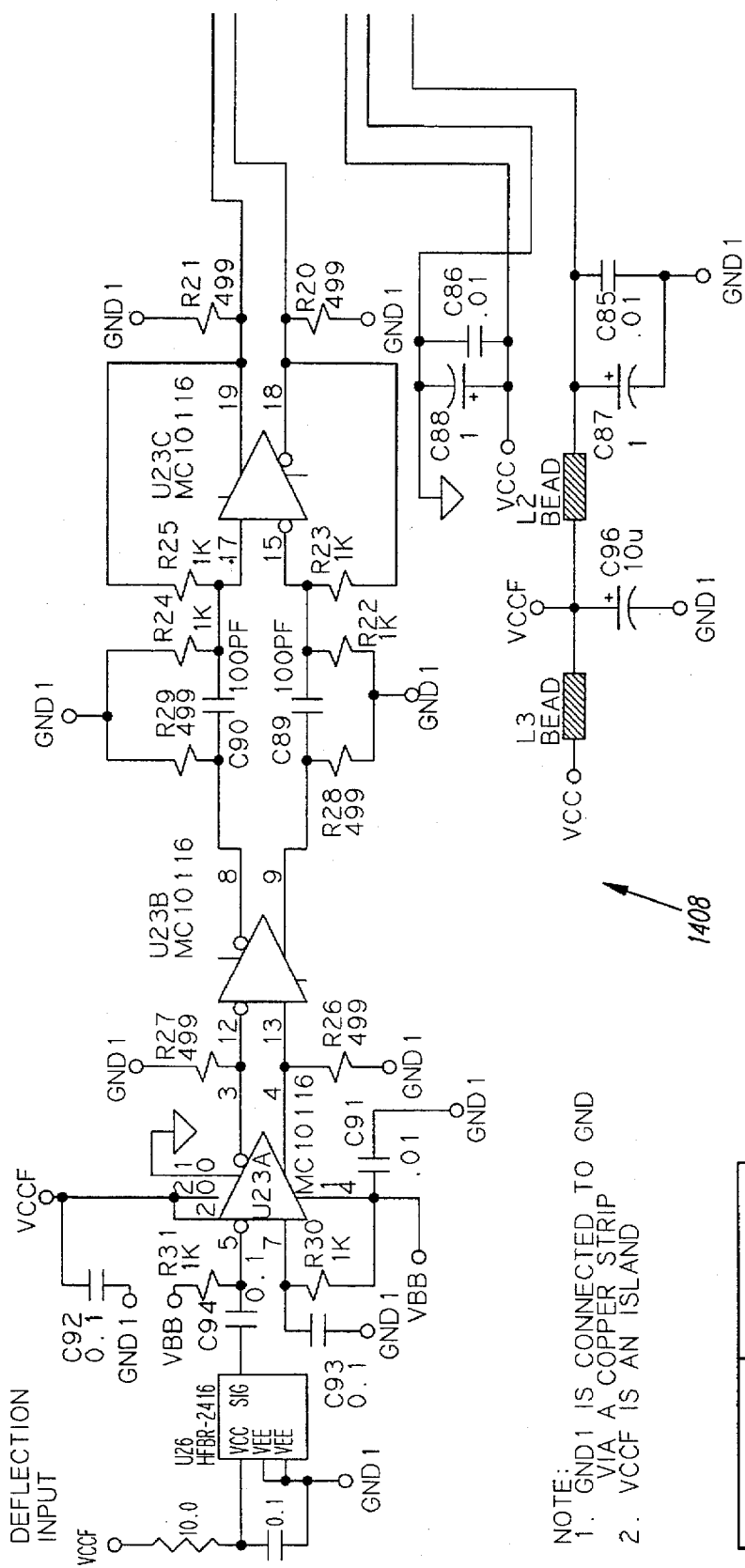

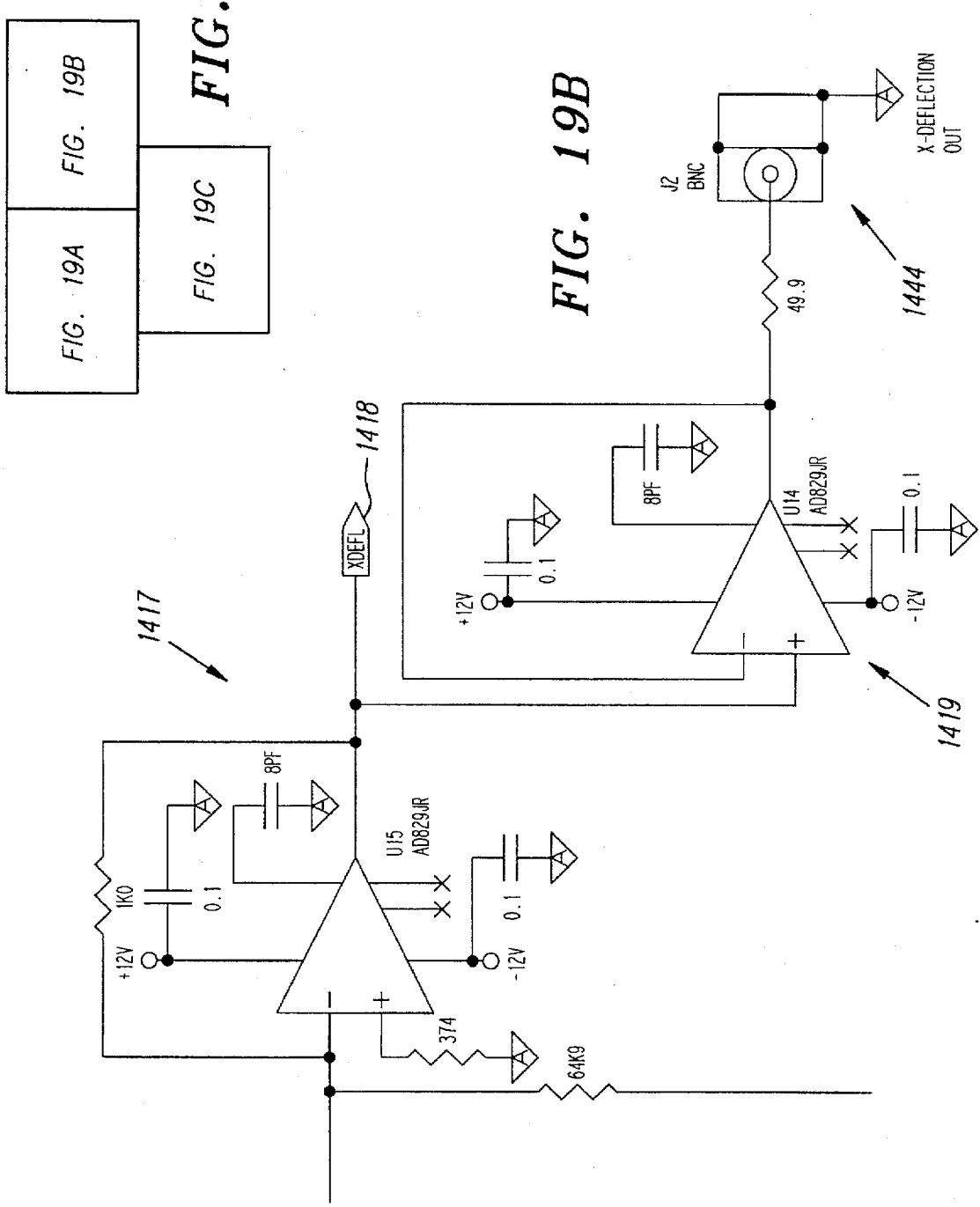

FIG. 21A
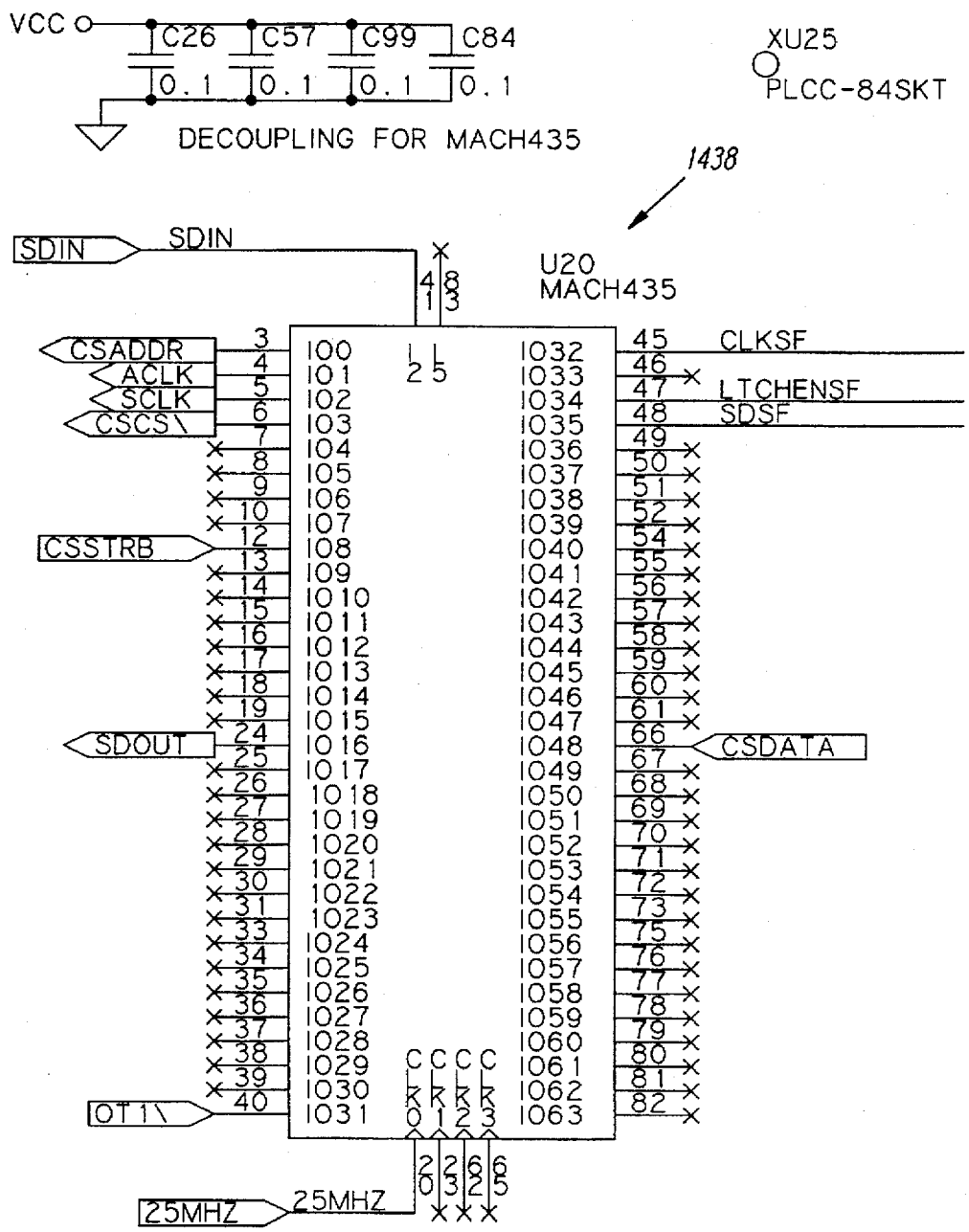
SERIAL DATA
PAL
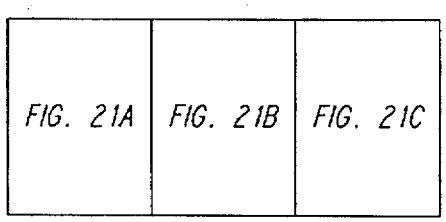
FIG. 21

| FIG. 23A | FIG. 23B | FIG. 23C |

1

X-RAY SOURCE

CROSS-REFERENCE TO RELATED APPLICATIONS

This application is a continuation of application Ser. No. 08/386,884, filed Feb. 10, 1995, abandoned, which is a continuation-in-part of U.S. patent application Ser. No. 08/375,501, filed Jan. 17, 1995, now abandoned which is a continuation of U.S. patent application Ser. No. 08/042,742, filed Apr. 5, 1993, now abandoned; and, of International Patent Application Serial No. PCT/US94/03737, filed Apr. 5, 1994, which designated the United States from which priority is claimed under the provisions of 35 U.S.C. §§ 120 and 365, all of which are incorporated herein by reference in their entirety. The reader is referred to copending U.S. patent application Ser. No. 08/387,292, and copending U.S. patent application Ser. No. 08/386,861, both filed Feb. 10, 1995 concurrently with this application, the disclosures of which are incorporated herein by reference in their entirety.

BACKGROUND OF THE INVENTION

1. Field of the Invention

The present invention pertains to the field of charged particle beam generators and x-ray tubes, and more specifically, scanning beam x-ray sources.

2. Description of Related Art

Real-time x-ray imaging is increasingly being required by medical procedures as therapeutic technologies advance. For example, many electro-physiologic cardiac procedures, peripheral vascular procedures, PTCA procedures (percutaneous transluminal catheter angioplasty), urological procedures, and orthopedic procedures rely on real-time x-ray imaging. In addition, modern medical procedures often require the use of instruments, such as catheters, that are inserted into the human body. These medical procedures often require the ability to discern the exact location of instruments that are inserted within the human body, often in conjunction with an accurate image of the surrounding body through the use of x-ray imaging.

A number of real-time x-ray imaging systems are known. These include fluoroscope-based systems where x-rays are projected into an object to be x-rayed and shadows caused by relatively x-ray opaque matter within the object are displayed on the fluoroscope located on the opposite side of the object from the x-ray source. Scanning x-ray tubes have been known in conjunction with the fluoroscopy art since at least the early 1950s. Moon, Amplifying and Intensifying the Fluoroscopic Image by Means of a Scanning X-ray Tube, Science, Oct. 6, 1950, pp. 389–395.

Reverse-geometry scanning beam x-ray imaging systems are also known. In such systems, an x-ray tube is employed to generate x-ray radiation. Within the x-ray tube, an electron beam is generated and focussed upon a small spot on the relatively large anode (transmission target) of the tube, inducing x-ray radiation emission from that spot. The electron beam is deflected (electromagnetically or electrostatically) in a raster scan pattern over the anode. A small x-ray detector is placed at a distance from the anode of the x-ray tube. The detector typically converts x-rays which strike it into an electrical signal in proportion to the detected x-ray flux. When an object is placed between the x-ray tube and the detector, x-rays are attenuated by the object in proportion to the x-ray density of the object. While the x-ray tube is in the scanning mode, the signal from the detector is inversely proportional to the x-ray density of the object.

Examples of known reverse-geometry scanning beam x-ray systems include those described in U.S. Pat. No. 3,949,229 to Albert; U.S. Pat. No. 4,032,787 to Albert; U.S. Pat. No. 4,057,745 to Albert; U.S. Pat. No. 4,144,457 to Albert; U.S. Pat. No. 4,149,076 to Albert; U.S. Pat. No. 4,196,351 to Albert; U.S. Pat. No. 4,259,582 to Albert; U.S. Pat. No. 4,259,583 to Albert; U.S. Pat. No. 4,288,697 to Albert; U.S. Pat. No. 4,321,473 to Albert; U.S. Pat. No. 4,323,779 to Albert; U.S. Pat. No. 4,465,540 to Albert; U.S. Pat. No. 4,519,092 to Albert; and U.S. Pat. No. 4,730,350 to Albert.

In a typical known embodiment of a reverse-geometry scanning beam system, an output signal from the detector is applied to the z-axis (luminance) input of a video monitor. This signal modulates the brightness of the viewing screen. The x and y inputs to the video monitor are typically derived from the signal that effects deflection of the electron beam of the x-ray tube. Therefore, the luminance of a point on the viewing screen is inversely proportional to the absorption of x-rays passing from the source, through the object, to the detector.

Accordingly there is a need for a source of x-rays that is both safe and economical as well as capable of being able to be positioned quickly and accurately across the face of a target anode.

SUMMARY OF THE INVENTION

The x-ray source of the present invention comprises a charged particle beam generator and an anode assembly. The preferred charged particle beam generator is an electron beam source comprising a single direct electrical connection for providing voltage to the electron gun. The power for the active circuits in the high voltage terminal of the electron beam source is provided by a unique isolation transformer that has minimal losses and generates controlled magnetic flux.

The generated electron beam is controlled through a series of dynamic and static focus coils and moved across the face of the target anode by a stepping coil assembly comprising x and y deflection coils as well as an x step and preferably a y step coil. Further, to minimize power usage, a control grid pinches off the electron beam during the stepping of the beam.

The entire x-ray source is packaged in a small form factor with sufficient safety features and that will allow for mounting of the source in traditional C-arms for use in medical applications without fear of danger to the patient or the treating physician.

These and many other objects and advantages of the present invention will become apparent to those of ordinary skill in the art from a consideration of the drawings and the description of the invention contained herein. The principles of the present invention may be employed in any application, medical or industrial.

BRIEF DESCRIPTION OF THE DRAWINGS

FIG. 11 is a diagram of a preferred fast deflection yoke structure.

FIG. 12 is an enlarged perspective diagram of the preferred deflection yoke and focus coil alignment structures.

FIGS. 14A–F are graphical representations of the current applied to deflection coils to move an electron beam in a raster scam pattern.

FIGS. 17A–B, 18, 19A–C, 20A–C, and 21A–C are schematics of the preferred beam controller interfaces. FIG. 17 is a key to FIGS. 17A–B. FIG. 19 is a key to FIGS. 19A–C. FIG. 20 is a key to FIGS. 20A–C. FIG. 21 is a key to FIGS. 21A–C.

DESCRIPTION OF THE PREFERRED EMBODIMENTS

Figure 1:
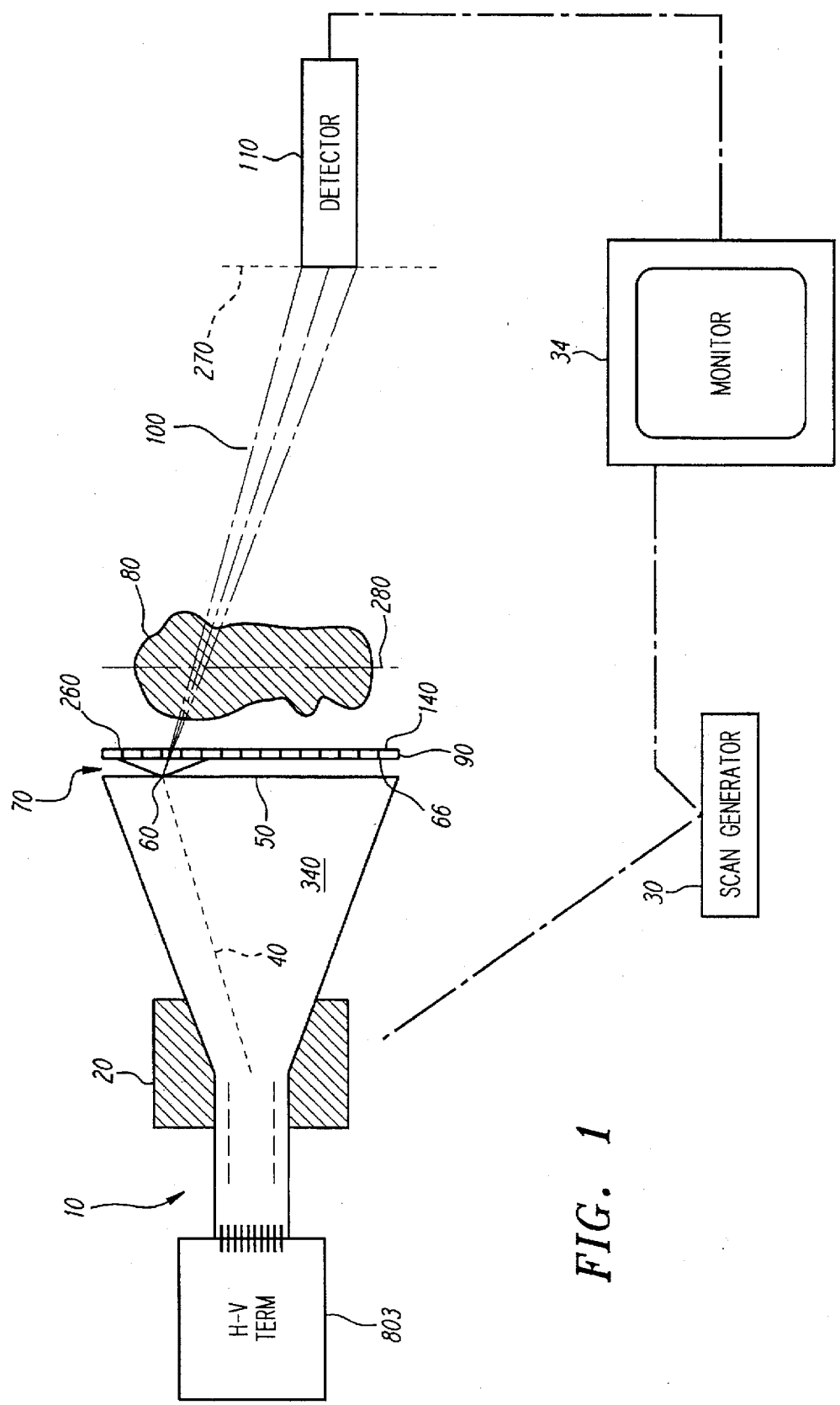
FIG. 1 is a diagram showing the basic components of a preferred scanning beam x-ray imaging system.

Turning to FIG. 1, an embodiment of a presently preferred x-ray source employed in a reverse geometry scanning beam x-ray imaging system is diagrammed. The x-ray source 10 preferably comprises an x-ray tube and a high voltage electron beam source. The high voltage electron beam source is preferably connected to an adjustable high-voltage power supply capable of generating approximately −70 kV to −120 kV. At this voltage level, scanning x-ray source 10 produces a spectrum of x-rays ranging to 120 keV. Scanning x-ray source 10 includes deflection coils 20 under the control of a scan generator 30. An electron beam 40 generated within high-voltage terminal 803 is scanned across a grounded anode target 50 in a predetermined pattern. For example, the predetermined pattern may be a raster scan pattern, a serpentine (or "S" shaped) pattern, a spiral pattern, a random pattern, a gaussian distribution pattern centered on a predetermined point of the target anode, or such other pattern as may be useful to the task at hand. Presently preferred is the serpentine (or "S" shaped) pattern which eliminates the need in a raster scan pattern for horizontal "fly back."

As electron beam 40 strikes anode target 50 at focal spot 60, x-rays 70 are emitted in all directions. For simplicity, only a portion of the x-rays are shown. The x-rays preferably pass through a collimator toward the object 80 to be investigated. To optimize system performance of the presently preferred embodiment, a cone of x-ray photons should be generated that will diverge in a manner that will just cover the multi-detector array 110. This is preferably accomplished by placing a collimating element between the anode target 50 of the x-ray source 10 and the multi-detector array 110 and more preferably between object 80 and x-ray source 10. A more detailed explanation of the system parameters can be found in copending U.S. patent application Ser. No. 08/386,861, which has been incorporated herein by reference in its entirety.

The presently preferred configuration for this collimating element is a grid of x-ray transmissive cylinders or apertures 140. Collimation grid 90 is designed to permit passage to only those x-rays whose axes are in a path that directly intersects the multi-detector array 110. Collimation grid 90 preferably does not move with respect to multi-detector array 110 while the system is in operation. Thus, as electron beam 40 is scanned across anode target 50, at any given moment there is only a single x-ray pencil beam 100 which passes through object 80 to multi-detector array 110.

The output of multi-detector array 110 is processed and displayed by control electronics/monitor 34 as an intensity value on a display monitor as described in copending and incorporated U.S. patent application Ser. No. 08/836,861, which has been incorporated herein by reference in its entirety.

Figure 2:
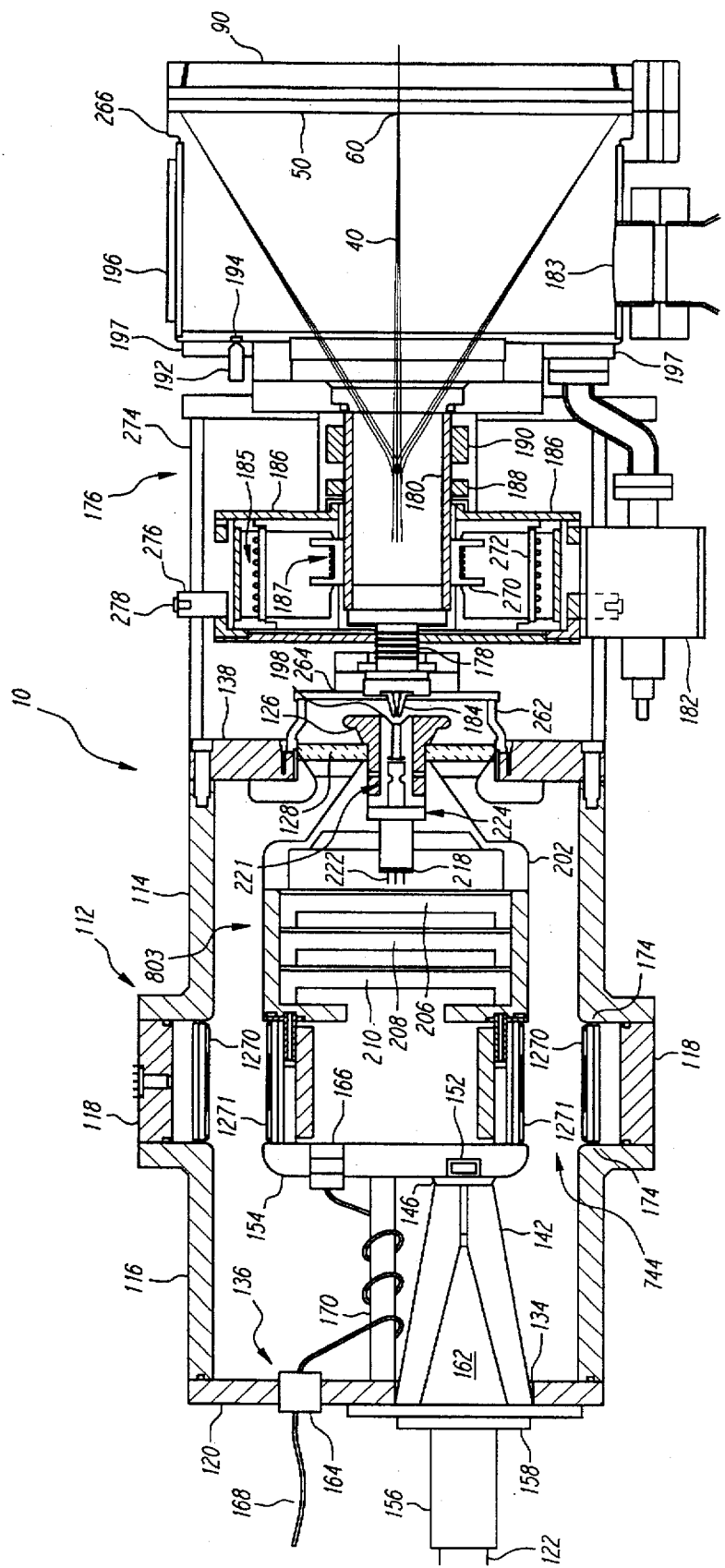
FIG. 2 is a cross-sectional side view of a preferred scanning beam x-ray tube.

FIG. 2 is a cross-sectional diagram of the presently preferred scanning beam x-ray source 10 which comprises an electron beam source 112 and a vacuum envelope assembly 176.

Electron beam source 112 is comprised of two aluminum flanged cylinders 114 and 116 bolted to central aluminum cylinder 118. Rear endplate 120, fabricated from aluminum with two sealed openings 134 and 136, is bolted to the rear of aluminum flanged cylinder 116. Front endplate 138, fabricated of aluminum with a sealed central apertured ceramic disc 128, is bolted to the front of aluminum flanged cylinders and the central cylinder. This method of construction permits electron beam source 112 to contain an insulating fluid within its confines, with ceramic disc 128 forming a seal between electron beam source 112 and vacuum envelope assembly 176. It is to be understood that any suitably designed housing is within the contemplation of the current inventions.

High-voltage cable 122, extending from an external high-voltage power source (not shown), supplies a potential preferably variable between −70 kV to −120 kV to generate an electron beam. The energy of this electron beam is between 70 kev and 120 keV which corresponds to the potential applied through high voltage cable 122. The preferred method of connecting high voltage cable 122 to the high voltage terminal assembly 803 is through use of molded epoxy cable receptacle 142 which has an integral metal mounting flange. Receptacle 142 passes through opening 134 and is sealed to end plate 120 with an O-ring seal. High voltage cable 122 is fitted into a strain relief sleeve 156 fastened by screws through integral flange 158 to the integral metal flange of cable receptacle 142. A rubber end piece 162, preferably ethylene propylene rubber, is shaped to conform with the conical orifice in cable receptacle 142 and is molded directly to the end of high voltage cable 122. For assembly, rubber end piece 162 is coated with silicone grease and is tightly compressed into the orifice in cable receptacle 142 to minimize electrical breakdown along the interface between rubber end piece 162 and cable receptacle 142. High voltage cable 122 contains electrostatic shielding (not shown) which is connected to ground within sleeve 156. Electrical contact is established between high voltage cable 122 and contact plate 146 by a conductive rod, thereby forming an electrical connection through conducting spring 152 to high voltage terminal assembly 803. Conducting spring 152 is preferably received in an indentation in the high voltage terminal endplate 154 of high voltage terminal assembly 803.

An insulating medium preferably surrounds high voltage terminal assembly 803 to allow small distances between the high voltage terminal assembly 803 and the outer walls of the electron beam source 112. Preferably, the insulating medium should be able to allow a high electrical potential of at least −120 kV to be impressed across this distance and maintained without electrical breakdown. The presently preferred insulating medium is sulphur hexafluoride gas ($SF_6$), which is preferably maintained at a pressure of approximately 60 psig and at a temperature less than 60° C. Other insulating media, such as transformer oil, can also be employed in place of $SF_6$.

Preferably fitted within aperture 136 of rear endplate 120 is a feedthrough assembly 164 through which eight fiber optic cables enter electron beam source 112. For purposes of illustration only, the eight fiber optic single cables are shown as a single cable 168 in FIG. 2. The fiber optic cables 168 are preferably sealed into feedthrough assembly 164 by embedding them in epoxy resin in order to prevent leakage of the $SF_6$ gas.

High voltage terminal assembly 803 is preferably insulated to withstand the applied high voltage by means of ceramic disc 128 set within the front plate 138. High voltage terminal assembly 803 is also preferably mechanically supported by means of ceramic disc 128 only, to form a cantilever.

An isolation transformer 744 supplies power to the components within the high-voltage terminal assembly 803. The secondary 1271 of the isolation transformer 744 is located within the high-voltage terminal 803. The primary 1270 is disposed coaxially around the secondary 1271, but is physically separated from the secondary 1271 by an insulating gap filled with the $SF_6$ insulating medium. The isolation transformer 744 is more fully discussed in the detailed descriptions of FIGS. 6–10.

Vacuum envelope assembly 176, which is preferably at ground potential, generally comprises the entire structure depicted in FIG. 2 to the right of the front endplate 138. The interior of the vacuum envelope assembly 176 forms the pathway for the electron beam 40 from the high voltage terminal assembly 803 to the anode target 50. A tapered cylinder ring 262 extending from the front endplate 138 of the electron beam source 112 is welded to disc 264. An accelerating anode 184 with an axial through-hole is preferably screwed to the center of disc 264. Hereinafter, anode target 50 and accelerating anode 184 are referred to as target 50 and anode 184, respectively, for simplicity and clarity.

The interior of the vacuum envelope assembly 176 is maintained at a reduced pressure, preferably less than $10^{-7}$ mm Hg. Vacuum envelope assembly 176 is initially evacuated by means of a negative pressure source mounted on a vacuum stand attached to tube and flange assembly 183. During initial evacuation, vacuum envelope assembly 176 is preferably baked out at an elevated temperature (>200° C.) to outgas all items on the interior. During this high temperature bake-out, all components of electron beam source 112, except the front end plate 138, are preferably removed from x-ray source 10 so that they are not damaged by the high temperature. After bake-out, x-ray source 10 is reassembled and conditioned, or high voltage processed, by operating the x-ray source at greater than normal voltage and current. The vacuum envelope assembly 126 is sealed off from the vacuum stand by sealing the tube of assembly 183 using a conventional pinch-off tool. Thereafter the reduced pressure in vacuum envelope assembly 176 is preferably maintained through the use of getter-ion pump 182. Alternatively, vacuum envelope assembly 176 can be a "sealed" tube design which consequently eliminates the need for a getter-ion pump.

Electron gun 198 protrudes from the high-voltage terminal 803 through ceramic disc 128 into the vacuum envelope assembly 176. Electrode 126 preferably extends from the ceramic disc 128, surrounding the emitting end of electron gun 198. Electrode 126 and anode 184 are shaped to control the electrostatic field configuration in the accelerating space between electrode 126 and anode 184, thereby ensuring that electron beam 40 is correctly focussed through the axial hole in anode 184. Additional shaping of electrode 126 controls the electrostatic field configuration across the surface of ceramic disc 128 so that the chance of electrical breakdown across the surface of disc 128 is minimized. On reaching anode 184, the electron beam 40 has acquired an energy expressed in electron volts substantially equal numerically to the voltage applied between electron gun 198 and anode 184. In its continuing path to target 50, electron beam 40 is preferably not subjected to any additional axial forces so upon impact at focal spot 60, the energy of electron beam 40 is essentially the same as that acquired at anode 184.

After leaving the axial hole of anode 184, electron beam 40 passes through a magnetic focus lens assembly 186 which is preferably a thin lens design comprising a cylindrical steel magnetic circuit with a U-shaped section. Static focus coil 185 is preferably wound on coil form 272 within this magnetic circuit. Dynamic focus coil 187 is preferably located within the magnetic circuit air gap and is preferably wound on a bobbin shaped coil form 270. Dynamic focus coil 187 is preferably wound with substantially fewer turns of wire than static focus coil 184 so that dynamic focus coil 187 has a low inductance, thus permitting the current flowing in the dynamic focus coil 187 to be changed rapidly. Currents flowing in static focus coil 185 and dynamic focus coil 187 cause electron beam 40 to be brought to a focus at focal spot 60. When used with a collimation grid, the size of the focal spot 60 is important. It should be small enough to maximize the transmission of x-ray flux through the apertures in collimation grid 90 but, if it is too small, the resulting excessively high power density concentrated in focal spot 60 could cause local melting of the surface of target 50. It has been found that a focal spot size of 0.3 mm is preferred when x-ray source 10 is used in conjunction with the collimation grid disclosed in U.S. patent application Ser. No. 08/386,861, which has been incorporated herein by reference in its entirety.

From the magnetic focus lens assembly, the path of electron beam 40 is preferably controlled by a two-part magnetic deflection system comprising slow deflection yoke 190 and fast deflection yoke 188 disposed coaxially around ceramic cylinder 180. The deflection yokes are described more fully in connection with the detailed descriptions of FIGS. 11–15. Ceramic cylinder 180 is preferably formed of a ceramic material, as opposed to metal, because the rapidly changing magnetic fields produced by the deflection yokes, 190 and 188, would induce eddy currents in a metal cylinder which would inhibit penetration of the magnetic fields and so interfere with the accurate deflection of electron beam 40. Ceramic cylinder 180 is preferably formed of alumina, coated on the inside with a thin high-resistance coating of a nickel-chromium alloy which serves to prevent the build up of an electrostatic charge which will cause undesirable deflections of electron beam 40. The resistance of this coating is preferably high, and is preferably 1,000 ohms when measured between the two ends of ceramic cylinder 180, to minimize induced eddy currents. Stainless steel bellows 178 provides strain relieving mechanical connecting means to ceramic cylinder 180 to avoid the application of stress to the ceramic cylinder caused by, for example, mechanical misalignment.

As electron beam 40 is deflected in the desired scanning pattern across the face of target 50, the length of the electron beam path will vary. To compensate for this, the strength of the magnetic focus lens assembly 186 is preferably varied in synchronism with the scan to maintain the optimal size of focal spot 60. This is preferably accomplished by operating the static focus coil 185 at a fixed current. The small changes in strength of the field generated by dynamic focus coil 187 required to maintain the optimal size of focal spot 60 are achieved by modulating the current flowing in dynamic focus coil 187 in synchronism with the currents flowing in deflection yokes 188 and 190. The preferred means to control and drive the currents in the dynamic focus coil 187 and static focus coil 185 are discussed more fully in copending U.S. patent application Ser. No. 08/386,861, which has been incorporated herein by reference in its entirety.

X-rays are produced when electron beam 40 strikes target 50, which is preferably a circular plate with an active diameter of 25.4 cm (10 in). A collimation grid 90 containing an array of x-ray transmissive apertures is preferably disposed between target 50 and multi-detector array 110. Target 50 and collimation grid 90 are discussed more fully in conjunction with the detailed description of FIG. 3.

Infra-red temperature sensor 192 monitors target 50 for excessive temperature conditions through viewing window 194 located in a wall of end bell assembly 266 opposite target 50. Excessive temperature conditions on target 50 may arise, e.g., if a malfunction causes electron beam 40 to dwell for too long in one spot on target 50, instead of being scanned across its face. Infra-red sensor 192 preferably detects for excessively high temperatures by monitoring the amount of, or spectral shifts in, the luminosity of the face of target 50. The response time of sensor 192 is preferably of the order of one microsecond to avoid target burn-out.

Cooling jacket 196 and cooling plate 197 are preferably mounted on the exterior front wall and exterior perimeter walls of the end bell assembly 266, to remove heat generated by electrons which are back scattered from target 50 during normal operation of scanning beam x-ray source 10. Heat is removed from cooling jacket 196 and cooling plate 197 by use of a cooling fluid, preferably Fluorinert™, available from 3M Corporation, which is preferably circulated through an external heat exchanger (not shown).

In the preferred embodiment, end bell assembly 266 is fabricated from stainless steel, conical in shape and double walled so that the cooling function can be achieved by circulating a cooling fluid in the space between the internal and external walls, thus the need for cooling plate 197 is consequently eliminated. The apex angle of the conical end bell assembly 266 preferably conforms with that of the conical volume swept out by electron beam 40 while the radial dimensions of the inside wall of the cone are such as to provide preferably 1.2 cm spacing to the conical volume swept out by electron beam 40. This preferred shape reduces the internal surface area and the enclosed volume of end bell assembly 266 and the time required to evacuate the vacuum envelope assembly 176 to an acceptably low pressure.

Figures 3, 4:
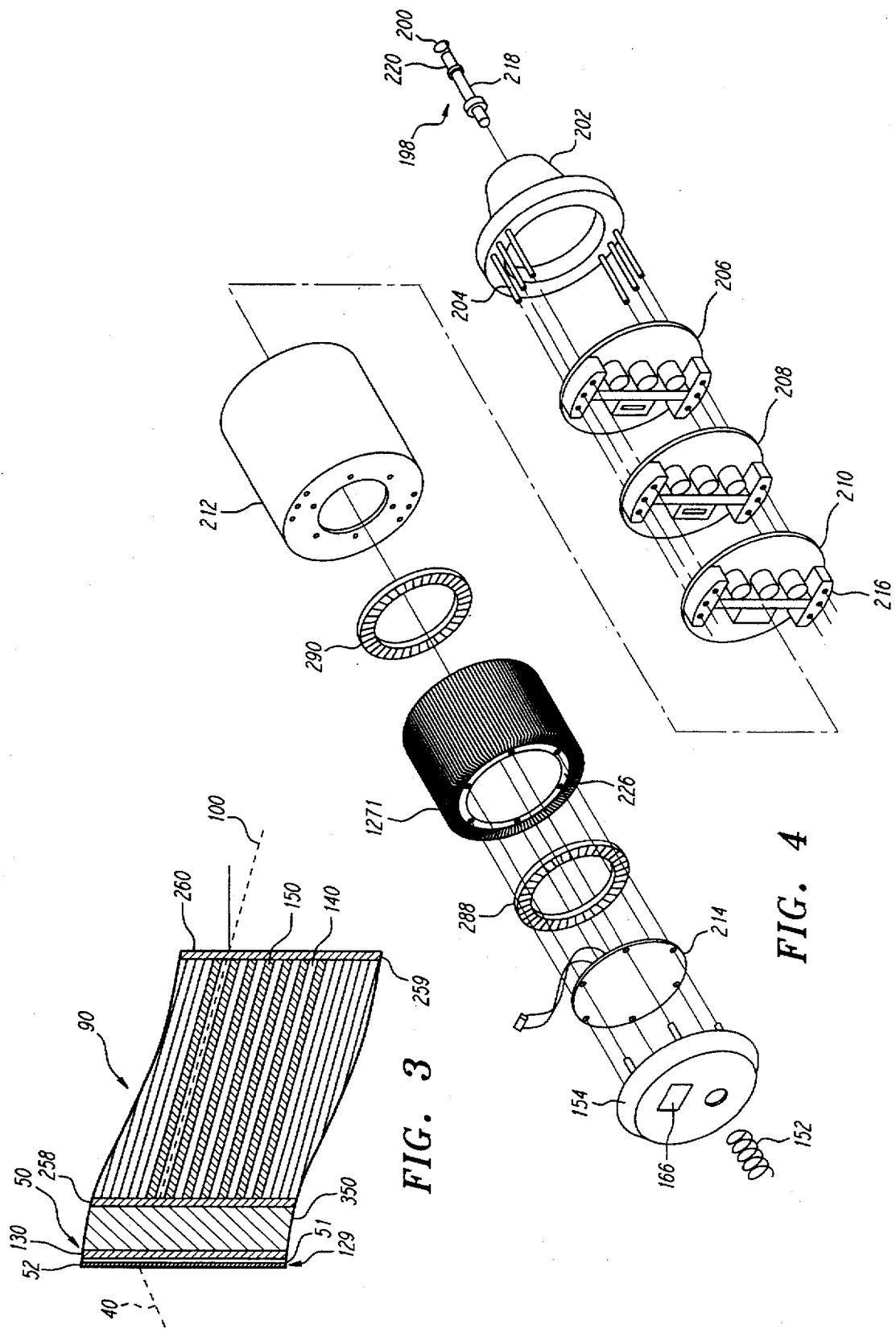
FIG. 3 is an enlarged partial cross sectional representation of a preferred target and collimation grid.
FIG. 4 is an exploded perspective view of a preferred high-voltage terminal assembly.

FIG. 3 depicts a magnified diagrammatic view of the preferred target 50 and collimation grid 90 assembly. Target 50 preferably comprises a target layer 129 supported by beryllium target support 130. A preferred construction of target layer 129 is a first layer of niobium 51 approximately 1 micron thick applied to target support 130 to which is then applied a second layer of tantalum 52 approximately 5 microns thick. The preferred method of application for niobium 51 and tantalum 52 is by sputtering. Alternative methods include chemical vapor deposition, evaporation and ion plating. Niobium layer 51 functions as a resilient layer which has a coefficient of thermal expansion between those of beryllium and tantalum to help prevent the formation of stress cracks in the tantalum layer 51, which may be caused by the high instantaneous temperature difference between the beryllium and the tantalum at focal spot 60 with consequent differential expansion between the tantalum and the beryllium substrate which can cause cracking. In an alternative method for application of the target layer 129 to the target support 130, the coating process can be performed at an elevated temperature so that subsequent cooling produces a compressive stress in the target layer 129 to reduce the operating tensile stress in target layer 129 at focal spot 60 by an amount approximately equal to the initial compressive stress. Another embodiment is a layer of tantalum deposited directly on the target support 130. Yet another embodiment is a target layer 129 of an alloy of tungsten and rhenium. Still another embodiment is a target layer 139 of tungsten. In each of these embodiments an intermediate layer of a resilient material such as niobium may be used. Tungsten, tantalum and tungsten-rhenium are preferred materials for target layer 129 because they have high atomic numbers, making them efficient producers of x-rays, coupled with high thermal conductivity, high specific heat and high melting point. The thickness of target layer 129 is preferably selected to correspond with the distance traveled in the material by electrons of the highest operating energy. In an alternative embodiment, a lesser thickness is preferably used for target layer 129. In the first described embodiment when the x-ray tube is operated at the low end of its operating range, for example 70 kV, electrons which strike the target will not fully penetrate target layer 129, and the x-rays generated will then be attenuated as they pass through the remainder of the target layer 129. For a fixed electron beam power the x-ray flux at 70 kV is about 30% of that at 100 kV so it is desirable to choose the thickness of target layer 129 based on the range of electrons in that material at 70 kV in order to maximize the x-ray flux at 70 kV while accepting a slightly lower electron beam power to x-ray flux conversion efficiency at 100 kV. The conversion efficiency at 100 kV will nevertheless be greater than that at 70 kV.

Beryllium is presently preferred for target support 130 because it possesses relatively high thermal conductivity and it combines a low attenuation for x-rays with the high mechanical strength required to minimize the mechanical deflection of target support 130 caused by atmospheric and coolant pressures. The thickness of target support 130 is preferably about 0.5 cm.

Collimation grid 90 preferably comprises a circular array, 25.4 cm (10 in) in diameter of regularly spaced vertical columns and horizontal rows of apertures 140 with 166 apertures in both vertical and horizontal diameters. The total number of apertures 140 in collimation grid 90 is preferably about 21,642. The axis of each aperture 140 points towards the center of multi-element detector array 100 (FIG. 1). While x-rays generated from focal spot 60 travel in all directions, collimation grid 90 provides a barrier which attenuates all those not directed towards detector array 110. The preferred collimation grid with alternative embodiments is described more fully in copending patent application Ser. No. 08/386,861, which has been incorporated herein by reference in its entirety.

A cooling chamber 350 is preferably disposed between target 50 and collimation grid 90. Cooling chamber 350 is preferably 0.2 cm thick and may be adapted to carry water, forced air or other types of cooling fluid. The presently preferred coolant is a liquid Fluorinert™ which is available from 3M Corporation. The coolant flows through cooling chamber 350 to absorb the heat dissipated by electron beam 40 as it strikes target 50. The coolant then passes through an external heat exchanger where it is cooled before being recirculated to cooling chamber 350.

FIG. 4 is an exploded view of the components of high voltage terminal assembly 803. As described more fully in connection with FIG. 2, an approximate −70 kV to −120 kV potential is preferably applied to high voltage terminal assembly 803 through spring 152, which is fitted into an indentation in the outer side of high voltage terminal endplate 154. Circuit board 214 preferably contains the fiber optic communication circuits for the components of high voltage terminal assembly 803. Eight fiber optic communications cables are preferably connected to circuit board 214 through a plug-in feedthrough assembly 166 in high voltage terminal endplate 154. The preferred fiber optic communications circuits are described more fully in copending patent application Ser. No. 08/386,861, which has been incorporated herein by reference in its entirety.

Because of the high voltage potential applied to the high voltage terminal assembly 803, an isolation transformer 744 is preferably employed to supply power to the components within the high voltage terminal assembly 803. The secondary coil assembly 1271 of isolation transformer 744 is affixed to aluminum cylinder ring 226, which is shown bolted to the high voltage terminal endplate 154 and circuit board housing 212. A flat washer of conducting silicone rubber 288 is preferably compressed between one end of secondary coil assembly 1271 and the high voltage terminal endplate 154, providing electrical conductivity between the two components. Similarly, another flat washer of conducting silicone rubber 290 is preferably compressed between the end of secondary coil assembly 1271 and the circuit board housing 212 to provide electrical conductivity between these two components. Circuit board housing 212 preferably comprises a deep drawn aluminum can with a large diameter axial hole formed in the can end plate. Contained within circuit board housing 212 is a circuit board stack comprising three circuit boards 206, 208 and 210. Circuit boards 206, 208 and 210 preferably contain all the electrical components which are necessary for operation of electron gun 198. Specifically these circuit boards preferably contain a low-voltage heater power supply, a −2 kV fixed power supply and a 0 to −2 kV variable-voltage power supply. Each circuit board is circular in shape and contains a solid "T" shaped aluminum heat sink 216 which protrudes from its surface. The circuit boards 206, 208 and 210 are bolted together to form a compact stacked assembly with electrical connection between each board achieved by means of mating connectors mounted on each board. The fiber optic circuitry located on circuit board 214 preferably connects to a connector on circuit board 210 via a ribbon cable which extends axially through the center of secondary coil assembly 1271 and through the hole in the end of circuit board housing 212. High voltage terminal support member 202 is fabricated from aluminum in a conical shape with a rear flange fitted with two groups of three threaded rods 204 diametrically opposed on the rear of the flange. The three circuit boards 206, 208 and 210 are shown mounted to support member 202 by inserting threaded rods 204 through holes located on heat sinks 216. Circuit board housing 212 slides over circuit boards 206, 208 and 210 so that threaded rods 204 protrude through holes in the end of circuit board housing 212. Circuit boards 206, 208 and 210 are thus shielded from the effects of the intense electric field which exists on the external surface of circuit board housing 212. The assembly comprising circuit boards 206, 208, 210 together with circuit board housing 212 are preferably held together by nuts applied to the ends of threaded rods 204. Referring to FIG. 2, high voltage terminal support member 202 is preferably bolted to flange 224 on electron gun 198.

Referring to FIG. 4, electron gun 198 is preferably mounted within the frontal aperture of high voltage terminal support member 202. Referring to FIG. 2, a metal sleeve is preferably mounted within the central aperture of ceramic disc 128, and welded to this metal sleeve is a flanged vacuum tube 221. Flange 224 on electron gun assembly 198 is shown bolted to the flanged section of vacuum tube 221 with an intermediate copper gasket which provides a seal between the $SF_6$ contained in electron beam source 112 and the high vacuum in vacuum envelope assembly 176. This arrangement allows for a simplified procedure for replacement of electron gun 198. Feedthrough leads 222 on electron gun assembly 198 pass through ceramic insulating disc 218 to make connection to the internal electrodes of electron gun 198.

Electron gun 198 preferably comprises a heater coil embedded in electron-emitting cathode 220, with cathode 220 mounted behind control grid 200. The entire electron gun structure is preferably supported from the feedthrough leads 222 on the vacuum envelope assembly 176 side of ceramic disc 218. Feedthrough leads 222 also provide electrical connecting means to the electrodes within the structure of electron gun 198. The presently preferred cathode 220 is a cylindrical piece of porous tungsten impregnated with low work-function materials which readily emit electrons. Such cathodes are known as dispenser cathodes and are available from Spectromat Inc. Employment of an impregnated tungsten cathode permits the use of a small diameter cathode since the electron beam current density obtainable from such a cathode is substantially higher than that from a pure metal emitter such as a tungsten filament. Because the focal spot 60 is preferably small, the electron source is also preferably small. The embedded heater coil is energized by an electric current generated by a low-voltage heater power supply within high voltage terminal assembly 803 which flows through two of the feedthrough leads 222. The heater coil preferably raises the temperature of cathode 220 to approximately 1100° C., which is the temperature at which the preferred cathode 220 emits the required electron beam current. These electrons are accelerated to an energy between 70 keV and 120 keV in the gap between electron gun 198 and anode 184 by the action of the negative high voltage applied to electron gun 198.

Control grid 200 preferably comprises a cylindrical electrode surrounding cathode 220 with an apertured end plate positioned slightly in front of the surface of cathode 220. The electron beam 40 emitted from cathode 220 can be varied in intensity by the application of a voltage to control grid 200, such voltage being of negative polarity with respect to cathode 220. In the preferred embodiment, application of −2 kV from a fixed potential power supply in high voltage terminal assembly 803 through feedthrough leads 222 to control grid 200 completely inhibits the flow of electron beam 40. Application of a variable potential in the range 0 to −2 kV to control grid 200 from a variable voltage power supply in high voltage terminal assembly 803 varies the intensity of electron beam 40 over the range of 0 to 60 mA. X-ray source 10 is preferably operated in a pulsed mode such that electron beam 40 is pulsed on rapidly for a time period relating to the electron beam scanning mode. This is preferably achieved by means of two solid state switching circuits contained within the circuit boards 206, 208 and 210. Each switching circuit preferably comprises a series-connected string of field effect transistors which can be turned on and off by means of command signals conveyed through fiber optic cables 168.

Figure 5:
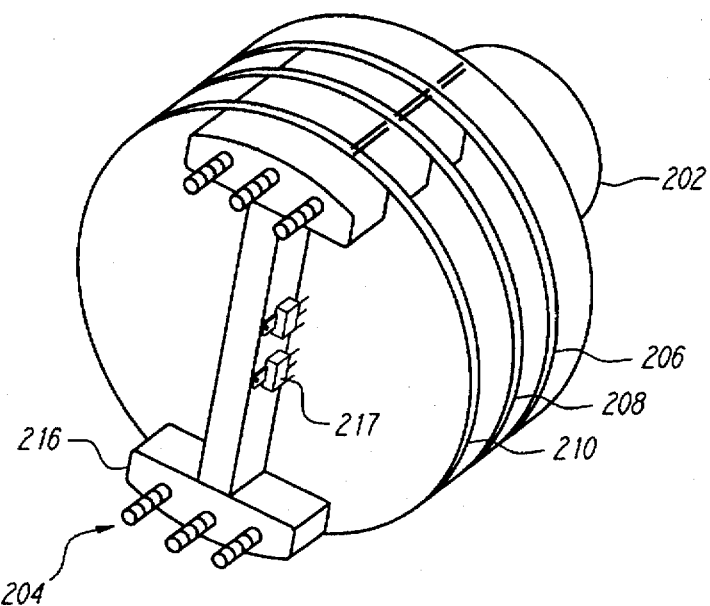
FIG. 5 is a perspective view of a preferred circuit board assembly.

Referring to FIG. 5, the components in circuit boards 206, 208 and 210 which generate heat, such as power transistors and voltage regulator components 217, are preferably attached to heat sinks 216. The three circuit boards are stacked and heat sinks 216 are clamped together by means of threaded rods 204. Heat dissipated in heat sinks 216 by components 217 is preferably conducted to high voltage terminal support member 202. Most of the heat will then be removed by convection of the $SF_6$ gas and thence to the outer walls of electron beam source 112. $SF_6$ gas under pressure is the preferred heat exchange medium and natural convection forces are enhanced by circulation of the gas caused by the high electric field. Some of the heat from terminal support member 202 will also be removed by conduction through ceramic disk 128.

Figure 6:
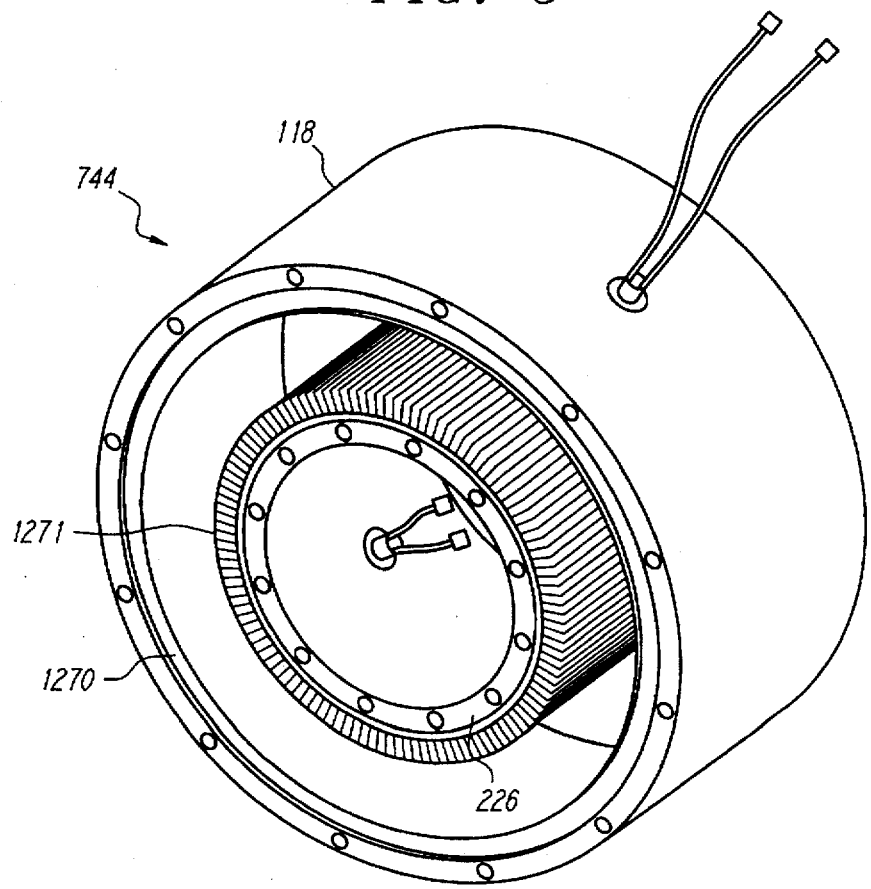
FIG. 6 is a perspective view of a preferred isolation transformer.

FIG. 6 is perspective diagram of a preferred isolation transformer 744, which supplies power for the components within high voltage terminal assembly 803. The secondary coil assembly 1271 of isolation transformer 744 is preferably located within high voltage terminal assembly 803. Because of the high voltage applied to high voltage terminal assembly 803, the primary coil assembly 1270 of preferred isolation transformer 744 is disposed coaxially around the secondary coil assembly 1271, physically separated from the secondary coil assembly 1271 by a distance of approximately 4 cm(1.6").

Isolation transformer 744 preferably operates at a frequency of 60 kHz although other operating frequencies can be employed. The potential at the secondary coil is preferably 30V R.M.S. In the preferred embodiment, both the primary coil assembly 1270 and the secondary coil assembly 1271 each have a ferromagnetic core. The preferred material for the ferromagnetic cores is ferrite, chosen for its low loss properties when operating at 60 kHz, although other low loss materials such as compressed powdered iron can also be employed. Isolation transformer 744 preferably operates with both primary and secondary coils resonant at the operating frequency by means of low loss capacitors connected across the coil connections. This improves the coupling between primary and secondary coils and eliminates the need for the 60 kHz power source to provide the out-of-phase magnetizing current. The resonating capacitors have a capacity of approximately 0.1 μF each.

The ferromagnetic core of secondary coil assembly 1271 is preferably formed of a cylinder of ferrite material. In the preferred embodiment, to reduce cost, the core is formed from a series of ferrite bars 230, preferably numbering twenty, with each bar abutting neighboring bars effectively forming a cylinder of ferrite within secondary coil 234.

Figure 7:
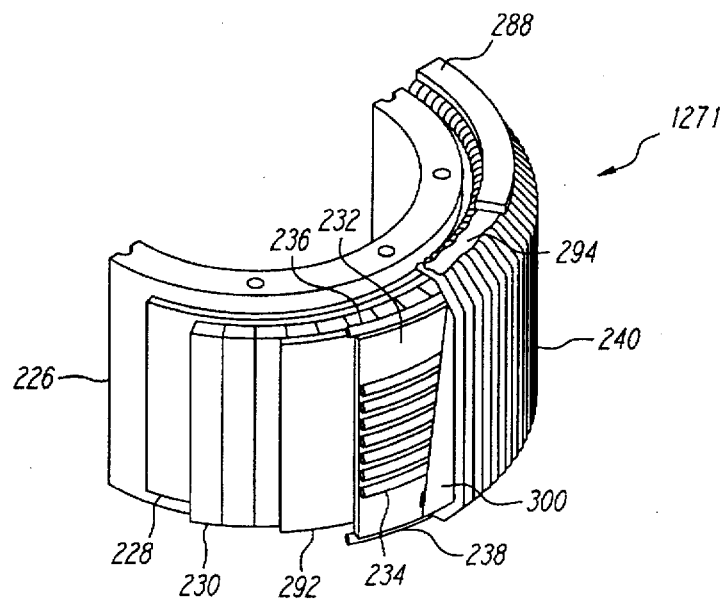
FIG. 7 is a diagram of a representative inner structure of a preferred isolation transformer secondary assembly.

As shown in FIG. 7, cylindrical coil form 232 preferably encircles ferrite bars 230, which are attached to coil form 232 by means of double sided adhesive foam tape 292. Coil form 232 is preferably formed of acrylic plastic although other electrically insulating materials with adequate thermal properties could be employed. Copper wire, preferably low loss RF wire known as Litz wire, is wound around the central part of the outer face of coil form 232 to form the secondary coil 234. In the preferred embodiment, there are 13 turns of wire in secondary coil 234 although the preferred number of turns is not germane to the essence of the invention and the actual number of turns depends on the particular usage requirements of the transformer. The number of turns depicted in FIG. 7 for secondary coil 234 is for purposes of illustration only and should not be considered the number of turns actually employed in the present invention.

Copper rings 236 and 238 are preferably placed around both edges of coil form 232. The coil form 232 is preferably longer than ferrite bars 230 by a small amount, preferably about 0.2 cm (0.08"). Copper rings 236 and 238 form two short-circuited single-turn coils which completely encircle the upper and lower edges of coil form 232. In the preferred embodiment, copper rings 236 and 238 are formed from 0.125" OD copper tubing and have a diameter approximately equal to that of coil form 232. Copper rings 236 and 238 are attached to the upper and lower edges of coil form 232 by means of adhesive Kapton™ tape, available from Dupont. The entire assembly, comprising ferrite bars 230, coil form 232, copper rings 236 and 238, and the secondary coil 234 is then preferably wrapped toroidally with adhesive Kapton™ tape 300 to provide an electrically insulating protective barrier for secondary coil 234.

An electrostatic shield 240 is formed of insulated copper wire wound closely and toroidally around tape 300. The wire is preferably 24 AWG copper magnet wire. The top and bottom surfaces of shield wires 240 are preferably treated to remove the insulation and expose the bare copper. A bead of solder 294 is preferably applied circumferentially around the bare copper wire surfaces to provide an electrical connection between adjacent wires at the top and the bottom. A conducting silicone rubber washer 288, preferably 0.15 cm (0.060") thick, is preferably placed along the top surface of solder bead 294 and another identical washer of conducting silicone rubber 290 is preferably placed along the bottom solder bead.

Aluminum ring 226, containing bolt holes along the upper and lower edges, is preferably attached to the inner surface of secondary coil assembly 1271 by silicone rubber 228. Secondary coil assembly 1271 is attached to the rest of high voltage terminal assembly 803 by bolting aluminum ring 226 to circuit board housing 212 and the high voltage terminal endplate 154 (FIG. 4). Conducting silicone rubber washers 288 and 290 are preferably compressed between the secondary coil assembly 1271 and the high-voltage terminal endplate on one end, and the circuit board housing 212 on the other end, providing electrical conductivity between these components.

Figure 8:
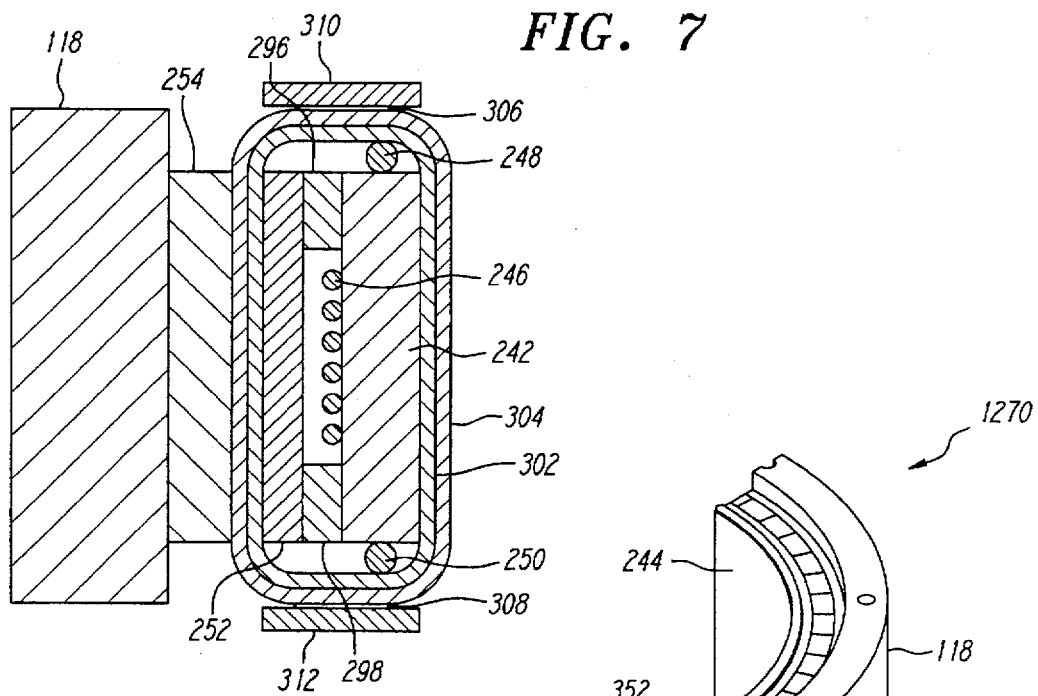
FIG. 8 is a cross-sectional view of a preferred isolation transformer primary assembly.

Cylindrical coil form 242 is the innermost layer of primary coil assembly 1270, as shown in FIG. 8. Coil form 242 is preferably formed of acrylic plastic although other electrically insulating materials with adequate thermal properties could be employed. Copper wire, preferably low loss RF wire known as Litz wire, is wound around the central part of the outer face of coil form 242 to form the primary coil 246. In the preferred embodiment there are 11 turns of wire in primary coil 246 although the number of turns is not germane to the essence of the invention and the actual number of turns depends on the particular usage requirements of the transformer. The number of turns depicted in FIG. 8 for primary coil 246 is for purposes of illustration only and should not be considered the number of turns actually employed in the present invention.

Double sided adhesive foam tapes 296 and 298 are attached circumferentially to the upper and lower extremities of the outer face of coil form 242. Preferably attached to the outside of double sided adhesive foam tapes 296 and 298 is the primary coil ferromagnetic core material. In the preferred embodiment, the ferromagnetic core comprises a series of ferrite bars 252, preferably numbering 37, with each bar abutting neighboring bars effectively forming a cylinder of ferrite outside primary coil 246.

Copper rings 248 and 250 are preferably placed around both edges of coil form 242. Coil form 242 is preferably longer than ferrite bars 252 by a small amount, preferably about 0.2 cm (0.08"). Copper rings 248 and 250 form two short-circuited single turn coils which completely encircle the upper and lower edges of coil form 242. In the preferred embodiment, copper rings 248 and 250 are formed from 0.125" OD copper tubing and have a diameter approximately equal to that of coil form 242. Copper rings 248 and 250 are attached to the upper and lower edges of coil form 242 by means of adhesive Kapton™ tape. The entire assembly, consisting of ferrite bars 252, coil form 242, copper rings 248 and 250, and the primary coil 246 is then preferably wrapped toroidally with adhesive Kapton™ tape 302 to provide an electrically insulating barrier for primary coil 246.

An electrostatic shield 304 is preferably formed of insulated copper wire wound closely and toroidally around tape 302. The wire is preferably 24 AWG copper magnet wire. The top and bottom surfaces of shield wires 304 are treated to remove the insulation and expose the bare copper. Beads of solder 306 and 308 are then applied circumferentially around the bare copper wire surfaces to provide an electrical connection between adjacent wires at the tope and the bottom. A conducting silicone rubber washer 310, preferably 0.15 cm (0.060") thick, is placed along the top surface of solder bead 306 and a similar washer of conducting silicone rubber 312 is placed along the bottom solder bead 308.

The outer face of primary coil assembly 1270 is preferably affixed to central aluminum cylinder 118 with silicone rubber 254. Aluminum cylinder 118 contains bolt holes along its upper and lower edges and bolts to flanged aluminum cylinders 114 and 116 to form the outer wall of electron beam source 112. Conducting silicone rubber washers 310 and 312 are preferably compressed between the flanged portions of aluminum flanged cylinders 114 and 116 along both the top and bottom edges of primary coil assembly 1270. Conducting silicone rubber washers 310 and 312 thereby provide an electrically conductive path between flanged aluminum cylinders 114 and 116 and electrostatic shield 304.

Figure 9:
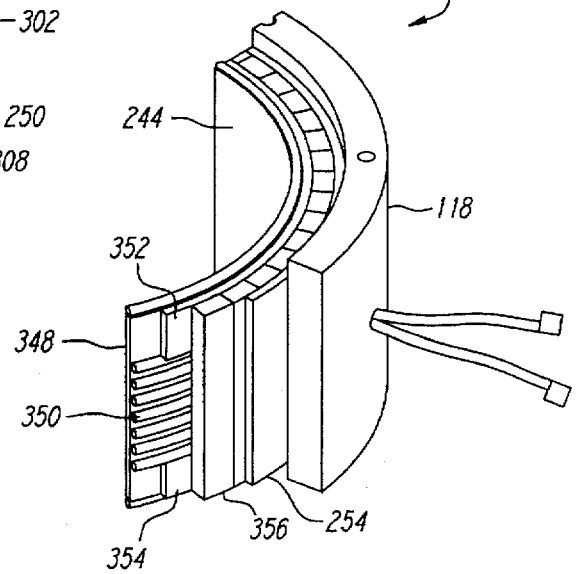
FIG. 9 is a diagram of a representative inner structure of an alternately preferred isolation transformer primary assembly.

Referring to FIG. 9, an alternative embodiment of primary coil assembly 1270 is shown. Like the preferred embodiment of FIG. 8, a cylindrical acrylic plastic coil form 348 preferably forms the inner structure of primary coil assembly 1270. Primary coil 350 is preferably wound around the outer face of coil form 348, preferably forming 11 turns.

Two bands of adhesive double backed tape 352 and 354 affix a series of ferrite bars 356 to the upper and lower outer circumference of coil form 348. The outer face of primary coil assembly 1270 is preferably affixed to central aluminum cylinder 118 using silicone rubber 254. The number of turns depicted in FIG. 9 is for purposes of illustration only.

The embodiment depicted in FIG. 9 employs an alternative electrostatic shield arrangement from that depicted in FIG. 8. This alternative electrostatic shield arrangement employs a resistive electrically conductive paint such as a colloidal graphite paint available from Acheson Colloids Inc., over the interior circumference 244 of coil form 348. As in the previous preferred embodiment, electrical connection to the graphite paint is made by conducting silicone rubber washers compressed against flanged aluminum cylinders 114 and 116.

Figure 10:
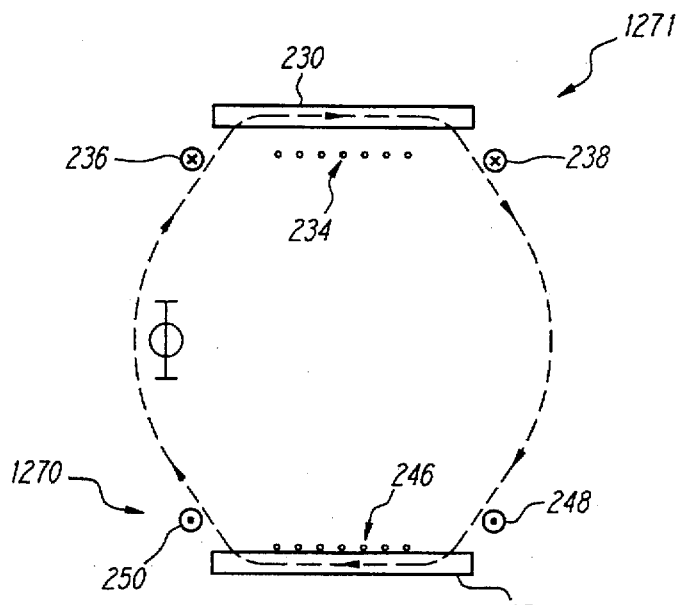
FIG. 10 is a diagrammatic representation of the magnetic field lines between the primary and secondary of the preferred isolation transformer.

FIG. 10 illustrates the typical path of magnetic field lines which couple primary coil assembly 1270 with secondary coil assembly 1271 in the preferred isolation transformer 744. As depicted, currents induced in the copper eddy current shield rings confine the magnetic field and minimizes coupling into the various support structures, thereby minimizing excessive power losses in those support structures. Unlike conventional power transformers, magnetic field containment is achieved without a ferromagnetic return circuit.

As shown in FIG. 10 the preferred isolation transformer 744 substantially confines the magnetic flux $\Phi$ within the area defined by ferrite bars 230 and 252 and the copper rings 236, 238, 248 and 250. Ferrite bars 230 and 246, by virtue of their high permeability, provide a low reluctance path for the magnetic field so that the field travels preferentially in the ferrite bars rather than in the material on either side of the ferrite bars.

Eddy current shield rings 236, 238, 248 and 250 function as magnetic field clamps, substantially confining the magnetic flux $\Phi$ within the boundaries shown in FIG. 10. This field clamping occurs because the magnetic flux $\Phi$ induces eddy currents in the copper rings which in turn generate opposing magnetic fields which effectively "push in" magnetic flux field lines to within the above stated boundaries. Thus the typical path followed by magnetic flux $\Phi$ will extend from ferrite bar 252 towards ferrite bar 230 and will be curved with a bulge midway between copper rings 250 and 236 then returning from ferrite bar 230 towards ferrite bar 252 in a similar shaped path between copper rings 238 and 248. The ferrite bars together with the eddy current shield essentially function as a magnetic return circuit while maintaining physical separation between the primary coil assembly 1270 and the secondary coil assembly 1271.

Two deflection yokes, fast yoke 188 and slow yoke 190 are preferentially employed to move electron beam 40 in the required scan pattern over the surface of target 50. Slow deflection yoke 190 preferably comprises saddle type X and Y deflection coils wound within the internal slots of a ferrite cylinder. Such a construction technique has been used for the deflection yokes used with television picture tubes. FIG. 11 shows a diagrammatic representation of a preferred fast deflection yoke 188. In FIG. 11, the x axis is defined as horizontal and the y axis is defined as vertical when FIG. 11 is viewed in its correct orientation. Y-step deflection coils 265 and 266 and X-step deflection coils 268 and 270 are toroidally wound with copper magnet wire in internal slots formed on the inside diameter of ferrite ring 286. The coils of fast deflection yoke 188 are preferably wound with fewer turns than the coils of slow deflection yoke 190 thus ensuring that the coils of fast deflection yoke 188 have substantially lower self inductances in comparison with those on slow deflection yoke 190. This lower self inductance of the coils on fast deflection yoke 188 makes it possible to effect small fast step changes in the amplitudes of the currents flowing in coils 265, 266, 268 and 270 with resultant rapid step changes in the position of electron beam 40 on target 50. The preferred circuitry to control and drive the current in the coils of the fast and slow deflection yokes are discussed more fully in the more detailed explanation of FIGS. 16–25, which are set forth below. The number of turns depicted in FIG. 11 is for purposes of illustration only and should not be considered the preferred number of turns.

The deflection of electron beam 40 by deflection yokes 188 and 190 results in aberrations from ideal performance which increase in effect as the deflection angle of electron beam 40 increases. These aberrations cause focal spot 60 to depart from circularity as its distance from the center of target 50 increases. 45° stigmator coil 784 and 0° stigmator coil 786 are preferably employed to correct these aberrations. Currents supplied from an external source pass through stigmator coils 784 and 786 to modify the deflecting magnetic field configuration. The amplitudes and directions of these currents is programmed to maintain a circular shape for focal spot 60 as it scans over the face of target 50. 45° stigmator coil 784 and 0° stigmator coil 786 are preferably wound toroidally around ferrite ring 286 at the 0° and 45° positions. The preferred circuits employed to control and drive the current in 45° stigmator coil 784 and 0° stigmator coil 786 are discussed more fully in the more detailed explanation of FIGS. 16–25, which are set forth below.

Figure 13:
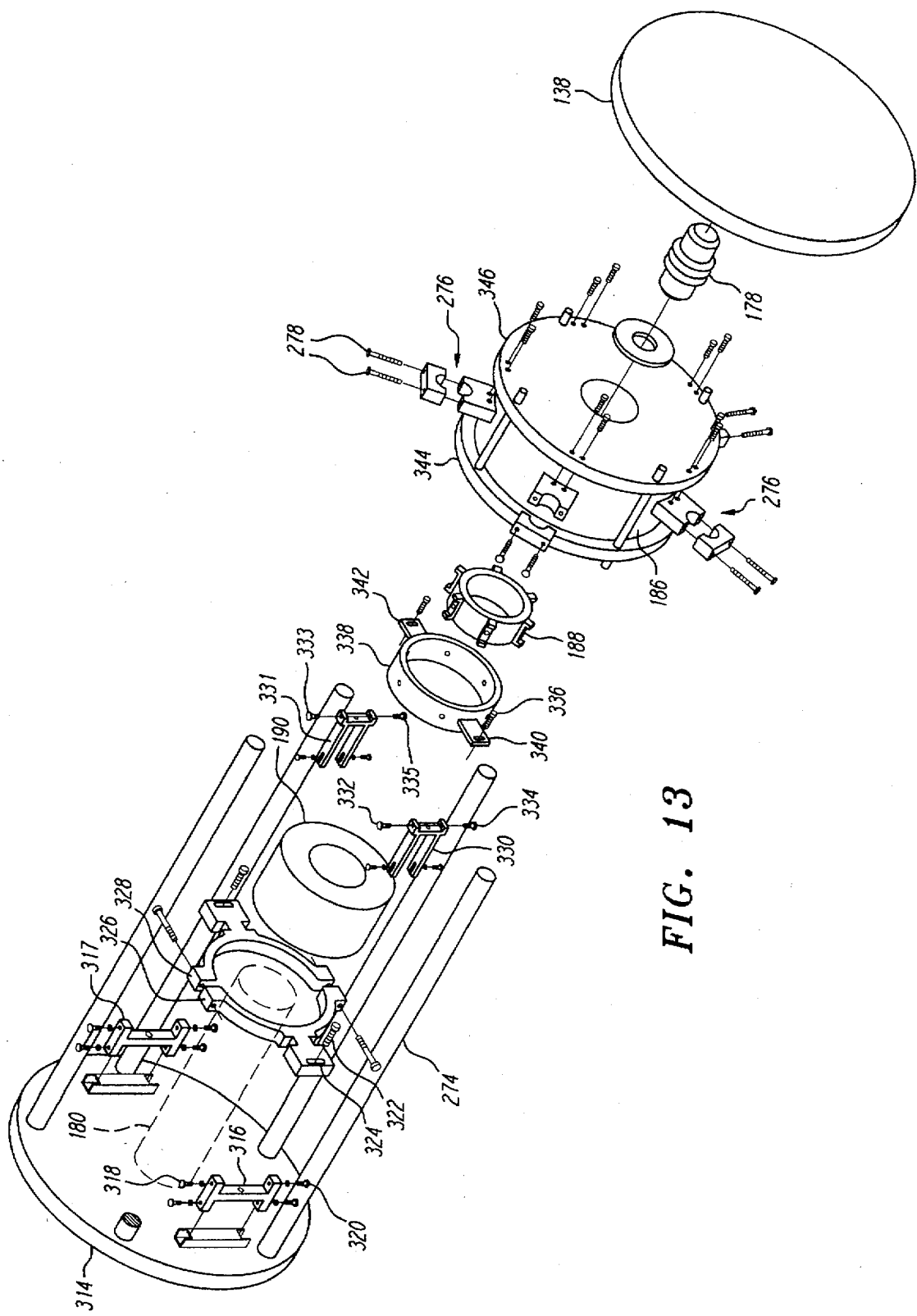
FIG. 13 is an exploded view of the deflection yoke and focus coil alignment structures of FIG. 14.

Referring to FIGS. 12 and 13, means are provided to rotationally adjust the axes of the deflection yokes such that they are properly aligned in relation to the apertures of the collimation grid 90. Endplate 314, which is rigidly attached to the end bell assembly 266, contains two rotational support members 316 and 317 along its outer face, one on either side of the slow yoke 190. Rotational support member 316 contains a C-shaped section with an adjustment screw 318 inserted through the upper portion and adjustment screw 320 inserted through the lower portion of the C-shaped section.

Slow yoke 190 is clamped between two identical alignment-clamps 326 and 328. Alignment-clamp 326 contains a flat rectangular tongue which extends outward between the upper and lower C-shaped portions of the rotational support member 316. Locking screw 322 extends through a groove 324 in the alignment-clamp tongue into a mating hole in the rotational support member 316. The adjustment screws 318 and 320 tighten to form contact with the upper and lower surfaces of the alignment-clamp tongue. A similar assembly exists on the other side of slow yoke 190 with respect to the other alignment-clamp 328. To effect the rotational adjustment of the slow yoke 190, locking screw 322 on alignment-clamp 326 and a similar locking screw on alignment-clamp 328 are loosened to allow free rotational movement of the Alignment-clamps 326 and 328. Adjustment screws 318 and 320, along with similar adjustment screws for alignment-clamp 328, are then adjusted to rotationally position the alignment-clamps 326 and 328, thereby effecting a corresponding rotational adjustment for the slow yoke 190 around the central ceramic cylinder 180.

A rotational support member 330 containing two rectangular protrusions extends and attaches through upper and lower rectangular grooves in alignment-clamps 326. Rotational support member 330 contains a C-shaped section with an adjustment screw 332 inserted through the upper portion and adjustment screw 334 inserted through the lower portion of the C-shaped section. A similar rotational support member 331 and locking screws 333 and 335 extend and attach to the other alignment-clamp 328.

Cylinder ring 338, which has the fast yoke 188 mounted along its interior surface, is formed with two rectangular adjustment plates 340 and 342 along its exterior surface. Rectangular adjustment plate 340 extends outward between the upper and lower C-shaped portions of the rotational support member 330. Locking screw 336 extends through a groove in the adjustment plate 340 into a mating hole in the rotational support member 330. The adjustment screws 332 and 334 tighten to form contact with the upper and lower surfaces of the adjustment plate 340. Adjustment plate 342 is similarly positioned between the upper and lower C-shaped portions of rotational support member 331. To effect the rotational adjustment of the fast yoke 190, locking screw 336 on adjustment plate 340 and a similar locking screw on the other adjustment plate 342 are loosened to allow free rotational movement of the cylinder ring 338. Adjustment screws 332 and 334, along with similar adjustment screws 333 and 335 for adjustment plate 342 are then adjusted to rotationally position the cylinder ring 338, thereby effecting a corresponding rotational adjustment of the attached fast yoke 188 around the central ceramic cylinder 180.

The magnetic focus lens assembly 186 can be positioned axially along the length of the vacuum envelope assembly 176 to regulate the minimum electron beam spot size on the target 50. Such positioning can prevent damage to the target 50 from minimum electron beam spot sizes which are overly concentrated, which may burn the target 50. Positioning rod 274 extends from front endplate 138 to an endplate 314, which is rigidly attached to the end bell assembly 266. Five such positioning rods are preferably disposed equidistantly along the outside perimeter of the endplates 314 and 138. The magnetic focus lens assembly 186 is mounted between a front support plate 346 and a rear support plate 344. Preferably attached to the front support plate 346 are five rectangular clamps 276, each of which encircles a corresponding positioning rod 274. To position the focus coil structure 186, locking screws 278 on the clamps 276 are released allowing the focus coil structure to slide along the positioning rods 274. Once an optimal position is established, the locking screws 278 are tightened into a locking position.

Magnetic focus lens assembly 186 can be moved radially to align the central magnetic axis of focus lens assembly 186 with the central axis of electron beam 40 when electron beam 40 is not deflected by yokes 188 and 190. Alignment of focus lens assembly 186 is effected by means of 4 set screws (not shown), which protrude radially from threaded holes in plate 346. The inner ends of these set screws push against the outer diameter of the U-shaped magnetic circuit member. Turning these screws causes the magnetic circuit member to move in any radial direction with respect to plate 346. For purposes of illustration only, magnetic focus lens assembly 186 is shown as a solid in FIG. 12.

As discussed previously, the electron beam 40 is moved across the face of the target 50 in a predetermined scan pattern. Because of the collimation grid 90 employed in the preferred scanning beam x-ray imaging system, the electron beam 40 is preferably scanned in a "step" pattern. This step pattern is used to direct electron beam 40 to a spot on the target 50 that is on the axis of a specified collimator grid aperture 140 for a designated period of time, and then to rapidly move the electron beam 40 to another spot on the target 50 directly on the axis of the next specified collimator grid aperture 140. Electron beam 40 rapidly moves to the next target location to maximize the useful x-ray flux emitted through the collimator aperture.

The electron beam 40 is directed in this step pattern by the fast deflection yoke 188 working in combination with the slow deflection yoke 190. Within the slow deflection yoke 190, the X and Y deflection coils function in a conventional manner to apply a varying magnetic field such that the electron beam 40 is scanned in a sweep pattern across the target 50. The width and height of the sweep pattern is regulated by the current pattern applied to the X and Y deflection coils.

Within the fast deflection yoke 188, the X-step and Y-step deflection coils 264, 266, 268, 270 apply a rapidly moving magnetic field to modify the magnetic field generated by the slow deflection yoke 190. The combination of the magnetic fields generated by the fast and slow deflection yokes are such that the electron beam 40 is deflected in a step pattern across the target 50. Fast deflection yokes 188 are preferably employed because conventional slow deflection yokes designed to sweep the electron beam typically require a large voltage in order to change its current fast enough to generate the necessary step pattern, particularly in the preferred embodiment of the present invention where the electron beam is preferably stepped behind an 166 by 166 array of apertures with a scanning frame rate of 30 Hz. The coils in the preferred fast deflection yokes 188 are wound with shorter lengths and fewer turns than the slow deflection yokes 190, allowing fast current changes.

Figure 14:
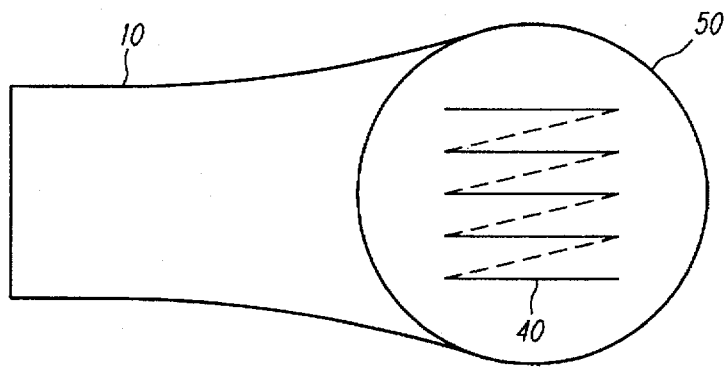
FIG. 14 is a diagram of a preferred x-ray tube scanning an electron beam in a raster scan pattern.

In a preferred embodiment, the electron beam 40 is deflected in a stepped raster scan pattern across the face of the target 50, as depicted in FIG. 14. The preferred method to deflect the electron beam 40 in a raster scan pattern is diagrammed in FIGS. 14A–F. FIGS. 14A depicts a sample linear pattern applied to the X-deflection coils 280 and 282, producing a conventional X sweep of the target 50 by the electron beam 40. FIG. 14C depicts the sawtooth pattern applied to the X-step deflection coils 264 and 266, which produces the resultant step pattern as shown in FIG. 14E when magnetically combined with the X deflection pattern of FIG. 14A.

Figure 14B:
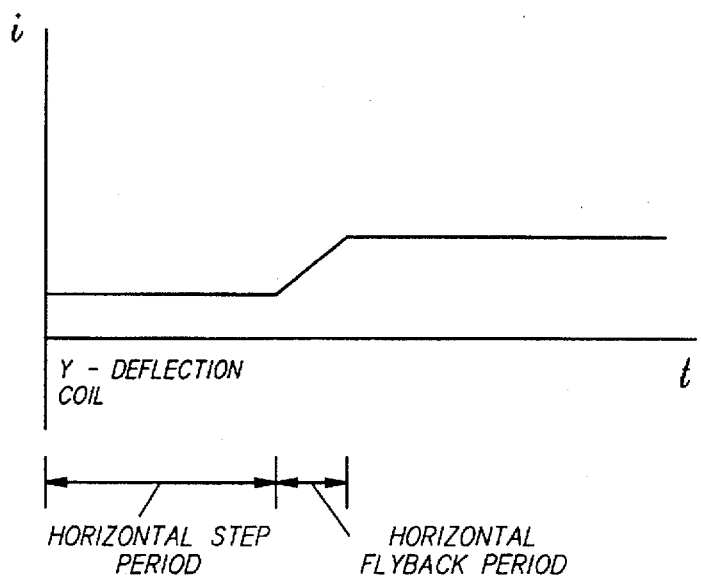
Figure 14D:
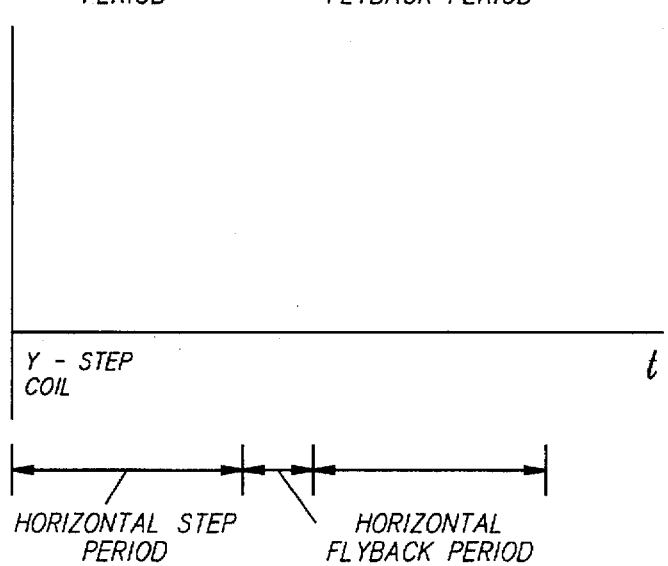
Figure 14F:
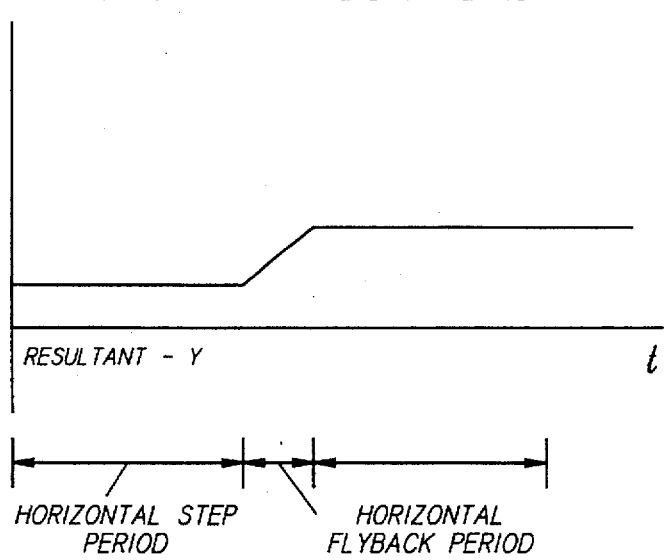

FIG. 14B depicts the pattern applied to the Y-deflection coils 276 and 278, to produce a conventional Y-sweep of the target 50 by the electron beam 40. As indicated in FIG. 14D, current is not applied to the Y-step deflection coils when scanning in the horizontal flyback mode since the period of time required for the electron beam 40 to "flyback" from the end of one horizontal row to the beginning of the next horizontal row gives the Y deflection coil sufficient reaction time to modify the current in its coil such that the electron beam is correctly deflected to the proper Y position.

Figure 15:
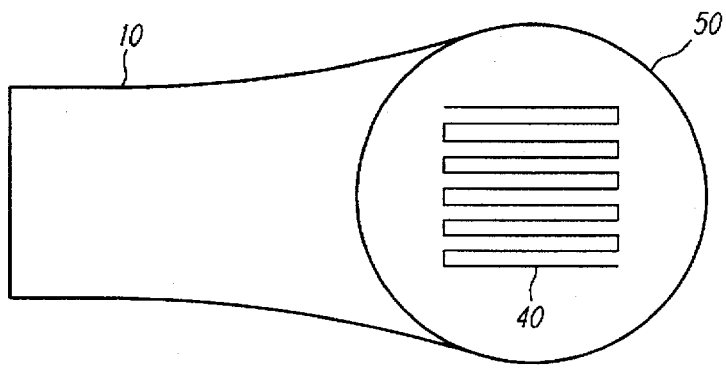
FIG. 15 is a diagram of a preferred scanning x-ray tube scanning an electron beam in a serpentine pattern.
Figure 15A:
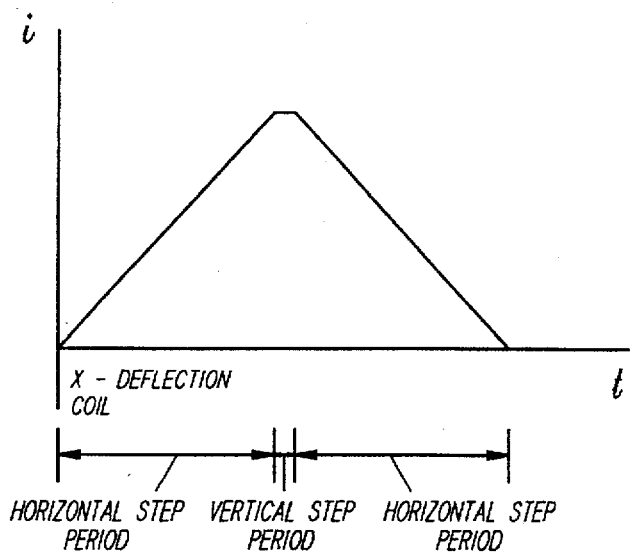
FIGS. 15A–G are graphical representations of the current applied to deflection coils to move an electron beam in serpentine pattern.
Figure 15C:
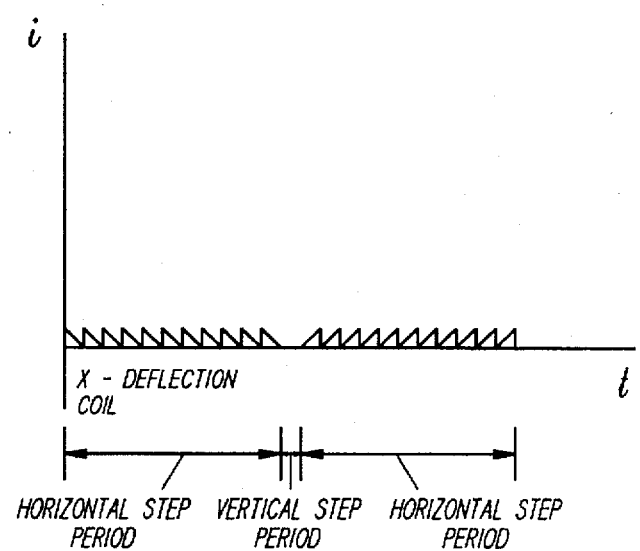
Figure 15E:
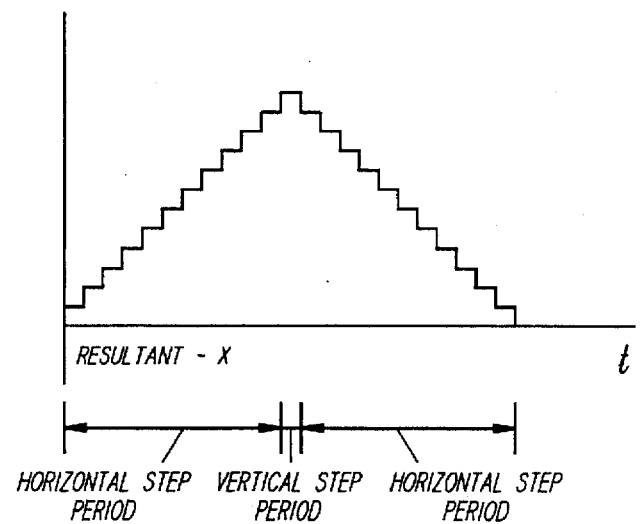

In an alternate embodiment, the electron beam 40 is deflected in a stepped serpentine pattern across the target 50, as depicted in FIG. 15. The preferred method to deflect the electron beam 40 in a stepped serpentine pattern is diagrammed in FIGS. 15A–F. FIGS. 15A diagrams a sample pattern applied to the X-deflection coils 280 and 282, producing an X sweep of the target 50 by the electron beam 40. FIG. 15C depict the sawtooht pattern applied to the X-step deflection coils, with a mirrored sawtooth pattern applied when the electron beam 40 begins scanning the next horizontal row, producing the resultant step pattern as shown in FIG. 15E when magnetically combined with the X deflection pattern of FIG. 15A. An alternate x-step pattern could comprise the use of a negative sawtooth pattern during the return horizontal step period, as shown in FIG. 15G.

Figure 15B:
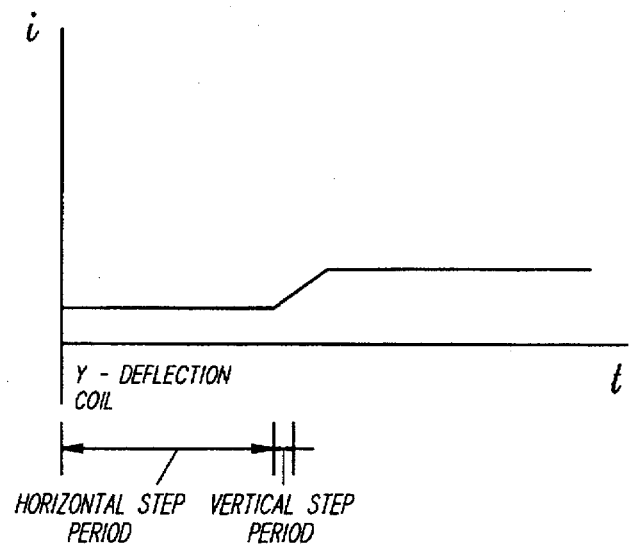
Figure 15D:
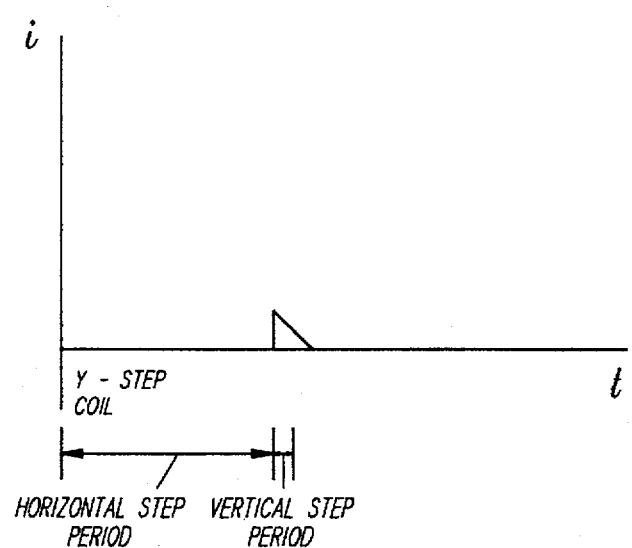
Figure 15F:
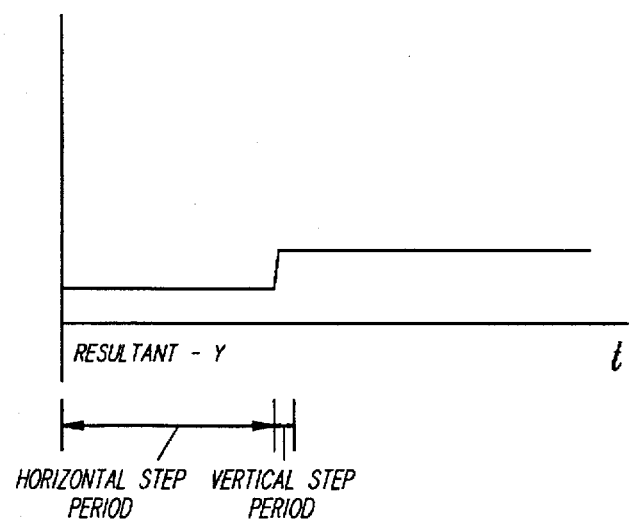
Figure 15G:
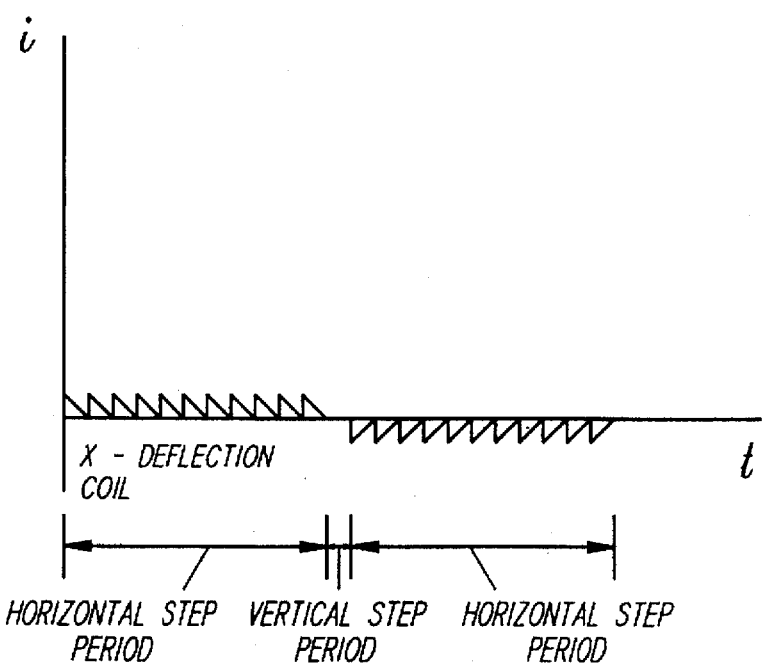

FIG. 15B depicts a sample current pattern applied to the Y-deflection coils 276 and 278, to produce a Y-sweep of the target 50 by the electron beam 40. The sawtooth Y-step pattern in FIG. 14D is applied when the scanning electron beam 40 reaches the end of a horizontal row, producing the resultant Y pattern shown in FIG. 14F when magnetically combined with the Y deflection coil pattern.

In another alternative embodiment, electron beam 40 is scanned in a stepped serpentine pattern as described in the previous embodiment but the Y-step coils are not used when the electron beam reaches the end of a horizontal row. The required y direction deflection of electron beam 40 is caused using the slow y coils in slow yoke 190. The greater time taken to achieve the step from row to row will typically result in a small reduction in efficiency of x-ray production.

The size and shape of the current patterns depicted in FIGS. 14A–F and 15A–F are shown for illustrative purposes only. The actual current patterns applied to the X and Y deflection coils and the X-step and Y-step deflection coils are dependant upon many factors, which may include the rate of movement of the electron beam, the amount of deflection already applied, the number of collimator apertures, the dwell time for each collimator aperture location, the number of turns for each coil, and the exact placement of the deflection coils.

Figure 16:
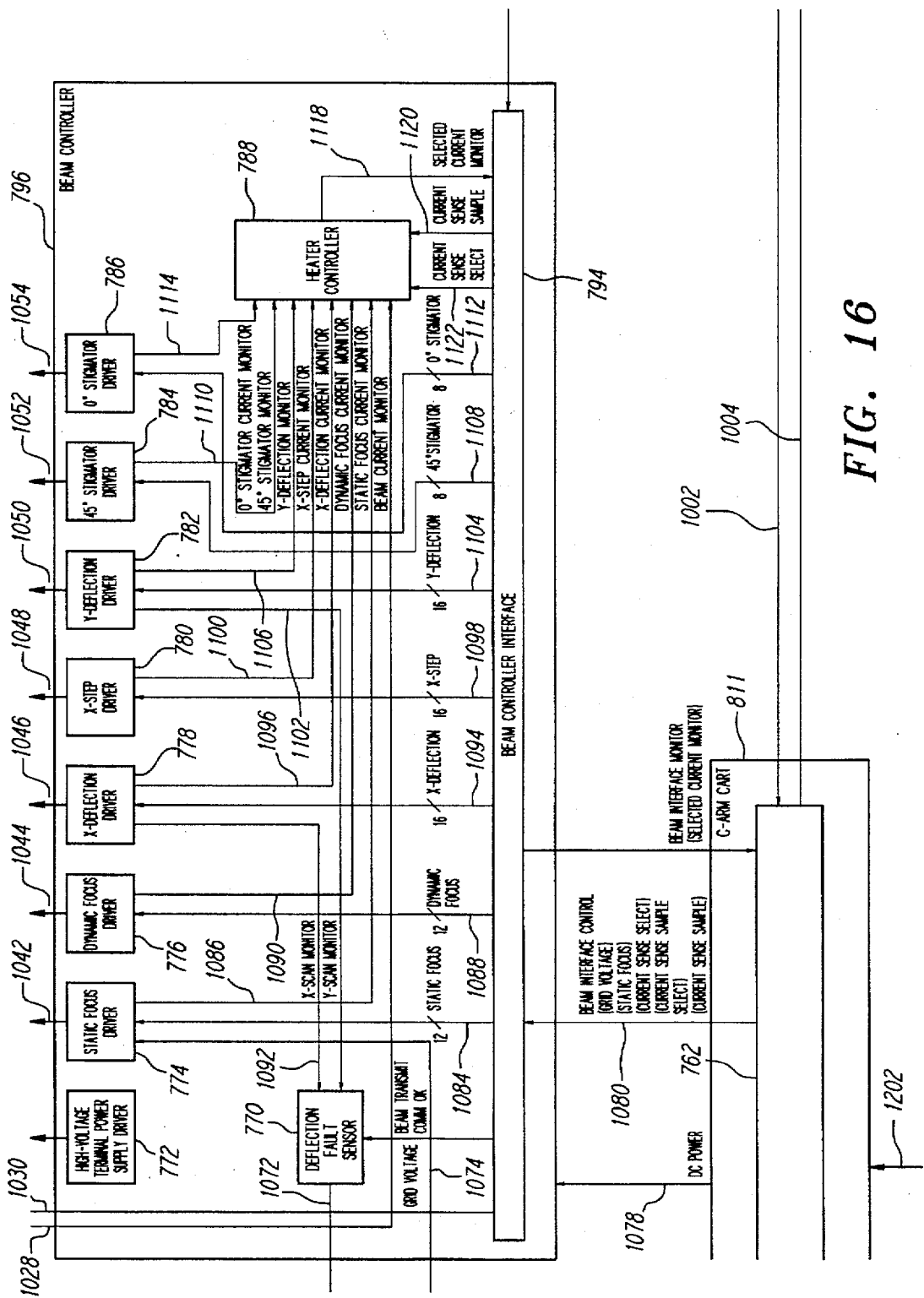
FIG. 16 is a partial functional block diagram showing a preferred scan generator for a scanning beam imaging system.
Figure 17B:
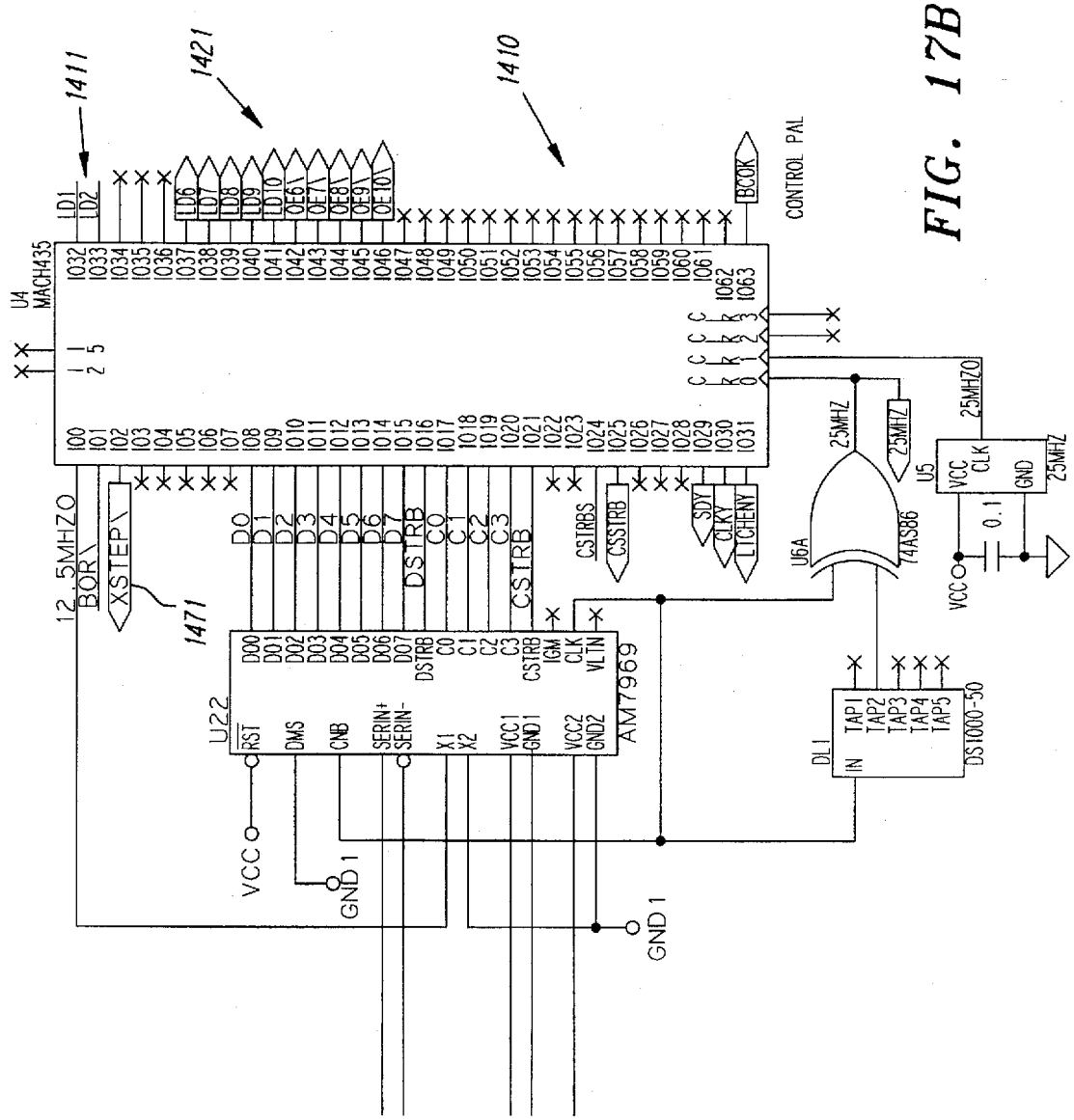
Figure 18:
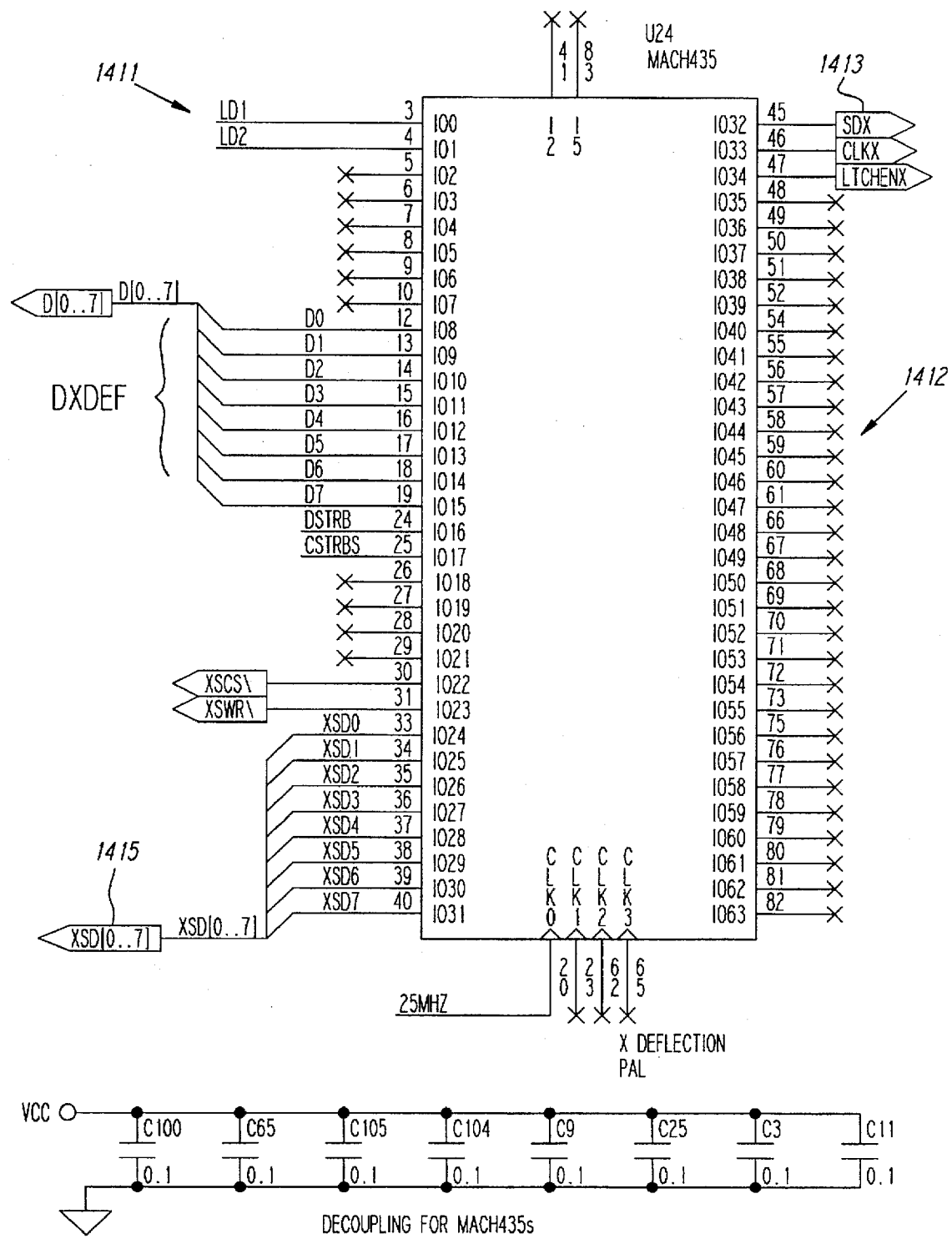
Figure 19A:
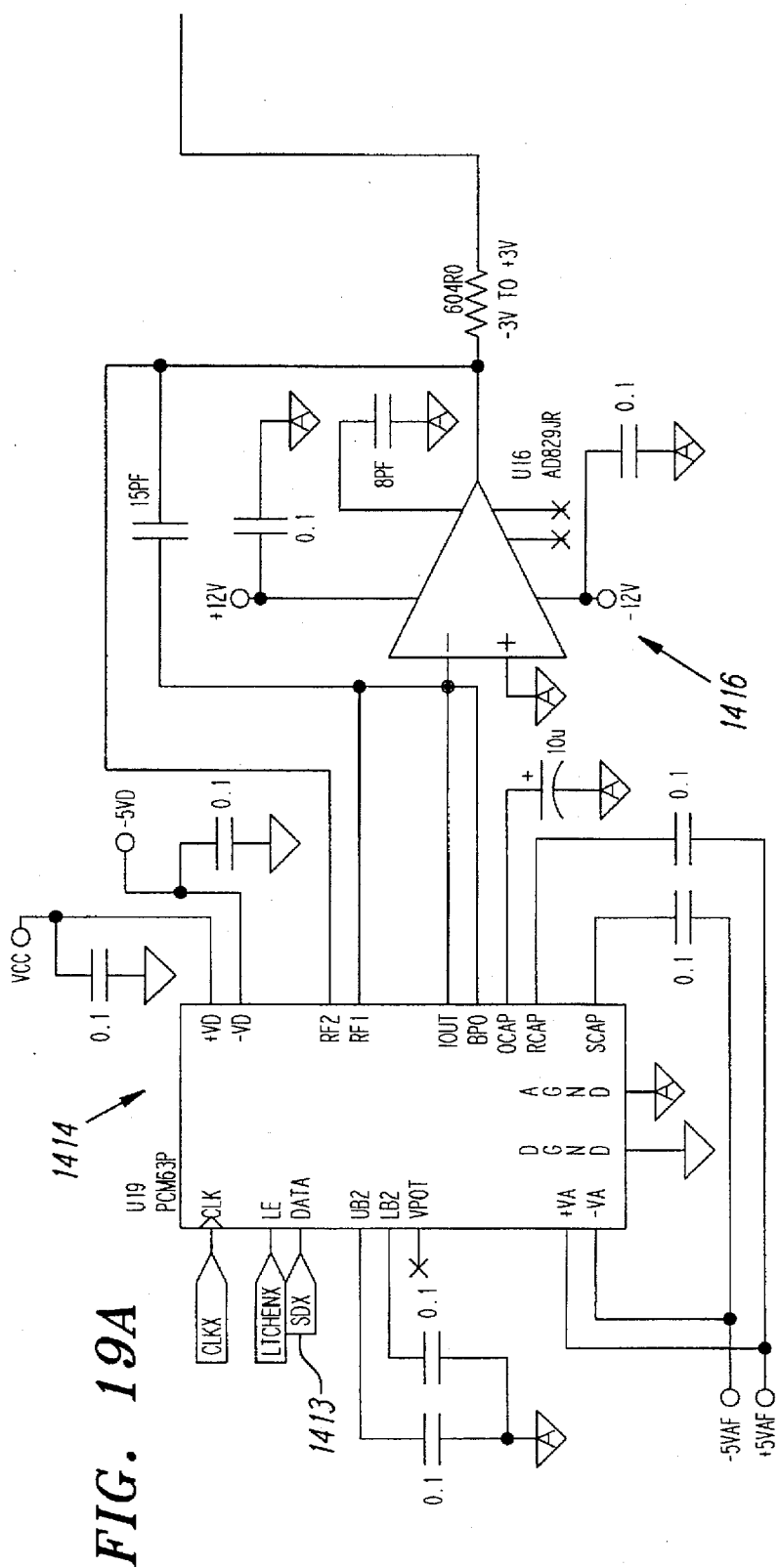
Figure 19C:
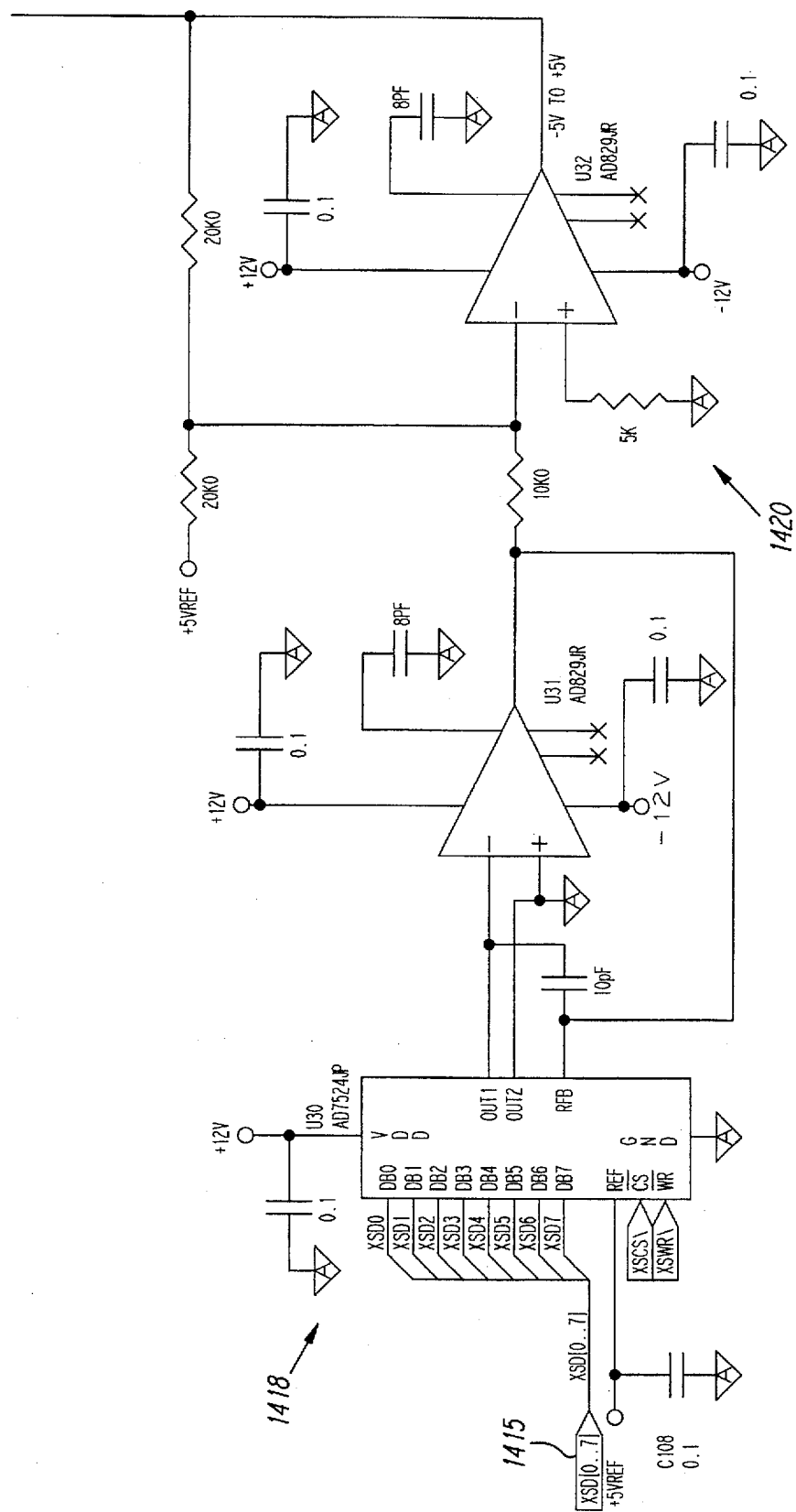
Figures 20, 20A:
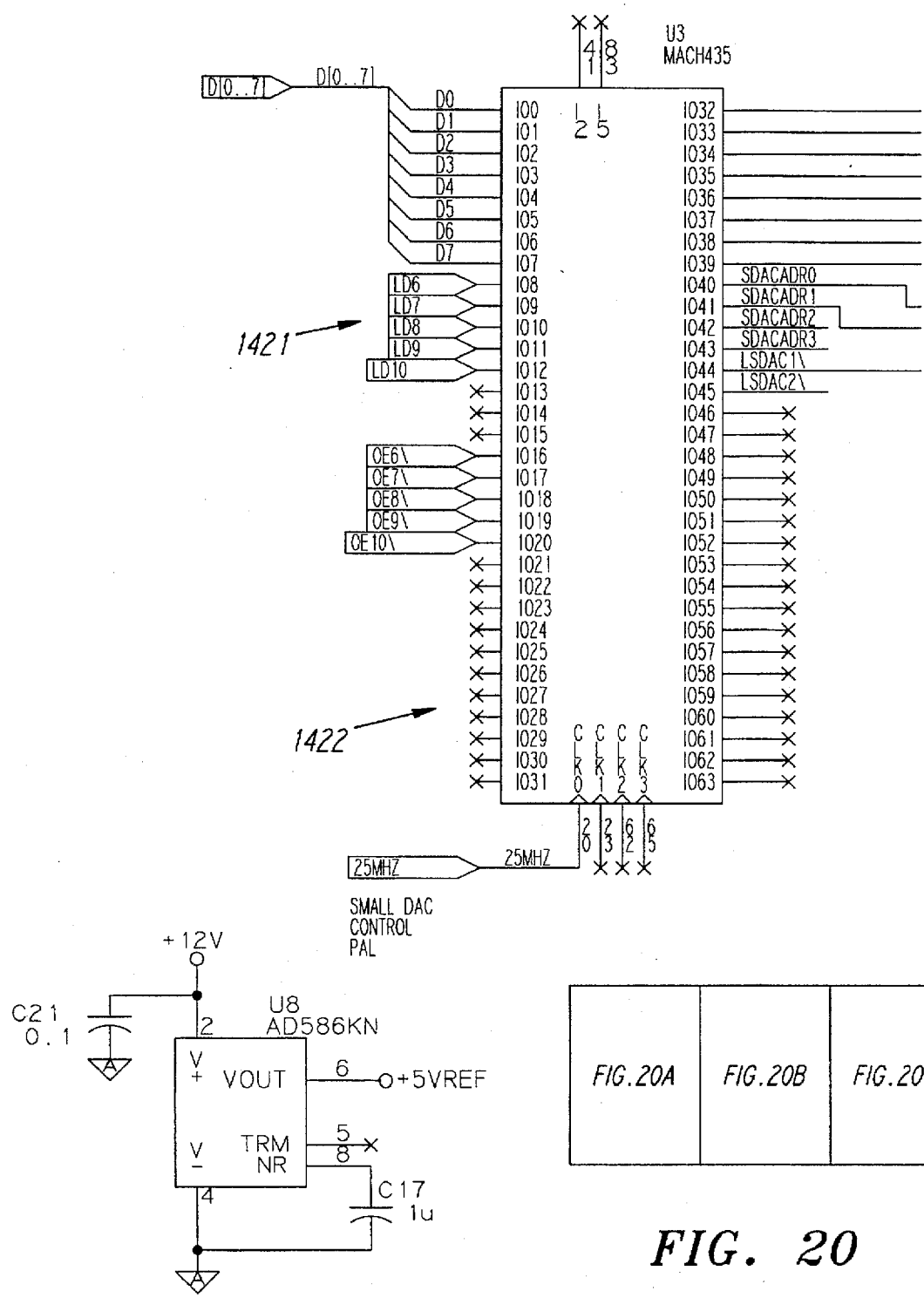
Figure 20B:
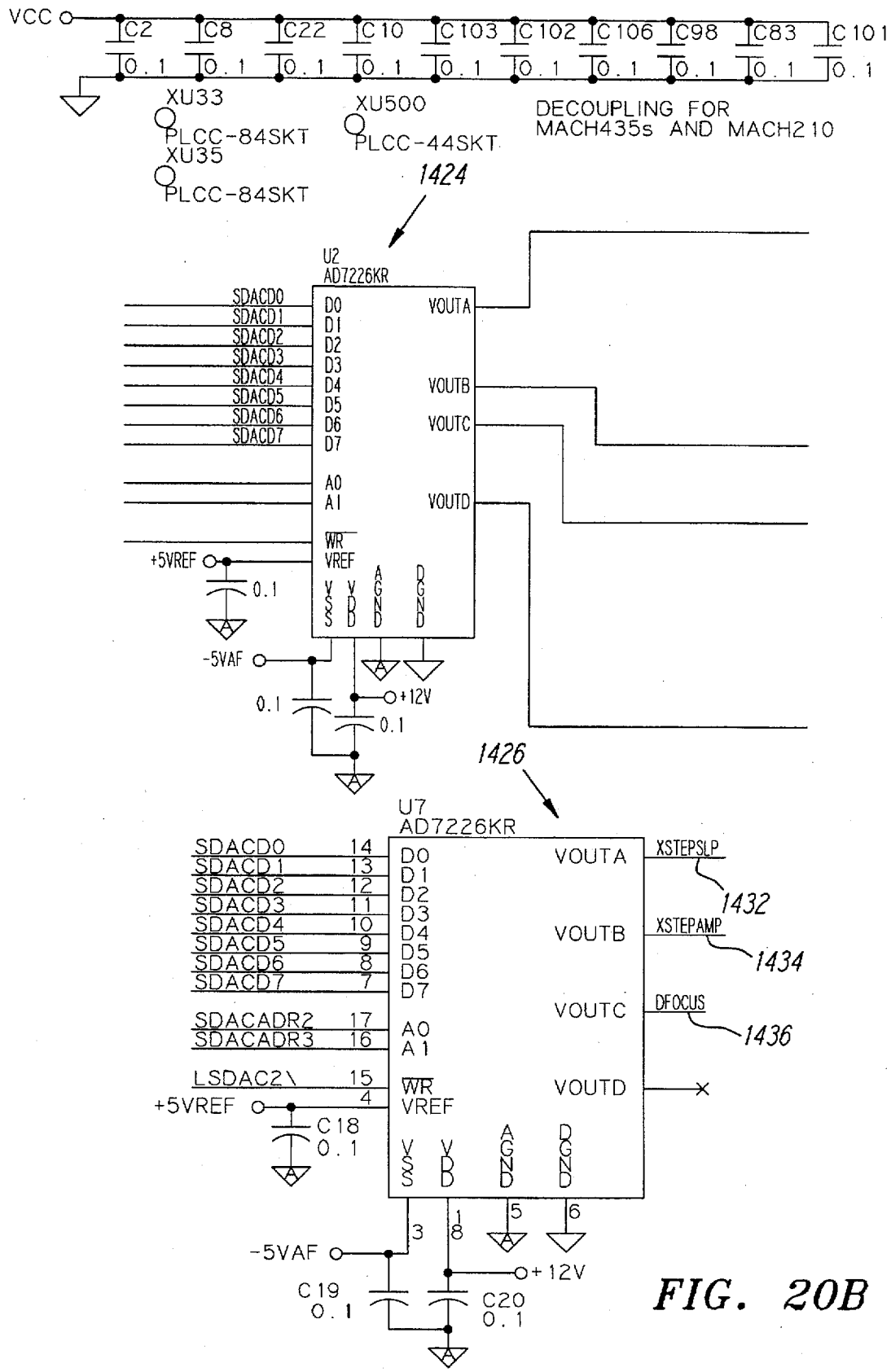
Figure 20C:
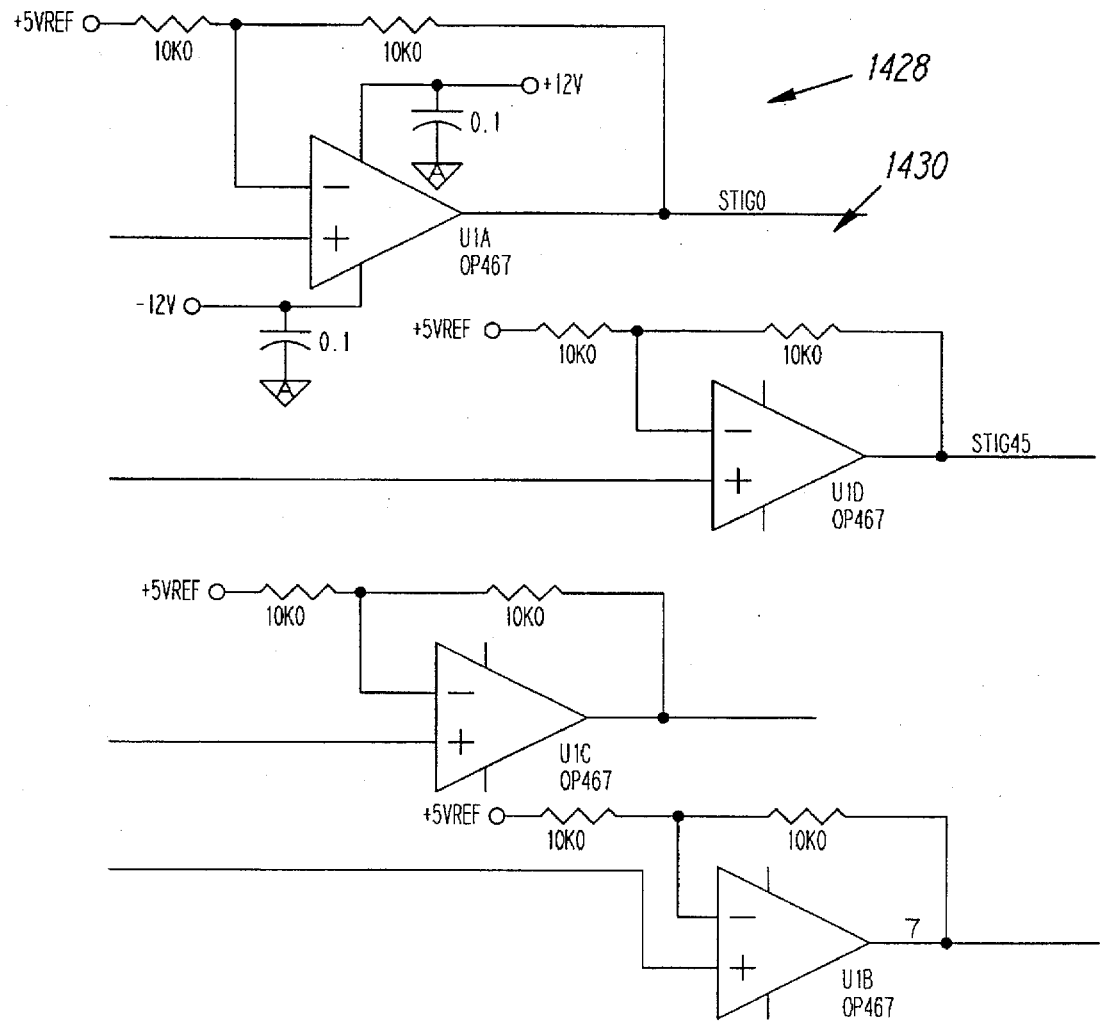
Figure 21B:
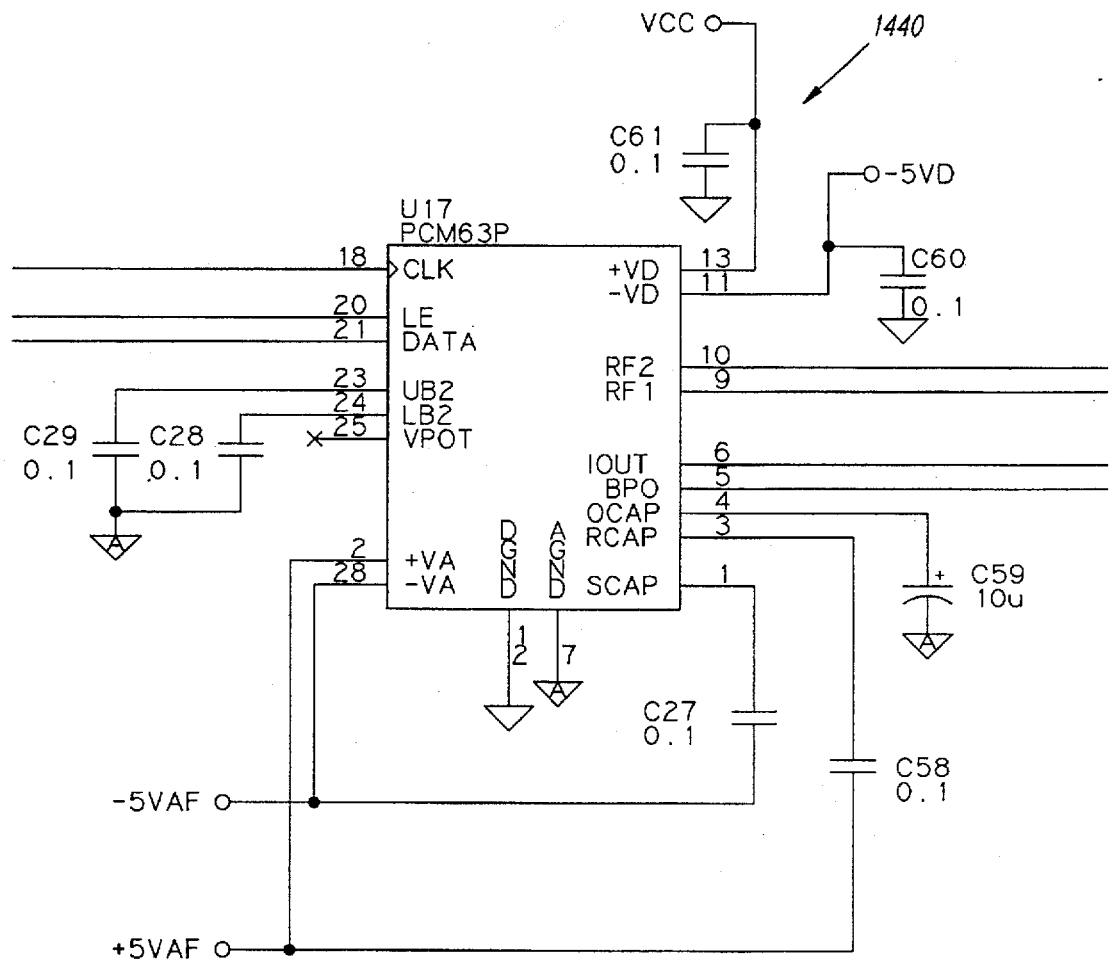
Figure 21C:
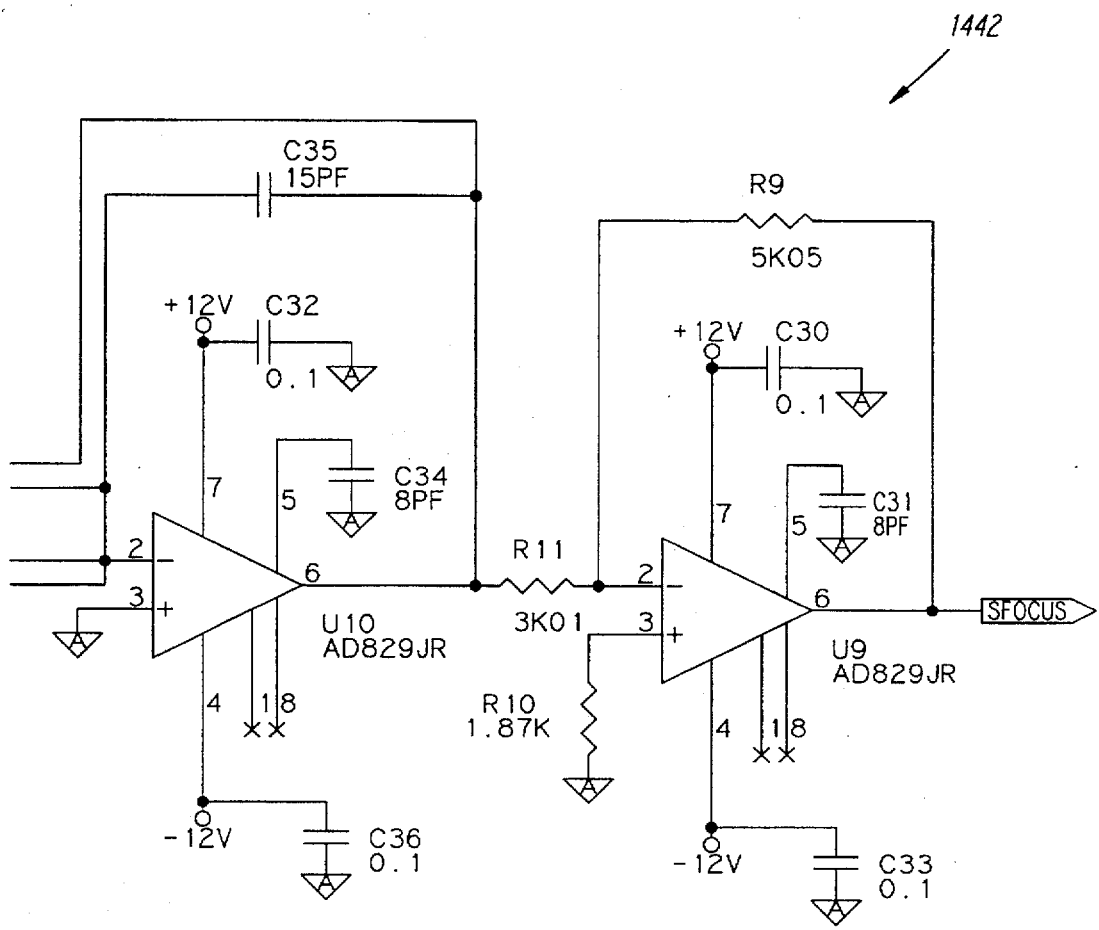
Figure 22A:
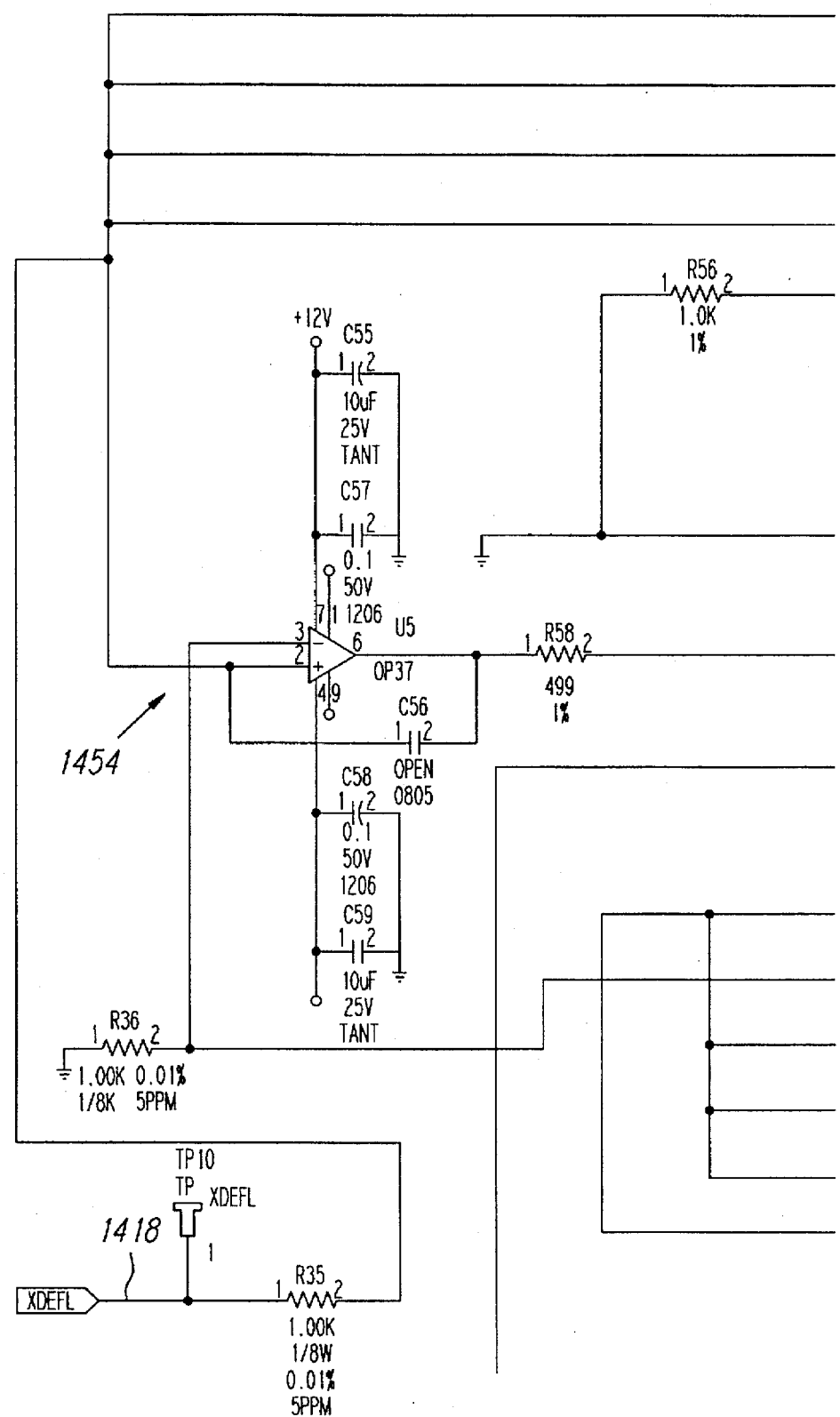
FIGS. 22A–C and 23A–C are schematics of the preferred x-deflection driver.
Figure 22B:
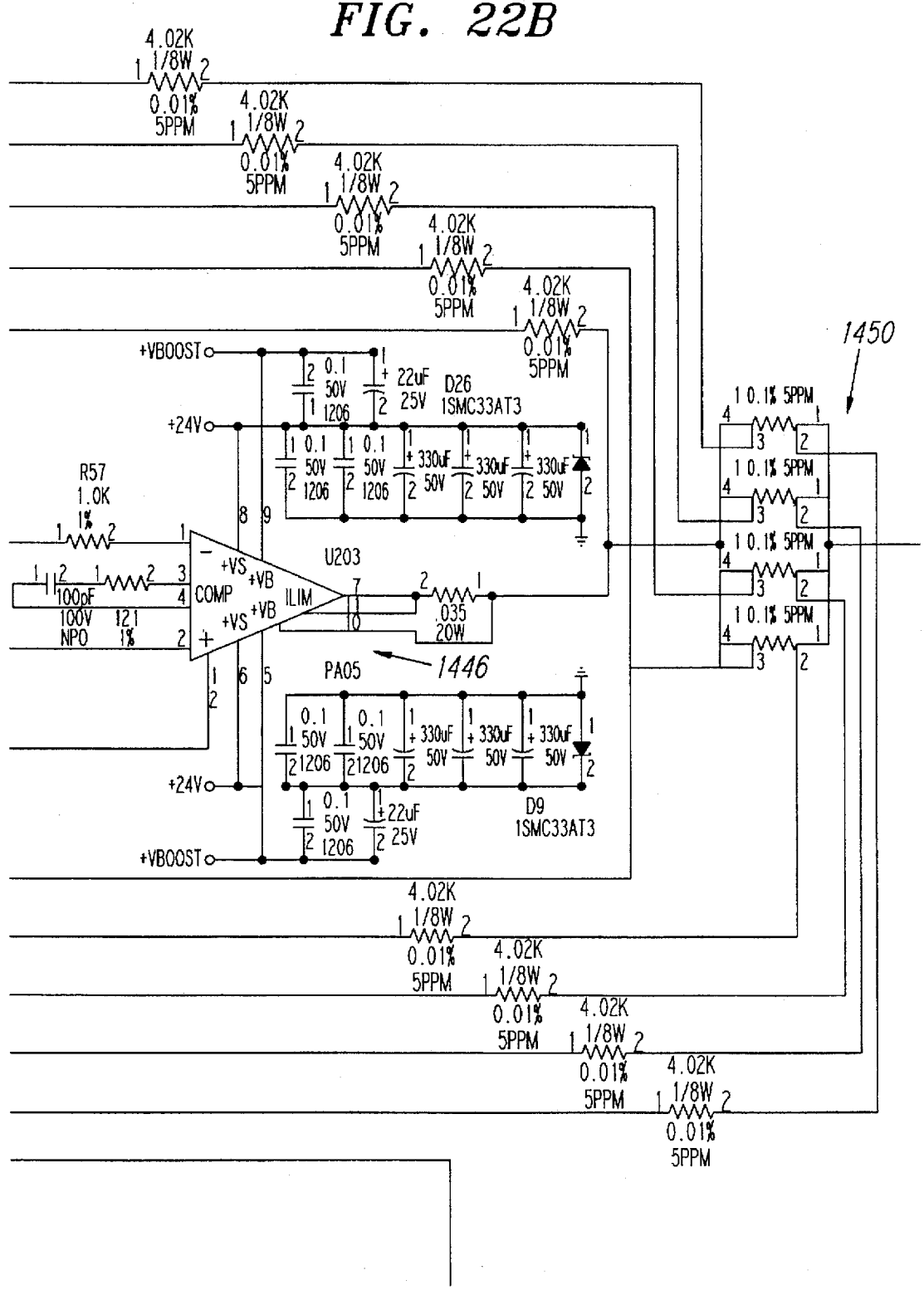
Figures 22, 22C:
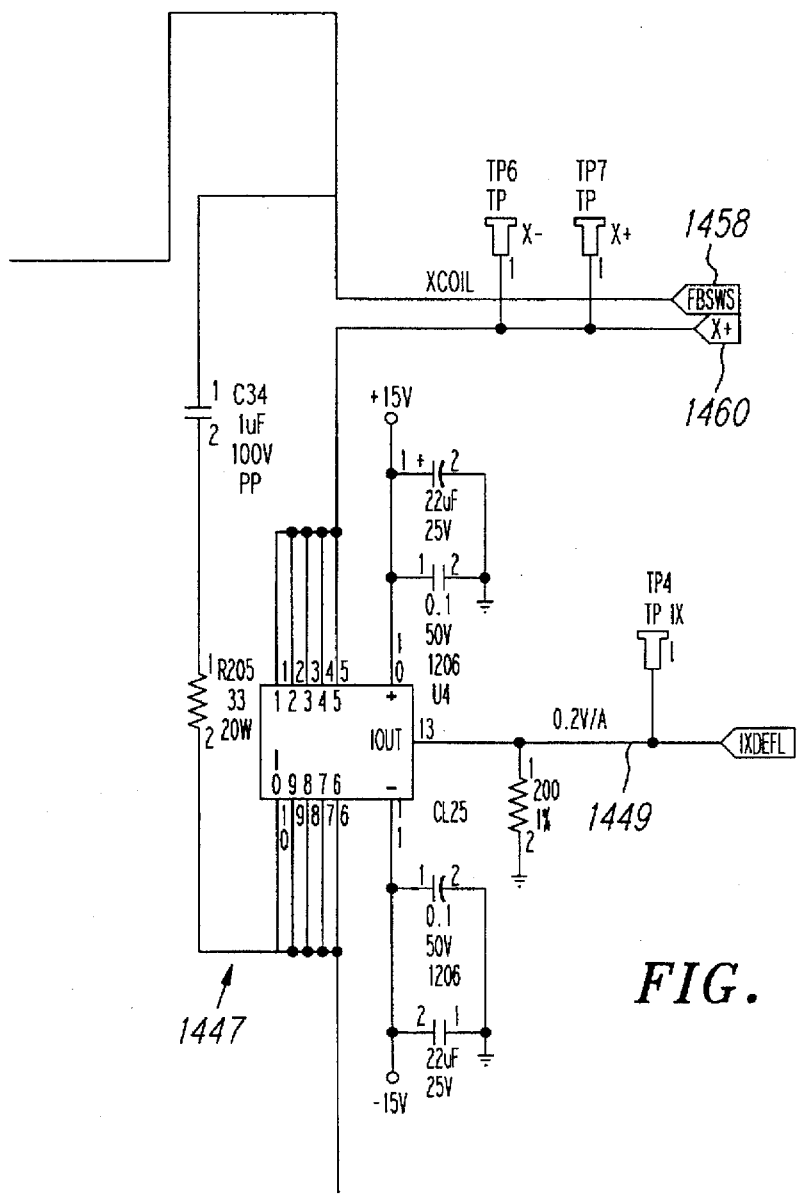
FIG. 22 is a key to FIGS. 22A–C and 23A–C.
Figures 23, 23A:
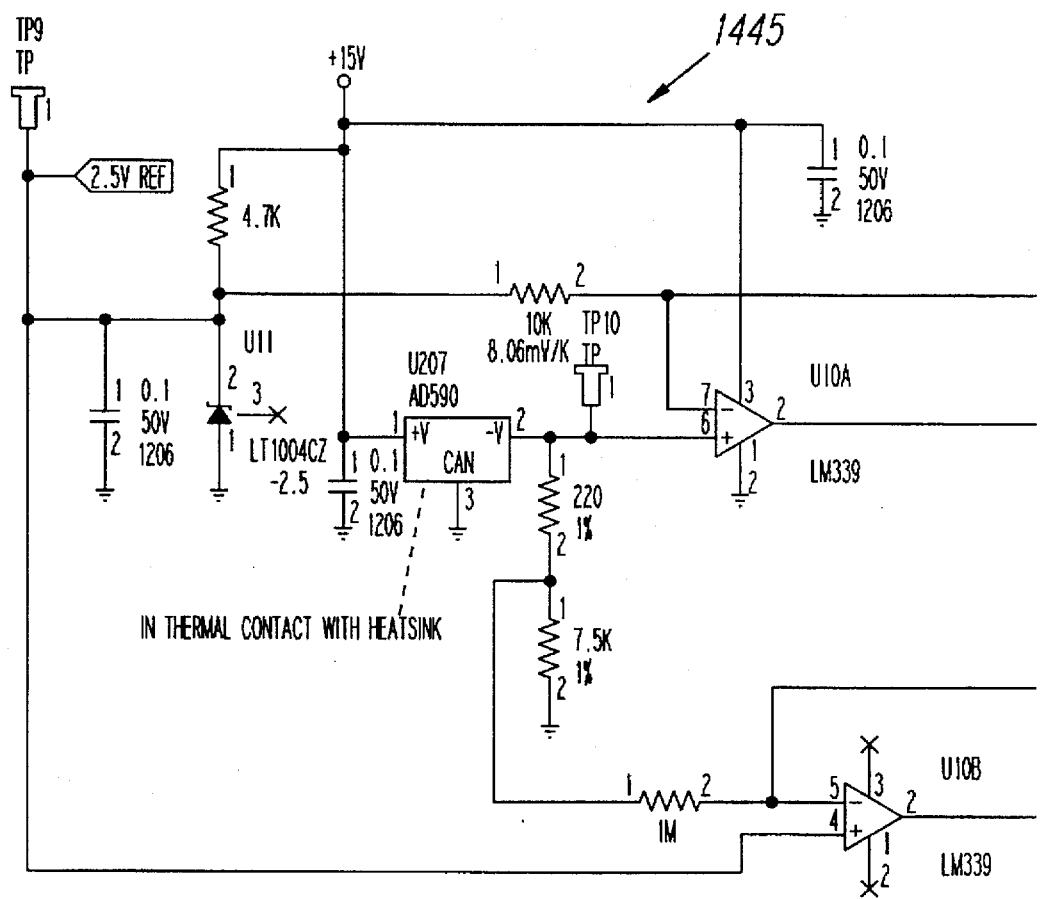
FIG. 23 is a key to 23A–C.
Figure 23B:
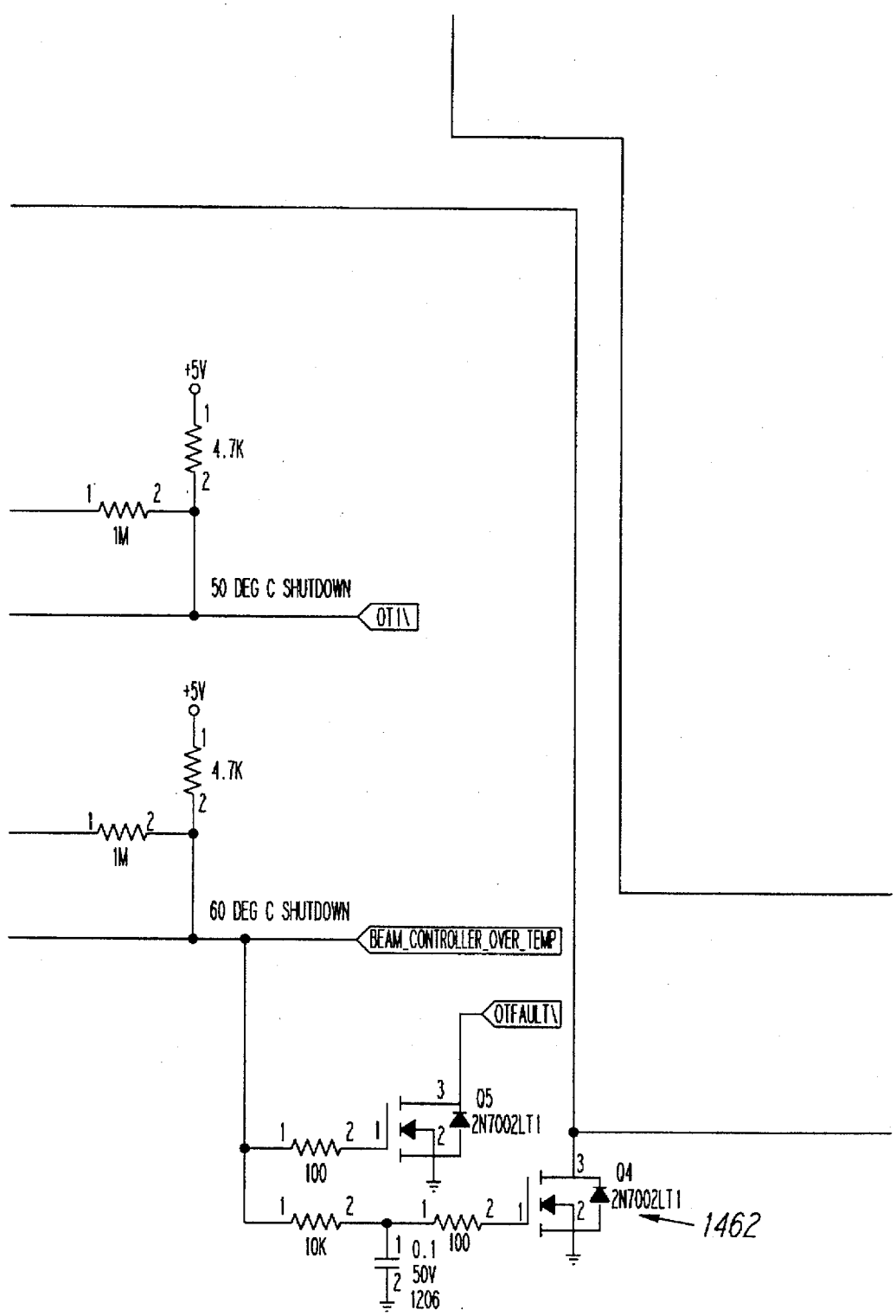
Figure 23C:
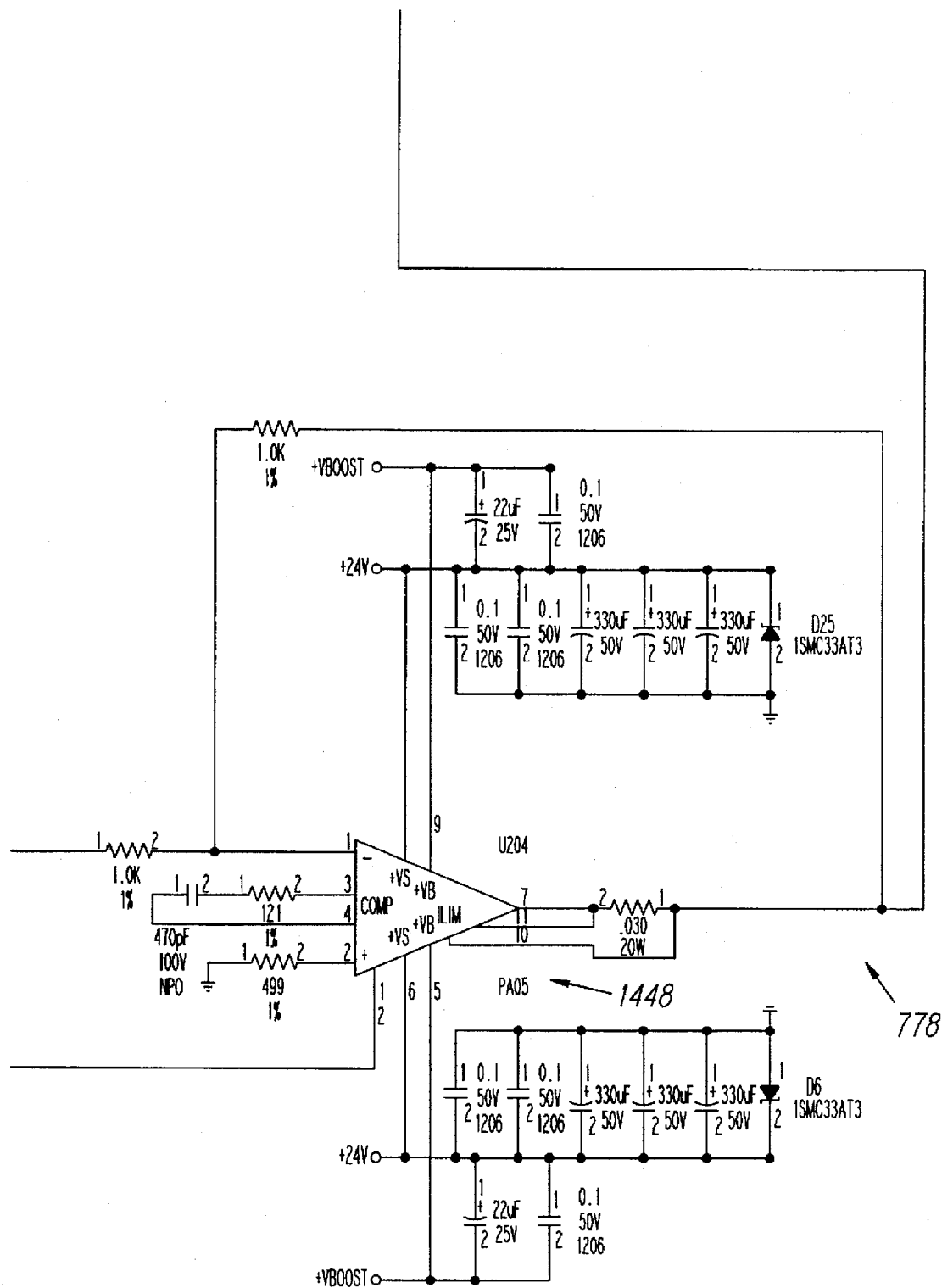

FIG. 16 is a partial block diagram of a preferred scanning beam x-ray imaging system, showing a preferred beam controller 796 and a portion of a C-arm cart. FIG. 16 depicts only a portion of the overall scanning beam x-ray imaging system; the other components of this imaging system, and the exact placement of FIG. 16 in relation to these other components, are discussed more fully in copending appl. Ser. No. 08/386,861, which was incorporated herein by reference in its entirety. Accordingly, only select aspects of the preferred imaging system from the copending application are discussed in the following paragraphs; thus, reference is made to the previously mentioned copending application for greater details concerning the other components of the preferred scanning beam x-ray imaging system.

Beam controller 796 preferably controls the focus coils through two separate drivers, a static focus driver 774 and a dynamic focus driver 776. Static focus driver 774 is preferably set only once for a given operating voltage of the high voltage power supply. The dynamic focus driver 776 adjusts the precise focussing of the electron beam 1240 as it scans across a target.

Beam controller 796 preferably controls the deflection coils through five separate drivers: x-deflection driver 778, x-step driver 780, y-deflection driver 782, 45° stigmator driver 784, and 0° stigmator driver 786.

The x-deflection driver 778 communicates a conventional linear input pattern to the deflection coils via wires 1046 to drive the electron beam horizontally across the target whereas the x-step driver 780 communicates a novel sawtooth input signal to the deflection coils via wires 1048. The net effect is a stepped movement of the electron beam across the target. The y-deflection driver 782 communicates a conventional y-deflection pattern to the deflection coils via wires 1050 to drive the electron beam 1240 vertically across the face of the anode. The 45° stigmator driver 784 and the 0° stigmator driver 786 and their respective coils correct for aberrations in the electron beam spot to maintain a circular spot on the target.

Beam controller interface information, including grid voltage, static focus current, current sense select, current sense sample select information and current sense sample information, is transmitted to beam controller interface 794 from an I/O controller 762 via cable 1080. Current sense monitor 788 is preferably used to monitor the output of the beam controller drivers to verify their correct operation as well as to measure the electron beam current as previously discussed. The preferred I/O controller and C-arm cart 811 are disclosed in more detail in copending appl. Ser. No. 08/386,861.

A failure in the deflection system could result in the electron beam not scanning across the target in the x direction or the y direction. This could result in thermal damage to the target. Deflection fault sensor 770 preferably receives x-scan and y-scan monitoring information from x-deflection driver 778 and y-deflection driver 782. Deflection fault sensor 770 preferably transmits a fault status signal to a fail-safe controller via fiber-optic cable 1072. If a deflection fault condition occurs, fail-safe controller will shutdown the x-ray source. Fail-safe controller preferably receives and monitors status information from various components of the system and is designed to disable the system upon detection of a potential safety problem. If the fail-safe controller detects such a potential problem, it will preferably: (1) signal the grid controller 738 to disable (turn off) the electron beam; (2) shut down the high-voltage power supply 790; and (3) shut down the static focus driver 774 to defocus the electron beam.

A tube controller generates scan control data which directs the operation of the beam controller 796, thereby controlling the scanning pattern of the x-ray source. Tube controller functionally comprises a beam deflection lookup table which stores beam deflection data for each point on the target anode, programmable scan controller 920, beam transmitter 916, I/O transceiver 964, and I/O latch 958. Data from a beam deflection lookup table 918 is preferably sent to beam controller interface 794 via a beam transmitter 916 and high-speed fiber-optic link 1000. This data includes: (1) current sense sample signals; (2) dynamic focus; (3) x-step; (4) x-deflection; (5) y-deflection; (6) 45° stigmator; (7) 0° stigmator; and (8) "beam on request" signals. Preferably, approximately every 1.28 microseconds, a new set of data is sent from the beam deflection lookup table 918 to the beam controller interface 794. The preferred tube controller and beam deflection lookup table is disclosed in more detail in copending appl. Ser. No. 08/386,861.

FIGS. 17A–B, 18, 19A–C, 20A–C, and 21A–C diagram the control logic within the beam controller interface 794, which processes and distributes analog coil current control signals to the various coil drivers. The digital scan control data generated by the tube controller 807 is optically coupled to the beam controller input circuit 1408, which preferably includes the optical communications circuit described more fully in copending appl. Ser. No. 08/386,861. Beam controller input circuit 1408 outputs eight parallel bits of digital scan control data to an eight-bit data bus D [0 . . . 7] and four parallel bits of control data CD to a control PAL 1410, which distributes and/or reformats the digital scan control data within the beam controller interface 794. The preferred software modules for control PAL 1410 are included as APPENDIX A(1).

Referring to FIGS. 18 and 19A–C, control PAL 1410 preferably outputs control signals, via leads 1411 (LD1 and LD2), to instruct the x-deflection PAL 1412 to sequentially load parallel bits of digital x-deflection coil control data DXDEF from the eight-bit data bus D [0 . . . 7]. The x-deflection PAL 1412 essentially manipulates the digital x-deflection coil control data DXDEF to generate a smoothly ramping triangular waveform at the x-deflection driver 778. Approximately every 1.28 usec, the x-deflection PAL 1412 preferably converts the parallel bits of digital x-deflection coil control data DXDEF to serial bits of digital x-deflection coil control data SDX. The serial x-deflection coil control data SDX is coupled, via output line 1413, to a twenty-bit serial DAC 1414 which converts the information to an analog signal that is preferably applied to an intermediate x-deflection amplifier 1416. The preferred software modules for x-deflection PAL 1412 are included as APPENDIX A(2).

Approximately every 80 nsec, the x-deflection PAL 1412 mathematically manipulates the sequentially acquired items of digital x-deflection coil control data DXDEF to calculate an eight-bit x-slope value, which is referred to as the x-slope control data XSD. The x-slope control data XSD is transmitted to DAC 1418 for conversion to an analog signal, and its analog output signal is preferably coupled to a series of intermediate x-slope amplifiers 1420. The amplified analog x-slope control signals XSD is preferably summed with the amplified analog x-deflection coil control data SDX to generate a smoothly ramping output waveform, which is amplified by intermediate amplifier 1417 to produce the x-deflection coil control signal XDEFL. The x-deflection coil control signal XDEFL is preferably output, via output line 1418, to a preferred x-deflection driver 778, which is described more fully in connection with the detailed description of FIGS. 22A–B and 23A–C. Alternatively, the x-deflection coil control signal XDEFL can be coupled, through an amplifier 1419 and a BNC connector 1444, to a commercially available amplifier, for example a Centronics amplifier, which then drives the current in the x-deflection coil.

Analog y-deflection coil control signals are generated in the same fashion and output to a y-deflection driver 782. However, if a raster scan pattern is employed, then the serial y-deflection coil control data SDY is directly generated by the control PAL 1410, therefore a y-deflection PAL, y-slope control data YSD, and related circuitry are not required.

Control PAL 1410 also outputs control signals, via leads 1421 (LD6, LD7, LD8, LD9, and LD10), to instruct the small DAC control PAL 1422 to sequentially load x-step control data (XCD), dynamic focus coil control data (DFCD), and stigmator control data (SCD) from the data bus D [0 . . . 7]. Small DAC control PAL 1422 redistributes the XCD and DFCD control signals to multi-channel DAC 1426 and redistributes SCD control signals to multi-channel DAC 1424. DAC 1424 preferably outputs analog 0° stigmator coil control signals to the 0° stigmator driver 786 through an intermediate 0° amplifier 1428. Analog 45° stigmator coil control signals are similarly output to the 45° stigmator driver through an intermediate 0° amplifier 1430. DAC 1426 preferably outputs analog x-step slope control signals XSTEPSLP to the x-step driver 780 via output line 1432. Similarly, analog x-step amplitude control signals XSTEPAMP are preferably output to the x-step driver 780 via output line 1434 and analog dynamic focus coil control signals DFOCUS are preferably output to the dynamic focus driver 776 via output line 1436. The preferred software modules for small DAC control PAL 1422 are included as APPENDIX A (3).

Serial data PAL 1438 preferably receives static focus coil control data SDIN from the I/O controller 762. Serial data PAL 1438 couples control data SDIN to a DAC 1440, which converts this information to analog static focus coil control signals which are sent to the static focus driver 774 through intermediate focus amplifiers 1442. The preferred software modules for serial data PAL 1438 are included as APPENDIX A(4).

The analog coil control signals from the beam controller interface 794 are preferably transmitted to suitable power amplifier circuits within the coil drivers to drive the current patterns in their corresponding focus or deflection coils. For example, the analog x-deflection coil control signals XDEFL from the beam controller interface 794 are preferably coupled, via input line 1418, to a preferred x-deflection driver 778 (FIGS. 22A–B and 23A–C). The XDEFL control signals are applied to a control amplifier 1454, which regulates the activity of power amplifiers 1446 and 1448. The x-deflection driver 778 is preferably a circle bridge circuit in which power amplifiers 1446 and 1448 differentially drive both ends of the x-deflection coil. The output voltages of the power amplifiers 1446 and 1448 are coupled, through current sense resistors 1450 and current sensor 1447, to the x-deflection coil via output lines 1458 and 1460. Resistors 1450 sense the current in the x-deflection coil and preferably feeds the current information back to regulate the control amplifier 1454. The current in the x-deflection coil is also monitored by a current sensor 1447, which transmits the measured current, via output line 1449, to the current sense monitor 788. Temperature sensor 1445, which measures the temperature at the x-deflection driver 778, employs a temperature switch 1462 to disable the x-deflection driver 778 if a temperature fault condition occurs. The y-deflection driver 782 preferably includes a similar circuit to drive the current in the y-deflection coil.

Figure 24:
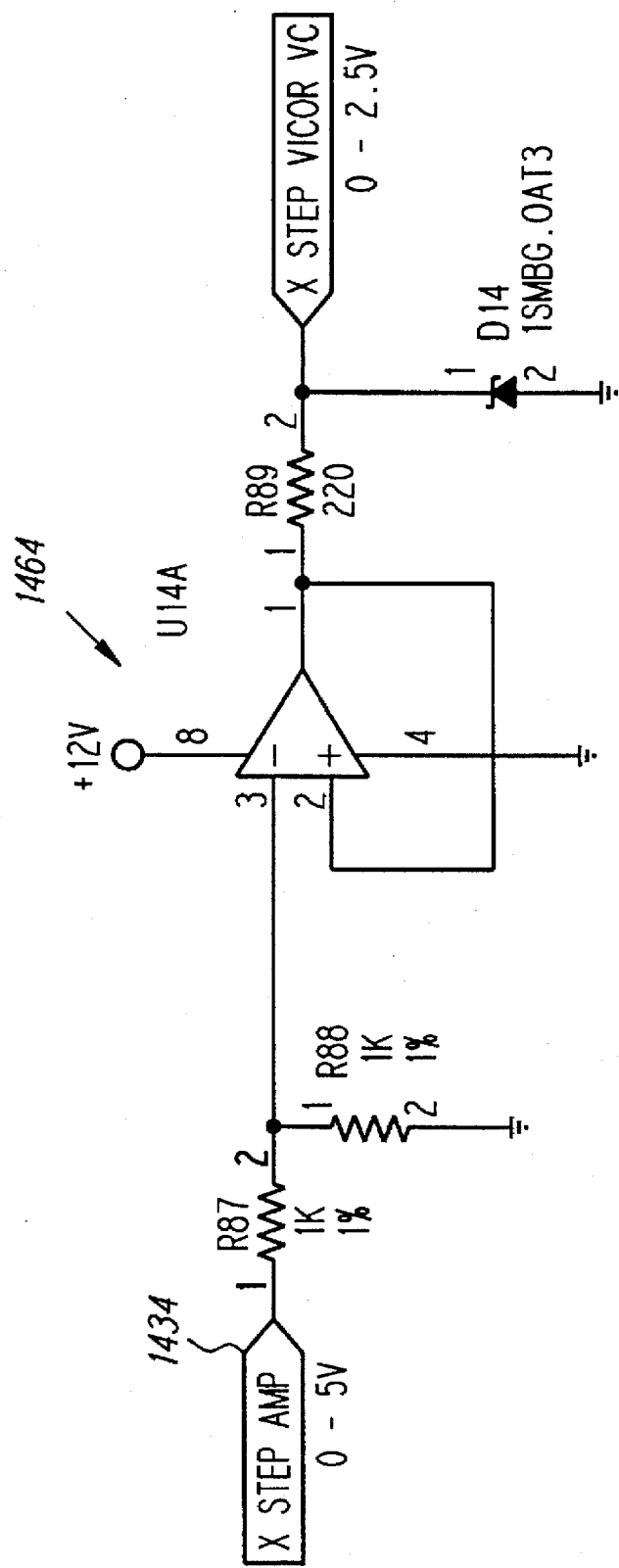
FIGS. 24 and 25A–E are schematics of the preferred x-step driver.
Figure 25A:
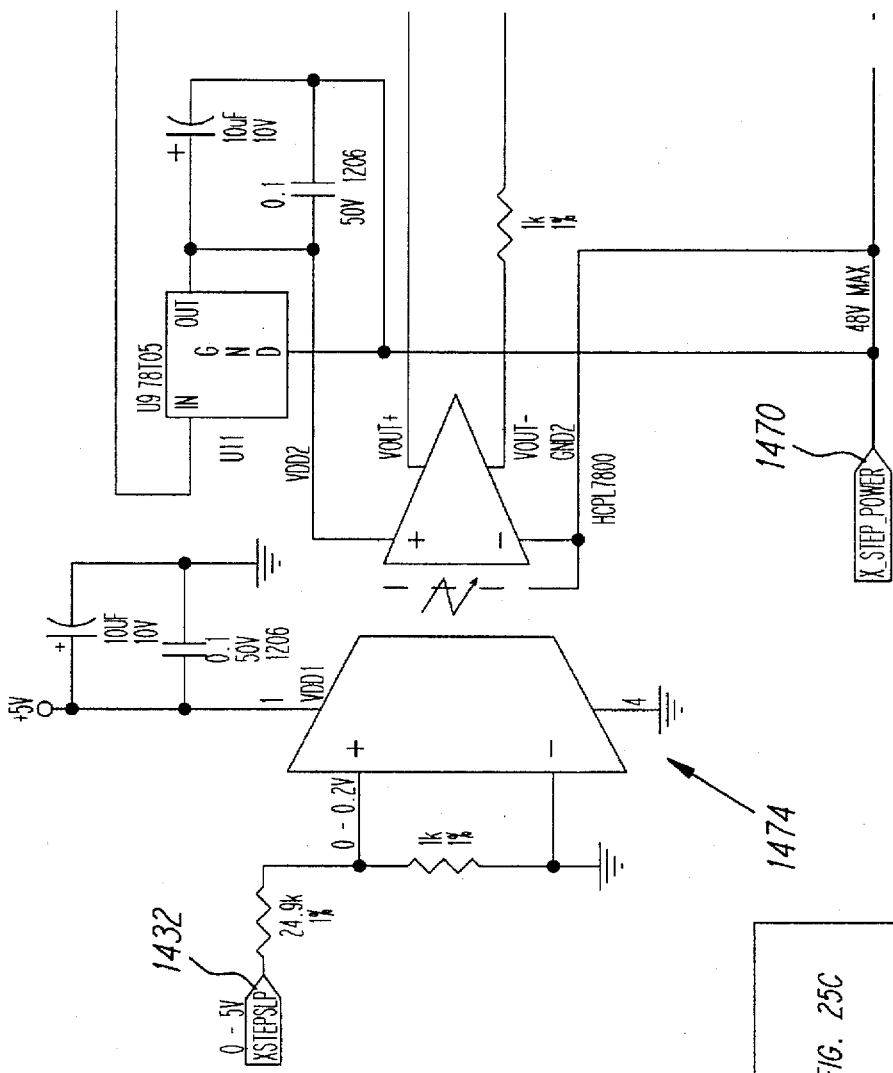
Figure 25:
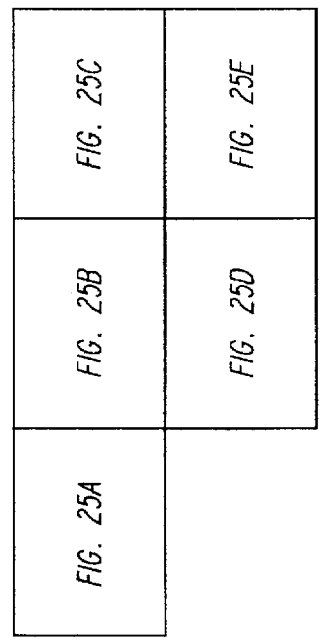
FIG. 25 is a key to FIGS. 25A–E.
Figure 25B:
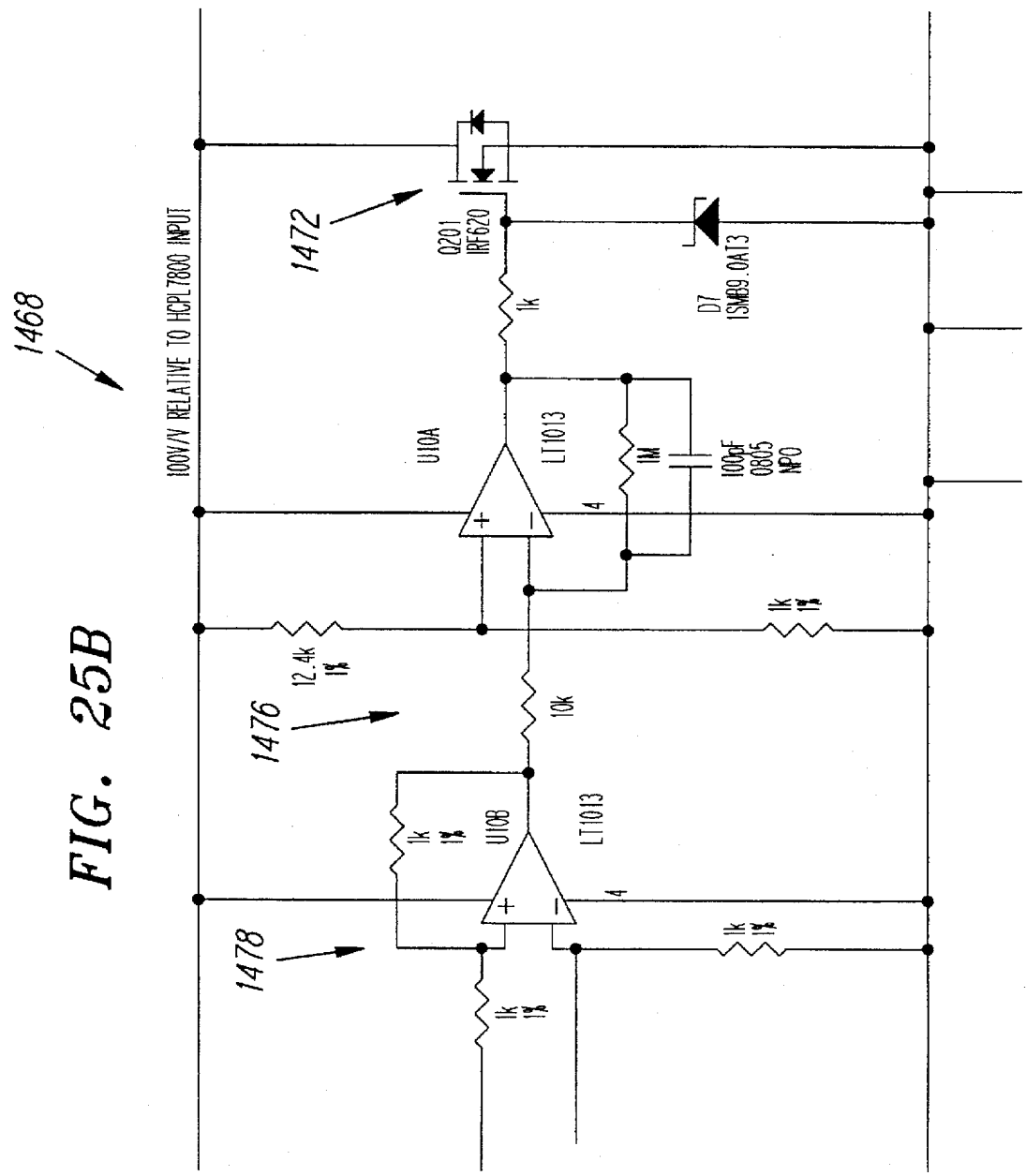
Figure 25C:
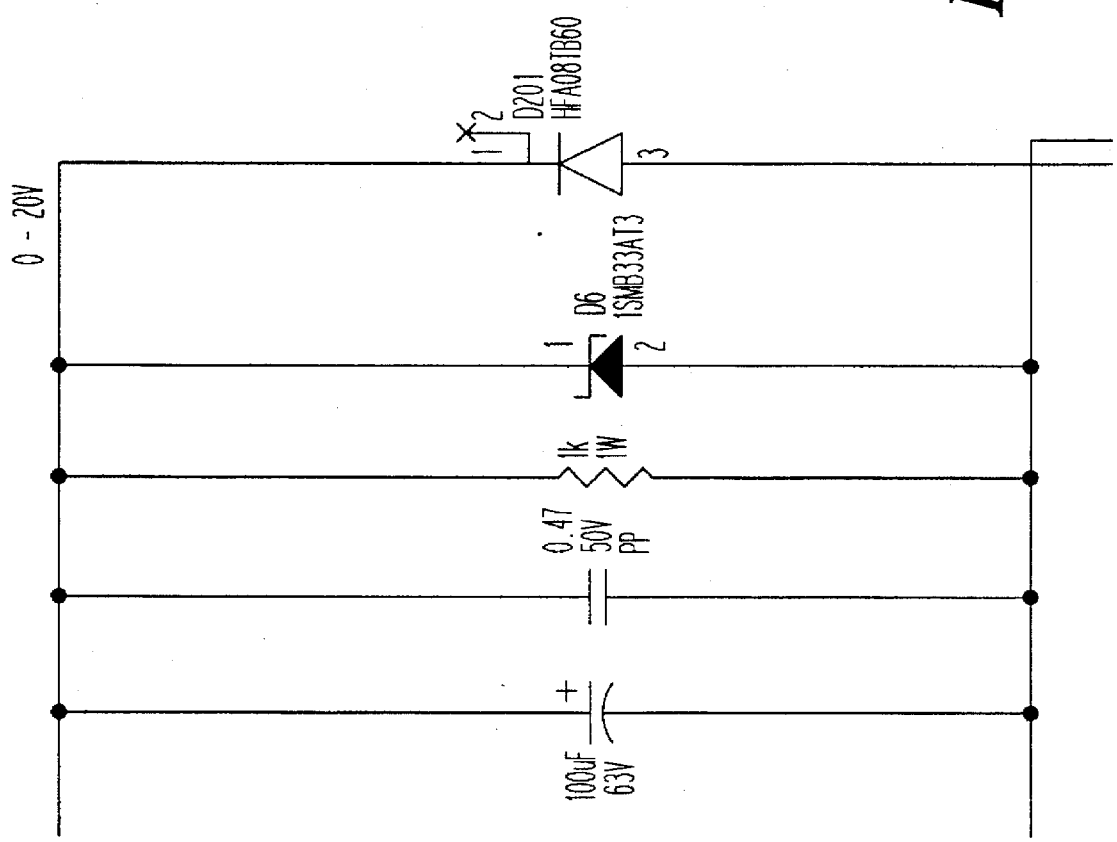
Figure 25D:
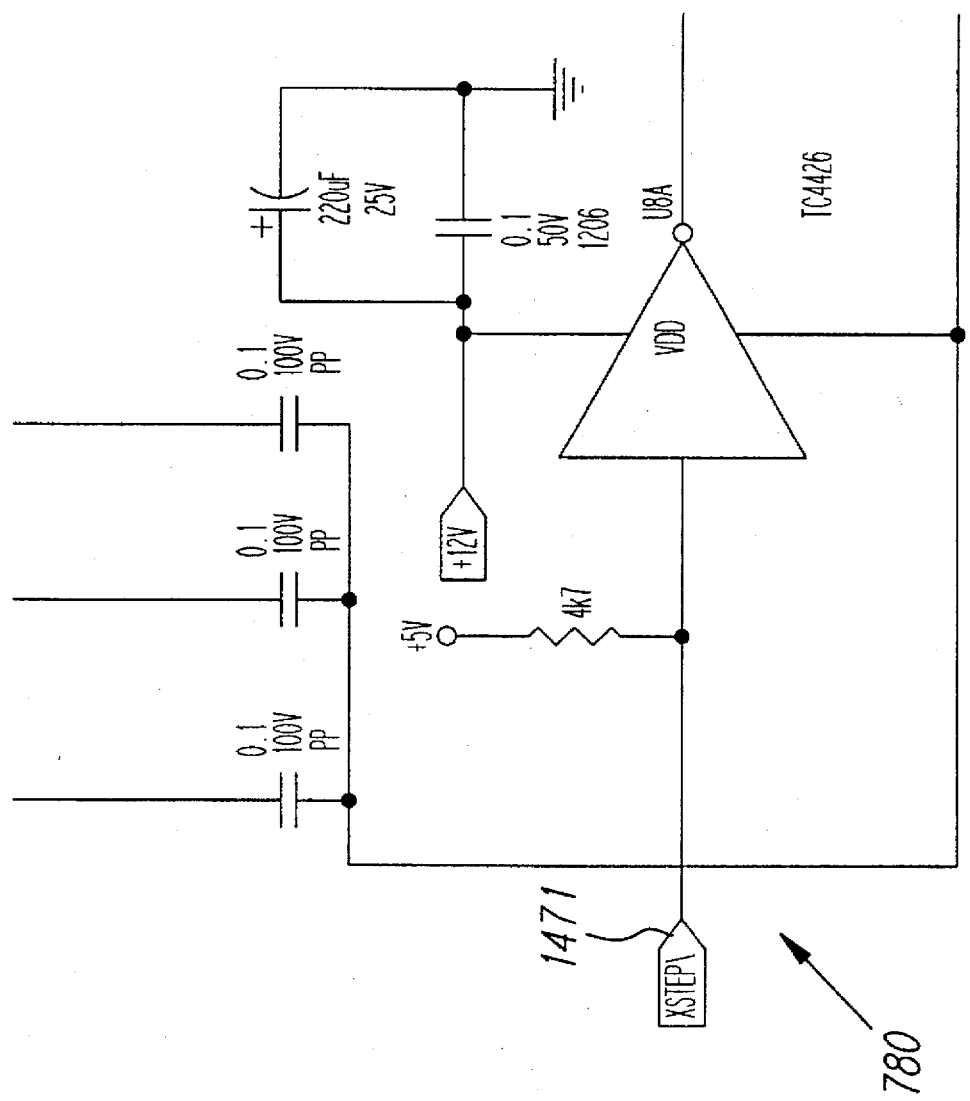
Figure 25E:
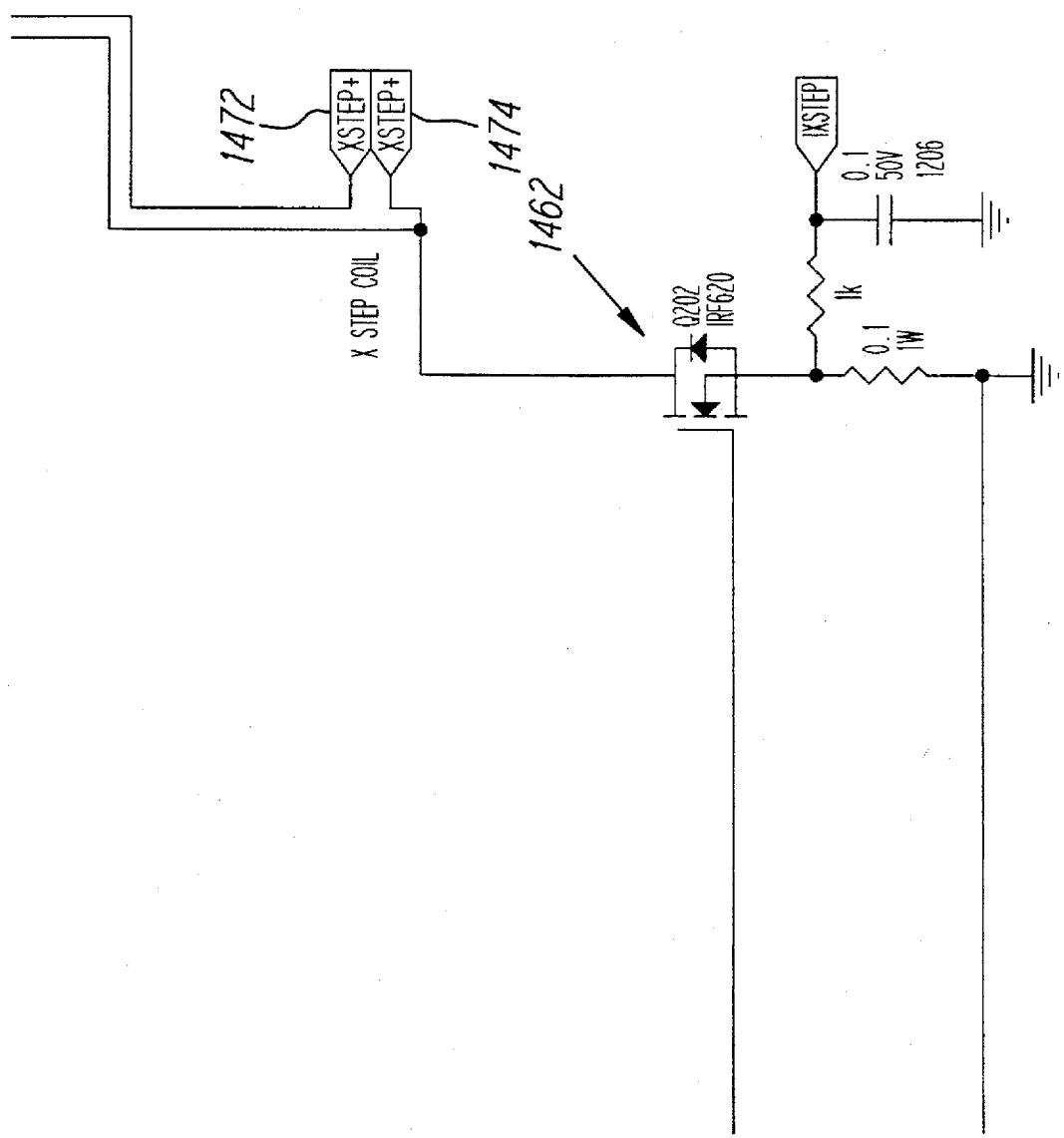

X-step driver 780, which preferably comprises x-step ramp control switch 1462, x-step voltage control circuit 1464, and decay control circuit 1468 (FIGS. 24 and 25A–E), is preferably employed to generate a sawtooth current wave form in the x-step coil. The x-step driver 780 is connected across the x-step coil via output leads 1472 and 1474. Referring to FIG. 24, x-step amplitude control signals XSTEPAMP from the beam controller interface 794 are preferably applied to x-step voltage control circuit 1464 to control the voltage level of a VICOR multi-output switching power supply (not shown), which supplies an input voltage to the x-step driver 780 via input line 1470.

Ramp switch control signals XSTEP\ are preferably applied from the control PAL 1410, via input line 1471, to control the operation of the x-step ramp control switch 1462. When the x-step ramp control switch 1462 is switched on, voltage from the VICOR multi-output power supply is applied to the x-step coil, allowing the current in the x-step coil to ramp up for a specified time period, preferably 1 to 200 nsec. The amplitude of the current pattern is determined by the voltage level of the VICOR multi-output power supply, which is preferably set by the x-step voltage control circuit 1464.

When the x-step ramp control switch 1462 is switched off, decay control circuit 1468 applies a voltage to the x-step coil to control and shape the slope of the current decay in the x-step coil. X-step slope control signals XSTEPSLP are preferably applied to the decay control circuit 1468 via input line 1432. An isolation amplifier 1474 is preferably employed to optically couple the x-step slope control signals XSTEPSLP to the decay control circuit 1468, to avoid potential problems relating to high voltages applied to the circuit by the VICOR power supply. The output of the isolation amplifier 1474 is preferably coupled to an intermediate x-step amplifier 1478. Intermediate x-step amplifier 1478 preferably converts the differential output from isolation amplifier 1474 into a single ended signal, which is coupled to the inverting input of a control amplifier 1476. Control amplifier 1476 manages the voltage across transistor 1472, which functions as a variable load, such that the voltage applied to the x-step coil during the current decay period produces an optimal current decay rate in the x-step coil. If a particular x-ray imaging application requires the use of a y-step coil, then a y-step driver similar to the x-step driver of FIGS. 24 and 25A–E is preferably employed.

While embodiments, applications and advantages of the invention have been shown and described with sufficient clarity to enable one skilled in the art to make and use the invention, it would he equally apparent to those skilled in the art that many more embodiments, applications and advantages are possible without deviating from the inventive concepts disclosed and described herein. The invention therefore should only he restricted in accordance with the spirit of the claims appended hereto and is not to be restricted by the preferred embodiments, specification or drawings.

APPENDIX A

This document is an appendix to the U.S. patent application entitled "X-Ray Source." This appendix contains program listings for the preferred software modules for the programmable logic devices employed in the above-identified invention. These software modules are written in ABEL V. 5.1, from DATAIO Corp., for x86 based IBM PC-compatible computers.

APPENDIX A(1)

```
module bcicnt title 'Beam Controller Interface -- Beam Control
       Ver. 0; 12-29-94'
       B1U4R0 device 'MACH435A';

"inputs
       TFMHZ,TFMHZO pin 20,23;
       D0..D7 pin 12..19;
       C0..C3 pin 25..28;
       DSTRB,CSTRB pin 24,29;

"outputs
       TWMHZO,BOR_ pin 3,4 istype 'reg_D,buffer';
       XSTEP_ pin 5;
       CSTRBS,CSSTRB pin 33,34;
       SDY,LTCHENY pin 38,40 istype 'reg_D,buffer';
       CLKY pin 39;
       LD1,LD2 pin 45,46;
       LD6..LD10 pin 50,51,52,54,55;
       LD11,LD12 pin 66,67;
       BCOK pin 82;

"nodes
       LD3,LD4,LD5,NDATA,DSTRBL,LDDAC,CSS,CS15 node;
       CS15L node istype 'reg_D,buffer';
       CLE,SHIFT,LDSR node istype 'reg_D,buffer';
       BCNT4..BCNT0 node istype 'reg_T,buffer';
       BCCY node;
       CBREG7..CBREG0 node istype 'reg_D,buffer';
       LDCNT3..LDCNT0 node istype 'reg_T,buffer';
       YD18..YD0 node istype 'reg_D,buffer';
       YS19..YS4 node istype 'reg_D,buffer';

"constants
       H,L,C,X,Z = 1,0,.C.,.X.,.Z.;
       DV    = [D7..D0];
       CV    = [C3..C0];
       CBREG = [CBREG7..CBREG0];
       LDCNT = [LDCNT3..LDCNT0];
       BCNT  = [BCNT4..BCNT0];
       YD    = [SDY,YD18..YD0];
       YSH   = [YS19..YS12];
       YSL   = [YS11..YS4];

TF = [CLE,LDSR,SHIFT,BCNT,LDCNT,CS15L];

"timing (normal operation)
"                1       1               2               3               4       5       6       7
         8       9       0               1               2
"iTFMHZ
 _ _ _ _ _ _ _ _ _ _ _ _ _ _ _ _ _ _ _ _ _ _ _ _ _ _ _ _ _ _ _ _ _ _ _ _ _
_ _ _ _ _ _ _ _ _ _ _ _ _ _ _ _ _ _ _ _ _ _ _ _ _ _ _ _ _ _ _
```

43B

```
"cTWMHZO
 --_--_----_--_-----_--__--__--_--_---__--__--__-_-_-__
"iCSTRB        ---   --  --    --  --  --   --  --
 _B_____          C                    B
    C              B
"cNDATA
 -------------------- -----           ------------ -----------
--------------------  ------------------
"+LDCNT
x0000011112222333344445555666677778888999911111111100000011112222333344445555666
67777888899991111111110000001111222233333
"+LDCNT                                              0000111122
              0000111122
"cLDDAC
   _                _                    _____
"iDSTRB    .
   _ __  __ ___ __ __ __ __ __ __ __ _ __ _ __ __ _ __ _
"cDSTBL
   _  __   __ _ _  _ _ _   _ __ _ _
"+CLE.d                                ---    --      --   --
  -   _   __ _ __      __    __  _    _         __   __   _
"-CLE               _   _        _   __     __    __    __
  _   _   __ _ __  _  _  _ _  _  __  __  _
"cCS
----------------------------------     -------          -----------
"cLDAC        -------               -----------------
--------------------------------------     ---------     ------
"cLD1
  _  -
"cLD2                                              -
"cLD3                                                                 -
"cLD4
                        -                              -
"cLD5                                   -
"cLD6
                  -                                         -
"cLD7
               -                                               -
"cLD8
  -            -
"cLD9
                      -
"cLD10
             -
"cLD11        -
         -
```

43c

```
"cLD12
_____   _____
                                               __
"cLDSR.d
_____
                                  --                                    .
"+LDSR
                                  --
   --
"iTFMHZ
_._._._._._._._._._._._._._._._._._._._._._._._._._._._._._._._._._._._._._
"cSHIFT.d
                    ---------------------------------------------------
"+SHIFT
   ---------------------------------------
"SDATA    know how many clocks I have sent x1111111111111111111
             11111111111111111111
"
x99887766554433221100998877665544332211000000
998877665544332211009988776655443322
"oCLKY
                    - - - - - - - - - - - - - -        - - - - - - - - - - -
"cLDDAC
            -
"cLTCHENY.d--------------------------------
           ----------
"-LTCHENY  actually a low true signal
---                                      ----------
"+BCNT    counts number of bits sent
00011223344556677889911111111111111111111122222222220000112233445566778899111111
11111111
"
0011223344556677889900112233 44                0011223344556677
"cBCCY
 --
--
``` equations
"CLOCK GENERATION

TWMHZ0.clk = TFMHZ0;
        TWMHZ0 := !TWMHZ0;
        TF.clk = TFMHZ;

43D

```
"TIMING SIGNALS
        CSS     = BCOK&((CSTRB&((CV==11) # (CV==15))) # CSS&!(DSTRB));
        NDATA   = BCOK&(CSTRB&CSS # NDATA&!(LDCNT==12));
        LDCNT.t = (LDCNT$(LDCNT+1))&CLE # LDCNT&!NDATA;
        DSTRBL  = NDATA&(DSTRB # DSTRBL&!(CLE));
        CLE.d   = DSTRBL&NDATA;
        LD1  = NDATA&(DSTRB # DSTRBL)&(LDCNT==0);
        LD2  = NDATA&(DSTRB # DSTRBL)&(LDCNT==1);
        LD3  = NDATA&(DSTRB # DSTRBL)&(LDCNT==2);
        LD4  = NDATA&(DSTRB # DSTRBL)&(LDCNT==3);
        LD5  = NDATA&(DSTRB # DSTRBL)&(LDCNT==4);
        LD6  = NDATA&(DSTRB # DSTRBL)&(LDCNT==5);
        LD7  = NDATA&(DSTRB # DSTRBL)&(LDCNT==6);
        LD8  = NDATA&(DSTRB # DSTRBL)&(LDCNT==7);
        LD9  = NDATA&(DSTRB # DSTRBL)&(LDCNT==8);
        LD10 = NDATA&(DSTRB # DSTRBL)&(LDCNT==9);
        LD11 = NDATA&(DSTRB # DSTRBL)&(LDCNT==10);
        LD12 = NDATA&(DSTRB # DSTRBL)&(LDCNT==11);

!XSTEP_ = BCOK&(CSTRB&CSS # !XSTEP_&!(LD3));
        CSTRBS  = BCOK&(CSTRB&(CV==12) # CSTRBS&!(DSTRB));
        CSSTRB  = BCOK&(CSTRB&(CV==15) # CSSTRB&!(DSTRB));

"STORE CONTROL BYTE AND DETECT FAULT
        CBREG.ar = !BCOK;
        CBREG   := DV&LD5;
        CBREG.clk = LD5&TFMHZ;
        BOR_.ap = !BCOK;
        !BOR_   := CBREG0;
        BOR_.clk = !LTCHENY;
        CS15    = CSTRB&(CV==15) # CS15&!(CSTRB&(CV!=15) # DSTRB);
        CS15L   := CS15;
        BCOK    = !CS15 # BCOK&!(CSTRB&CS15&CS15L);

"SHIFT DATA TO Y-DEFLECTION DAC
        YSH    := DV&LD4;
        YSH.clk = LD4&TFMHZ;
        YSL    := DV&LD3;
        YSL.clk = LD3&TFMHZ;

YD.ar  = !BCOK;
        YD.d   = SHIFT&[YD18..YD3,0,0,0,0] # LDSR&[!YS19,YS18..YS4,0,0,0,0];
        YD.clk = !TFMHZ&(SHIFT # LDSR);

LTCHENY.d = (BCNT==20)&SHIFT # LTCHENY&!(LDDAC);      "&SHIFT # !BCOK
        LTCHENY.clk = !TFMHZ;
        CLKY    = TFMHZ&!LTCHENY&SHIFT;
        SHIFT.d = LDSR # SHIFT&!(BCNT==20);
        LDDAC   = CSTRB&(CV==12) # !BCOK&(BCNT==24) # LDDAC&!(!LTCHENY);
        BCNT.t  = (BCNT$(BCNT+1))&!LDSR&!BCCY # BCNT&(LDSR # BCCY);
        BCCY    = (BCNT==24);
        LDSR.d  = LD8 # !BCOK&(BCNT==24);

end
```

APPENDIX A(2)

```
module bcixdef title 'Beam Controller Interface -- X-DEFL Control
       Ver. 0; 12-29-94'
       B1U6R0 device 'MACH435A';

"inputs
       TFMHZ pin 20;
       LD1,LD2,LD8 pin 3,4,5;
       D0..D7 pin 12..19;
       CSTRBS pin 25;
       BCOK pin 82;

"outputs
       XSCS_,XSWR_ pin 30,31;
       XSD0..XSD7 pin 33..40 istype 'reg_D,buffer';
       SDX,LTCHENX pin 45,47 istype 'reg_D,buffer';
       CLKX pin 46;

"nodes
       LDDAC,BCCY node;
       CLE,SHIFT,LDSR node istype 'reg_D,buffer';
       BCNT4..BCNT0 node istype 'reg_T,buffer';
       XD18..XD0 node istype 'reg_D,buffer';
       XS19..XS4 node istype 'reg_D,buffer';

"constants
       H,L,C,X,Z = 1,0,.C.,.X.,.Z.;
       DV    = [D7..D0];
       BCNT  = [BCNT4..BCNT0];
       XD    = [SDX,XD18..XD0];
       XSH   = [XS19..XS12];
       XSL   = [XS11..XS4];

TF = [CLE,LDSR,SHIFT,BCNT];

equations

"CLOCK GENERATION

TF.clk = TFMHZ;

"SHIFT DATA TO X-DEFLECTION DAC
       XSH := DV&LD2;
       XSH.clk = LD2&TFMHZ;
       XSL := DV&LD1;
       XSL.clk = LD1&TFMHZ;

XD.ar = !BCOK;
       XD.d = SHIFT&[XD18..XD3,0,0,0,0] # LDSR&[!XS19,XS18..XS4,0,0,0,0];
       XD.clk = !TFMHZ&(SHIFT # LDSR);

LTCHENX.d = (BCNT==20)&SHIFT # LTCHENX&!(LDDAC);
       LTCHENX.clk = !TFMHZ;
       CLKX = TFMHZ&!LTCHENX&SHIFT;
       SHIFT.d = LDSR # SHIFT&!(BCNT==20);
       LDDAC = CSTRBS # !BCOK&(BCNT==24) # LDDAC&(!LTCHENX);
       BCNT.t = (BCNTS(BCNT+1))&!LDSR&!BCCY # BCNT&(LDSR # BCCY);
       BCCY = (BCNT==24);
       LDSR.d = LD8 # !BCOK&(BCNT==24);

end
```

APPENDIX A(3)

```
module bcisdac title 'Beam Controller Interface -- Small DAC Control
       Ver. 0; 12-29-94'
       B1U33R0 device 'MACH435A';

"inputs
       TFMHZ pin 20;
       D0..D7 pin 3..10;
       LD6..LD10 pin 12..16;
       BCOK pin 82;

"outputs
       SDACD0..SDACD7 pin 45,46,47,48,66,67,68,69 istype 'reg_D,buffer';
       SDADR0..SDADR3 pin 54..57;
       LSDAC1_,LSDAC2_ pin 58,59;

"nodes
       CNTCY,OE6,OE7,OE8,OE9,OE10 node;
       SZD7..SZD0 node istype 'reg_D,buffer';
       SFFD7..SFFD0 node istype 'reg_D,buffer';
       XSSD7..XSSD0 node istype 'reg_D,buffer';
       XSAD7..XSAD0 node istype 'reg_D,buffer';
       DFD7..DFD0 node istype 'reg_D,buffer';
       CNT4..CNT0 node istype 'reg_T,buffer';

"constants
       H,L,C,X,Z = 1,0,.C.,.X.,.Z.;
       DV    = [D7..D0];
       SDACD = [SDACD7..SDACD0];
       SDA1  = [SDADR1,SDADR0];
       SDA2  = [SDADR3,SDADR2];
       SZD   = [SZD7..SZD0];
       SFFD  = [SFFD7..SFFD0];
       XSSD  = [XSSD7..XSSD0];
       XSAD  = [XSAD7..XSAD0];
       DFD   = [DFD7..DFD0];
       CNT   = [CNT4..CNT0];

"timing (normal operation)
"           1         1           2           3           4          5          6          7
       8    9         0           1           2
"iTFMHZ
 -_-_-_-_-_-_-_-_-_-_-_-_-_-_-_-_-_-_-_-_-_-_-_-_-_-_-_-_-_-_-_-_-_-_-_-_-_-_-_-_-_-_-_-_
"oTWMHZO - - - - - - - - - - - - - - - - - - -
 -_-_-_-_-_-_-_-_-_-_-_-_-_-_-_-_-_-_-_-_-_-_-_-_-_-_-_-_-_-_-_-_-_-_-_-_-_-_-_-_-_-_
"iCSTRB  - - - - - - - - - - - - -
 B                  C            B                               C              B
"cNDATA
 ---------------------------------------------------_____
 -----------------   ---------
"+LDCNT
x00000111122223333444455556666777788889999111111111000000111122223333444445555666
6777788889999111111111000000111122223"
"+LDCNT
                    0000111122                              0000111122
"cLDDAC
_____   _
"iDSTRB  -
 _-_-_-_-_-_-_-_-_-_-_-_-_-_-_-_-_-_-_-_-_-_-_-_-_-_-_-_-_-_-_-_-_-_-_-_-_-_-_-_
 _-_-
```

```
"cDSTBL
_ _ _ _ _ _ _ _ _ _ _ _ _ _ _ _ _ _ _ _ _ _ _ _ _ _ _ _ _ _ _ _ _ _ _ _
"+CLE.d
_ _ _ _ _ _ _ _ _ _ _ _ _ _ _ _ _ _ _ _ _ _ _ _ _
"+CLE
_ _ _ _ _ _ _ _ _ _ _ _ _ _ _ _ _ _ _ _ _ _ _ _ _ _ _ _ _
"iTFMHZ
_ _ _ _ _ _ _ _ _ _ _ _ _ _ _ _ _ _ _ _ _ _ _ _ _ _ _ _ _ _ _ _
"cLSDAC1
------------------------------------------------      -- --
---------------------------                  _____
"                                                              DATA    777777
    888888                DATA    77777                ADDR  7777777777
"
88888888888                       ADDR  7777777777
"iTFMHZ
_ _ _ _ _ _ _ _ _ _ _ _ _ _ _ _ _ _ _ _ _ _ _ _ _ _ _ _ _ _
"cLSDAC2
                 --------------          -----------       __ __
_____ ___                       _____
"                                         DATA          666666
000000      999999     DATA        666666
"                                         ADDR       66666666666
00000000000 99999999999   ADDR   66666666666 0000
"iTFMHZ
_ _ _ _ _ _ _ _ _ _ _ _ _ _ _ _ _ _ _ _ _ _ _ _ _ _ _ _
"CNT
00112233445566778899111001122334455667788991111111111111111222222222222200112233445566778899111111111111111111112222
"                                 0011
00112233445566778899001122334455               001122334455667788990011

"cLD6
                         --_____                                     --_____
"cLD7
                _____                       --
                                                                            --
"cLD8
    --                   _____
   --
"cLD9                       -
       --                                                 --
"cLD10                     _____
                           --                         _____
   --_____ equations

"Load data into registers
        DFD.ar = !BCOK;
        DFD := DV&LD6;
        DFD.clk = LD6&TFMHZ;
        SZD.ar = !BCOK;
        SZD := DV&LD7;
        SZD.clk = LD7&TFMHZ;
        SFFD.ar = !BCOK;
        SFFD := DV&LD8;
```

```
        SFFD.clk = LD8&TFMHZ;
        XSAD.ar = !BCOK;
        XSAD := DV&LD9;
        XSAD.clk = LD9&TFMHZ;
        XSSD.ar = !BCOK;
        XSSD := DV&LD10;
        XSSD.clk = LD10&TFMHZ;

"Send data to DACs and create sync counter

CNT.ar = LD6&TFMHZ # CNTCY;
        CNT.t = CNT$(CNT + 1);
        CNTCY = (CNT==26)&!BCOK;
        CNT.clk = TFMHZ;
        !LSDAC1_ = (CNT==17)#(CNT==23) # !LSDAC1_&!((CNT==2)#(CNT==22));
        SDADR0 = 0;
        SDADR1 = !LSDAC1_&(CNT==23) # SDADR1&!(CNT==3);

!LSDAC2_ = (CNT==0)#(CNT==14)#(CNT==20) #
!LSDAC2_&!((CNT==5)#(CNT==19)#(CNT==25));
        SDADR2 = !LSDAC2_&(CNT==0)  # SDADR2&!(CNT==6);
        SDADR3 = !LSDAC2_&(CNT==14) # SDADR3&!(CNT==20);

OE6  = !OE8&((CNT==16)           # OE6 &!((CNT==19)&!TFMHZ  # LD6&BCOK));
        OE7  = !OE8&((CNT==19)&!TFMHZ # OE7 &!((CNT==22)&!TFMHZ  # LD6&BCOK));
        OE8  =       ((CNT==25)&!TFMHZ # OE8 &!((CNT==2 )&!TFMHZ));
        OE9  =       ((CNT==2 )&!TFMHZ # OE9 &!((CNT==5 )&!TFMHZ  # LD6&BCOK));
        OE10 = !OE8&((CNT==22)&!TFMHZ # OE10&!((CNT==25)&!TFMHZ));

SDACD := DFD&OE6 # SZD&OE7 # SFFD&OE8 # XSAD&OE9 # XSSD&OE10;
        SDACD.clk = !TFMHZ;

end
```

```
            FIN  := (BCNT==16) # FIN&!(BCNT==17);
            SYNC = CNTHZ&(CNTL==200) # SYNC&!(FIN # !BCOK # LNKRST # CNTLCY);
            STOPCNT = (BCNT==17)&!FIN # CNTHCY # CNTLCY # LNKRST # !BCOK #
STOPCNT&!(CNTH==200);

"store serial data in SD register

SD.ar = !BCOK # LNKRST;
            SD  := [SD14..SD0,1]&SYNC&(CNTH==100) # [SD14..SD0,0]&SYNC&(CNTH==40);
            SD.clk = SYNC&!SDIN;

"detect and store function code

LCS    = FIN&(FC==1);
            SCSIO  = FIN&(FC==2);
            LGV    = FIN&(FC==3);
            LNKRST = FIN&(FC==15);

"FC==0000 Static focus DAC data

SFD.ar = !BCOK;
            SFD.d  = SHIFTSF&[SFD18..SFD3,0,0,0,0] #
!SHIFTSF&LDSR&[!SD11,SD10..SD0,0,0,0,0,0,0,0,0];
            SFD.clk = !TFMHZ&(SHIFTSF # LDSR);

LTCHENSF.d = (SFCNT==20)&SHIFTSF # LTCHENSF&!(SFCNT==24);
            LTCHENSF.clk = !TFMHZ;
            CLKSF = TFMHZ&!LTCHENSF&SHIFTSF;
            SHIFTSF.d = LDSR # SHIFTSF&!(SFCNT==20);
            SFCNT.t = SFCNT$(SFCNT + 1)&!LDSR&!SFCCY # SFCNT&(LDSR # SFCCY);
            SFCCY = (SFCNT==24);
            LDSR.d = FIN&(FC==0)&(BCNT==16) # !BCOK&(SFCNT==24);

"Store Current Sense Data

SDO := CSSHIFT&[0,0,0,!OT1_,SDO10..SDO0,CSDATA] # SDOS&[SDO14..SDO0,0];
            SDO.clk = CSSHIFT&SCLK # SDOS&!SDOUT;

"SDOUT Controls

SDOUT = SDOSYNC # ONE # ZERO;

START   = DONE # START&!(OCNT==16);
            SDOSYNC = DONE # SDOSYNC&!(ECYL);
            LOCKOUT = DONE # LOCKOUT&!(!SDOSYNC&ECY);
            HOLDOFF = DONE # HOLDOFF&!(!LOCKOUT&(ECNT==2));
            SDOS    = START&!HOLDOFF # SDOS&!(!START);

ZEROHOLD = !SDO15&(ECNT==1)&START&!LOCKOUT;
            ONEHOLD  =  SDO15&(ECNT==1)&START&!LOCKOUT;

ONE  = ONEHOLD  # ONE&!(ECNT==126);
            ZERO = ZEROHOLD # ZERO&!(ECNT==51);

"SDOUT counters

ECNT.ar = !START;
            ECNT.t  = START&(ECNT$(ECNT + 1)) # ECNT&(ECY);
            ECY  = (ECNT==250);
            ECYL := ECY;

OCNT.ar = !START;
            OCNT.t  = START&(OCNT$(OCNT + 1));
            OCNT.clk = SDOS&!SDOUT;

end
```

APPENDIX A(4)

```
module bciser title 'Beam Controller Interface -- Serial Control
        Ver. 0; 1-9-95 2330'
        B1U25R0 device 'MACH435A';

"inputs
        TFMHZ,OT1_ pin 20,40;
        SDIN pin 41;
        CSDATA,BCOK pin 10,83;
        SCLK pin 5;
        CSSHIFT,DONE pin 62,65;

"outputs
        SDOUT pin 24;
        CLKSF pin 45;
        LTCHENSF,SDSF pin 47,48 istype 'reg_D,buffer';
        LGV,LCS,SCSIO pin 7,8,9;
        SD15..SD0 pin 15,16,17,18,55..61,12,13,14,19,54 istype 'reg_D,buffer';

"nodes
        CNTHL,SYNC,STOPCNT,SFCCY,LNKRST,CNTHCY,CNTLCY node;
        CNTH8..CNTH0,CNTL8..CNTL0 node istype 'reg_T,buffer';
        BCNT4..BCNT0 node istype 'reg_T,buffer';

SFD18..SFD0,LDSR,SHIFTSF,FIN node istype 'reg_D,buffer';
        SFCNT4..SFCNT0 node istype 'reg_T,buffer';

ZEROHOLD,ONEHOLD,START,SDOSYNC,ONE,ZERO,LOCKOUT,ECY,SDOS,HOLDOFF node;
        ECNT7..ECNT0,OCNT4..OCNT0 node istype 'reg_T,buffer';
        SDO15..SDO0,ECYL node istype 'reg_D,buffer';

"constants
        H,L,C,P,X,Z = 1,0,.C.,.P.,.X.,.Z.;
        CNTH    = [CNTH8..CNTH0];
        CNTL    = [CNTL8..CNTL0];
        SD      = [SD15..SD0];
        BCNT    = [BCNT4..BCNT0];
        FC      = [SD15..SD12];

SFD     = [SDSF,SFD18..SFD0];
        SFCNT   = [SFCNT4..SFCNT0];

SDO     = [SDO15..SDO0];
        ECNT    = [ECNT7..ECNT0];
        OCNT    = [OCNT4..OCNT0];

TF      = .[CNTH,CNTL,FIN,SHIFTSF,LDSR,SFCNT,ECNT,ECYL];

equations

"clock generation

TF.clk = TFMHZ;

"serial data control

CNTH.t = CNTHS(CNTH + 1)&SDIN # CNTH&(!SDIN # CNTHCY);
        CNTHCY = (CNTH==301);
        CNTHL  = (CNTH==200) # CNTHL&!((CNTH==1) # CNTHCY);          "+/-20%
        CNTL.ar = STOPCNT;
        CNTL.t = CNTL$(CNTL + 1)&!SDIN # CNTL&SDIN;
        CNTLCY = (CNTL==301);
        BCNT.ar = STOPCNT;
        BCNT.t = BCNTS(BCNT + 1);
        BCNT.clk = !SDIN&SYNC&!CNTHL # TFMHZ&FIN;
```

13k

What is claimed is:

1. An x-ray source comprising a charged particle beam generator and a vacuum envelope assembly;

said charged particle beam generator comprising an outer casing, a high-voltage terminal and an electron gun;

said high-voltage terminal comprising electronic components to power said electron gun;

said vacuum envelope assembly comprising an outer casing, charged particle beam focussing means for focussing an electron beam generated by said charged particle beam generator, a target, and charged particle beam deflection means for deflecting said electron beam in a step pattern at said target; said target operated at ground potential;

said charged particle beam deflection means comprising a beam controller, a fast deflection yoke and a slow deflection yoke, said beam controller having current outputs comprising an x-deflection current and an x-step current;

said x-deflection current having a triangular waveform with a non-zero substantially constant slope during the period of time it takes said electron beam to travel across the face of said target;

said x-step current comprising a waveform having a plurality of substantially sawtoothed shapes during the period of time it takes said electron beam to travel across the face of said target;

said slow deflection yoke comprising x-deflection coils and y-deflection coils, said x-deflection coils operably coupled to said beam controller and having an input electrically coupled to said x-deflection current;

said fast deflection yoke comprising x-step deflection coils operably coupled to said beam controller, said x-step deflection coils having lower inductance than said x-deflection coils and said y-deflection coils, said x-step deflection coils having an input electrically coupled to said x-step current.

2. The x-ray source of claim 1 wherein said current output further comprises a y-step current, said y-step current comprising a periodic substantially sawtooth waveform with a period less than the time it takes said electron beam to travel across the face of said target;

said fast deflection yoke further comprises y-step deflection coils operably coupled to said beam controller, said y-step deflection coils having lower inductance than said x-deflection coils and said y-deflection coils, said y-step deflection coils having an input coupled to said y-step current.

3. The x-ray source of claim 1 wherein said charged particle beam focussing means comprises a static focus coil and a dynamic focus coil, said dynamic focus coil having lower inductance than said static focus coil; a current in said dynamic focus coil synchronized with currents in said charged particle beam deflection means.

4. The x-ray source of claim 1 wherein said fast deflection yoke further comprises a rotational alignment assembly.

5. The x-ray source of claim 1 wherein said slow deflection yoke further comprises a rotational alignment assembly.

6. The x-ray source of claim 1 wherein said charged particle beam focussing means comprises an axial alignment assembly.

7. The x-ray source of claim 1 wherein said charged particle beam focussing means comprises a radial alignment assembly.

8. The x-ray source of claim 1 wherein a coolant flows in direct contact with said target.

9. The x-ray source of claim 1 wherein said outer casing comprises a first and a second wall, with a coolant flowing between said first and said second walls.

10. The x-ray source of claim 1 wherein said target comprises a target layer and a support layer;

said target layer comprising a layer of tantalum and a layer of niobium, said support layer comprising beryllium, said niobium forming an intermediate layer between said tantalum and said support layer.

11. The x-ray source of claim 1 wherein said target comprises a target layer and a support layer;

said target layer comprising a layer of tungsten-rhenium alloy.

12. The x-ray source of claim 1 wherein said target comprises a target layer and a support layer;

said target layer comprising a layer of tungsten-rhenium alloy and an intermediate niobium layer.

13. The x-ray source of claim 1 further comprising fiber optic links to control said electronic components.

14. An x-ray source comprising a charged particle beam generator and a vacuum envelope assembly;

said charged particle beam generator comprising an outer casing, a high-voltage terminal and an electron gun;

said high-voltage terminal comprising electronic components to power said electron gun;

said vacuum envelope assembly comprising an outer casing, a target, charged particle beam focussing means for focussing an electron beam generated by said charged particle beam generator, charged particle beam deflection means for deflecting said electron beam in a step pattern at said target, and a collimator, said target operated at ground potential;

said collimator comprising a plurality of rows and columns of x-ray transmissive apertures;

said charged particle beam deflection means comprising a beam controller, a fast deflection yoke and a slow deflection yoke, said beam controller having as its output control signals comprising an x-deflection signal and an x-step signal, said x-deflection signal comprising a waveform having a non-zero substantially constant slope when said electron beam is positioned along said target adjacent to a single row of said plurality of rows of apertures on said collimator, said x-step signal having a waveform with a plurality of periodic sawtooth shapes when said electron beam is positioned along said target adjacent to a single row of said plurality of rows of apertures on said collimator;

said slow deflection yoke comprising x-deflection coils and y-deflection coils, said x-deflection coils coupled to said x-deflection signal;

said fast deflection yoke comprising x-step deflection coils, said x-step deflection coils coupled to said x-step signal and having lower inductance than said x-deflection coils and said y-deflection coils.

15. The x-ray source of claim 14 wherein said fast deflection yoke further comprises a y-step deflection coils, said output of said beam controller further comprises a y-step current coupled to said y-step deflection coils, said y-step current comprising a periodic substantially sawtoothed waveform having a period substantially the same as the time it takes to deflect said electron beam from a position substantially behind a first row of x-ray transmissive apertures on said target to another position behind a second row of x-ray transmissive apertures on said target.

16. The x-ray source of claim 14 wherein said output of said beam controller further comprise a y-deflection signal coupled to said y-deflection coils, said y-deflection signal comprising a waveform having a slope of substantially zero when said electron beam is deflected across said target in substantial alignment with a single row of said plurality of rows of x-ray transmissive apertures of said collimator and said y-deflection signal comprising a waveform having a substantially constant non-zero slope when said electron beam is deflected from a position substantially behind one of said x-ray transmissive apertures of a first row of x-ray transmissive apertures at one end of said target to one of said x-ray transmissive apertures of a second row of x-ray transmissive apertures at another end of said target.

17. The x-ray source of claim 14 wherein a coolant flows in direct contact with said target.

18. The x-ray source of claim 14 wherein said charged particle beam deflection means comprises a rotational alignment assembly.

19. The x-ray source of claim 14 wherein said charged particle beam deflection means comprises a rotational alignment assembly.

20. The x-ray source of claim 14 wherein said output of said beam controller further comprises a y-step signal having a substantially sawtoothed waveform;

said fast deflection yoke further comprises y-step deflection coils, said y-step deflection coils coupled to said y-step signal.

* * * * *